US005882875A

United States Patent [19]
Deeley et al.

[11] Patent Number: 5,882,875
[45] Date of Patent: Mar. 16, 1999

[54] METHODS FOR IDENTIFYING MULTIDRUG RESISTANT TUMOR CELLS

[75] Inventors: Roger G. Deeley; Susan P. C. Cole, both of Kingston, Canada

[73] Assignee: Queen's University at Kingston, Kingston, Canada

[21] Appl. No.: 462,109

[22] Filed: Jun. 5, 1995

Related U.S. Application Data

[63] Continuation-in-part of Ser. No. 407,207, Mar. 20, 1995, which is a continuation-in-part of Ser. No. 141,893, Oct. 26, 1993, Pat. No. 5,489,519, which is a continuation-in-part of Ser. No. 29,340, Mar. 8, 1993, abandoned, which is a continuation-in-part of Ser. No. 966,923, Oct. 27, 1992, abandoned.

[51] Int. Cl.$^6$ .................................................. G01N 33/53
[52] U.S. Cl. ................... 435/7.23; 424/155.1; 530/388.8
[58] Field of Search .............................. 530/387.3, 387.7, 530/387.9, 388.8, 391.7; 435/7.1, 7.23; 436/542, 536; 424/155.1

[56] References Cited

U.S. PATENT DOCUMENTS

| | | | |
|---|---|---|---|
| 4,474,893 | 10/1984 | Reading | 436/547 |
| 4,722,899 | 2/1988 | Hamaoka et al. | 435/172.2 |
| 4,912,039 | 3/1990 | Riordan | 435/69.1 |
| 5,166,059 | 11/1992 | Pastan et al. | 435/69.7 |
| 5,198,344 | 3/1993 | Croop et al. | 435/69.1 |
| 5,206,352 | 4/1993 | Roninson et al. | 536/24.31 |

OTHER PUBLICATIONS

Abbaszadegan, M.R. et al. (1994) "Analysis of Multidrug Resistance–associated Protein (MRP) Messenger RNA in Normal and Malignant Hematopoietic Cells" *Cancer Research* 54: 4676–4679.

Almquist, K.C. et al. (1995) "Characterization of the M$_r$ 190,000 Multidrug Resistance Protein (MRP) in Drug–Selected and Transfected Human Tumor Cells" *Cancer Research* 55: 102–110.

Barrand, M.A. et al. (1992) "Chemosensitisation and Drug Accumulation Effects of Cyclosporin A, PSC–833 and Verapamil in Human MDR Large Cell Lung Cancer Cells Expressing a 190k Membrane Protein Distinct from P–glycoprotein" *Eur J. Cancer* 29A(3):408–415.

Bordow, S.B. et al. (1994) "Expression of the Multidrug Resistance–associated Protein (MRP) Gene Correlates with Amplification and Overexpression of the N–myc Oncogene in Childhood Neuroblastoma" *Cancer Research* 54: 5036–5040.

Brock, I. et al. (1995) "Sequential Coexpression of the Multidrug Resistance Genes MRP and mdr1 and Their Products in VP–16 (Etoposide)–selected H69 Small Cell Lung Cancer Cells" *Cancer Research* 55: 459–462.

Burger, H. et al. (1994) "Expression of the Multidrug Resistance–Associated Protein (MRP) in Acute and Chronic Leukemias" *Leukemia* 8(6): 990–997.

Chen, C–J. et al. (1986) "Internal Duplication and Homology with Bacterial Transport Proteins in the mdr1 (P–Glycoprotein) Gene from Multidrug–Resistant Human Cells" *Cell* 47: 381–389.

Cole, S.P.C. et al. (1993) "A Novel ATP–Binding Cassette Transporter Gene Overexpressed in Multidrug–Resistant Human Lung Tumor Cells" *Proc. Am. Assoc. Cancer. Res.* 34: 579 (Abstract).

Cole, S.P.C. et al. (1989) "Effect of Calcium Antagonists on the Chemosensitivity of Two Multidrug–Resistant Human Tumor Cell Lines Which do not Overexpress P–glycoprotein" *Br. J. Cancer* 59:42–46.

Cole, S.P.C. et al. (1992) "Elevated Expression of Annexin II (Lipocortin II, p36) in a Multidrug Resistant Small Cell Lung Cancer Cell Line" *J. Cancer* 65: 498–502.

Cole, S.P.C. et al. (1993) "MRP: A Novel ATP–Binding Cassette Transporter Gene Isolated From a Multidrug Resistant Small Cell Lung Cancer Cell Line" *Third International IASLC Workshop on Lung Tumor and Differentiation Antigens* (Abstract).

Cole, S.P.C. and R.G. Deeley (1993) "Multidrug Resistance–Associated Protein: Sequence Correction" *Science* 260: 879.

Cole, S.P.C. et al (1992) "Overexpression of a Transporter Gene in a Multidrug–Resistant Human Lung Cancer Cell Line" *Science* 258:1650–1654.

Cole, S.P.C. (1990) "Patterns of Cross–Resistance in a Multidrug–Resistant Small–Cell Lung Carcinoma Cell Line" *Cancer Chemother.Pharmacol* 26: 250–256.

Cole, S.P.C. et al. (1994) "Pharmacological Characterization of Multidrug Resistant MRP–transfected Human Tumor Cells" *Cancer Research* 54: 5902–5910.

Cole, S.P.C. (1991) "The 1991 Merck Frosst Award. Multidrug Resistance in Small Cell Lung Cancer" *Can. J. Physiol. Pharmacol.* 70: 313–329.

DelaFlor–Weiss, E. et al. (1992) "Transfer and Expression of the Human Multidrug Resistance Gene in Mouse Erythroleukemia Cells" *Blood* 80(12):3106–3111.

Flens, M.J. et al. (1994) "Immunochemical Detection of the Multidrug Resistance–associated Protein MRP in Human Multidrug–resistant Tumor Cells by Monoclonal Antibodies" *Cancer Research* 54: 4557–4563.

Fojo, A.T. et al. (1985) "Amplification of DNA Sequences in Human Multidrug–Resistant KB Carcinoma Cells" *Proc. Natl. Acad. Sci. USA* 82:7661–7665.

(List continued on next page.)

*Primary Examiner*—Sheela Huff
*Assistant Examiner*—Julie E Reeves
*Attorney, Agent, or Firm*—Carol Miernicki Steeg; Catherine J. Kara; Giulio A. DeConti, Jr.

[57] ABSTRACT

A novel protein associated with multidrug resistance in living cells and capable of conferring multidrug resistance on a cell is disclosed. Nucleic acids encoding the novel multidrug resistance protein are also disclosed. Transformant cell lines which express the nucleic acid encoding the novel protein are also disclosed. Antibodies which bind the novel multidrug resistance protein are also disclosed. Diagnostic and treatment methods using the novel proteins, nucleic acids, antibodies and cell lines of the invention are also encompassed by the invention.

17 Claims, 21 Drawing Sheets

OTHER PUBLICATIONS

Grant, C.E. et al. (1994) "Overexpression of Multidrug Resistance–Associated Protein (MRP) Increases Resistance to Natural Product Drugs" *Cancer Research* 54: 357–361.

Gros, P. et al. (1986) "Isolation and Characterization of DNA Sequences Amplified in Multidrug–Resistant Hamster Cells" *Proc. Natl. Acad. Sci. USA* 83: 337–341.

Higgins, C.F. (1992) "ABC Transporters: From Microorganisms to Man" *Annu. Rev. Cell Biol.* 8:67–113.

Hipfner, D.R. (1994) "Detection of the $M_r$ 190,000 Multidrug Resistance Protein, MRP, with Monoclonal Antibodies" *Cancer Research* 54: 5788–5792.

Hyde, S.C. et al. (1990) "Structural Model of ATP–Binding Proteins Associated With Cystic Fibrosis, Multidrug Resistance and Bacterial Transport" (1990) *Nature* 346:362–365.

Jeditschky, G. et al. (1994) "ATP–Dependent Transport of Glutathione S–Conjugates by the Multidrug Resistance–Associated Protein" *Cancer Research* 54: 4833–4836.

Jirsch, R.G. et al. (1993) "Inwardly Rectifying $K^+$ Channels and Volume–regulated Anion Channels in Multidrug–resistant Small Cell Lung Cancer Cells" *Cancer Research* 53:1–5.

Krebs, K.A. et al. (1993) "Peripheral Blood Mononuclear Cells Express Antigens Associated with Multidrug Resistance in a Small Cell Lung Cancer Line" *Anticancer Research* 13: 317–322.

Krishnamachary, N. and M.S. Center (1993) "The MRP Gene Associated with a Non–P glycoprotein Multidrug Resistance Encodes a 190–kDa Membrane Bound Glycoprotein" *Cancer Research* 55: 3658–3661.

Kruh, G.D. et al. (1994) "Expression Complementary DNA Library Transfer Establishes mrp as a Multidrug Resistance Gene" *Cancer Research* 54: 1649–1652.

Kuss, B.J. et al. (1994) "Deletion of Gene for Multidrug Resistance in Acute Myeloid Leukaemia with Inversion in Chromosome 16: Prognostic Implications" *The Lancet* 343:1531–1534.

Leier, Inka et al. (1994) "The MRP Gene Encodes an ATP–dependent Export Pump for Leukotriene $C_4$ and Structurally Related Conjugates" *The Journal of Biological Chemistry* 269(45): 27807–27810.

Marquardt, D. et al. (1990) "Mechanisms of Multidrug Resistance in HL60 Cells: Detection of Resistance–Associated Proteins with Antibodies Against Synthetic Peptides That Correspond to the Deduced Sequence of P–Glycoprotein" *Cancer Res.* 50:1426–1430.

Mirski, S.E.L. et al. (1987) "Multidrug Resistance in Human Small Cell Lung Cancer Cell Line Selected in Adriamycin" *Cancer Research* 47: 2594–2598.

Ouellette, M. et al. (1990) "The Amplified H Circle of Methotrexate–Resistant Leishmania Tarentolae Contains a Novel P–glycoprotein Gene" *EMBO J.* 9(4):1027–1033.

Papadopoulou, B. et al. (1994) "Contribution of the Leishmania P–glycoprotein–related Gene ItpgpA to Oxyanion Resistance" *Journal of Biological Chemistry* 269(16): 11980–11986.

Podda, S. et al. (1992) "Transfer and Expression of the Human Multiple Drug Resistance Gene into Live Mice" *Proc. Natl. Acad. Sci. USA* 89:9676–9680.

Riordan, J.R. et al. (1985) "Amplification of P–glycoprotein Genes in Multidrug–Resistant Mammalian Cell Lines" *Nature* 316:817–819.

Rivoltini, L. et al. (1990) "Modulation of Multidrug Resistance By Verapamil or mdr1 Anti–Sense Oligodeoxynucleotide Does Not Change The High Susceptibility to Lymphokine–Activated Killers in mdr–Resistant Human Carcinoma (LoVo) Line" *Int. J. Cancer* 46:727–732.

Roninson, I.B. et al. (1984) "Amplification of Specific DNA Sequences Correlates with Multi–drug Resistance in Chinese Hamster Cells" *Nature* 309: 626–628.

Roninson, I.B. et al. (1986) "Isolation of Human mdr DNA Sequences Amplified in Multidrug–Resistant KB Carcinoma Cells" *Proc. Natl. Acad. Sci. USA* 83:4538–4542.

Slovak, M.L. et al. (1993) "Localization of a Novel Multidrug Resistance–associated Gene in the HT1080/DR4 and H69AR Human Tumor Cell Lines" *Cancer Research* 53: 3221–3225.

Sumizawa, T. et al. (1994) "Non–P–Glycoprotein–Mediated Multidrug–Resistant Human KB Cells Selected in Medium Containing Adriamycin, Cepharanthine, and Mezerein" *Somatic Cell and Molecular Genetics* 20(5):423–435.

Sugawara, I. et al. (1994) "Expression of Multidrug Resistance–associated Protein (MRP) in Anaplastic Carcinoma of the Thyroid" *Cancer Letters* 82: 185–188.

Szczypka, M.S. (1994) "A Yeast Metal Resistant Protein Similar to Human Cystic Fibrosis Transmembrane Conductance Regulator (CFTR) and Multidrug Resistance–associated Protein" *Journal of Biological Chemistry* 269(36): 22853–22857.

Ueda, K. et al. (1986) "The mdr1 Gene, Responsible For Multidrug–Resistance, Codes For P–Glycoprotein" *Biochem. and Biophys. Res. Comm.* 141(3):956–962.

Zaman, G.J.R. et al. (1994) "The Human Multidrug Resistance–associated Protein MRP is a Plasma Membrane Drug–efflux Pump" *Proc. Natl. Acad. Sci USA* 91: 8822–8826.

van Dijk et al Int J Cancer vol. 44 738–743, 1989.

Seaver Genetic Eng News vol. 14 No. 14 pp. 10 and 14, Aug. 1994.

Efferth et al Med Oncol and Tumor Pharmacother vol. 9 No. 1 11–19, 1992.

Reeck et al Cell vol. 50 667, Aug. 1987.

Lewin et al Science vol. 237 1570, 1987.

Meyers et al Cancer Research vol. 49 3209–3214, Jun. 1989.

Leonardo et al Int J Cancer vol. 57 841–846, 1994.

Hamada et al Proc Natl Acad Sci USA vol. 83 7785–7789, Oct. 1986.

Cianfriglia et al Int J Cancer vol. 56 153–160, 1994.

Cenciarelli et al Int J Cancer vol. 47 533–543, 1991.

Mechetner et al Proc Natl Acad Sci USA vol. 89 5824–5828, Jul. 1992.

Burgess et al Journal Cell Biol vol. 111 2129–2138, Nov. 1990.

Lazar et al Moleculat and Cellular Biology vol. 8 No. 3 1247–1252, Mar. 1988.

Schwartz et al Proc Natl Acad Sci USA vol. 84 6408–6411, 1987.

Lin et al Biochemistry USA vol. 14 1559–1563, 1975.

Creighton, T.E. Proteins: Structure and Molecular Principles, WH Freeman and Co NY 93–98, 1983.

Creighton, Prog Biophys Molec Biol vol. 33 231–297, 1975.

Seaver et al Genetic Engineering News vol. 14 No. 14 pp. 10 and 21, 1994.

Seiver et al Clin Chem vol. 27 No. 11 1797–1806, 1981.

Marquardt et al Cancer Research vol. 50 1426–1430, Mar. 1990.

Krishnamachary et al Cancer Research vol. 53 3658–3661, Aug. 1993.

Marglin et al Ann Reve Biochem vol. 39 841–866, 1970.
Lerner et al Nature vol. 299 591–596, 1982.
Harlow et al Antibodies: A laboratory manual Hcapter 5, pp. 53–71, 1988.
Galfre et al Methods in Enzymology vol. 73 1–46, 1981.
Paul, WE Fundamental Immunology Third edition, p. 242, 1993.

Grant et al Cancer Research vol. 54 357–361, Jan. 1994.

Zuckier et al Seminars in Nuclear Medicine vol. XIX No. 3 166–186, Jul. 1989.

Kruh et al Cancer Research vol. 54 1649–1652, Apr. 1994.

Cole et al Cancer Research vol. 54 5901–5910, Nov. 1994.

| | | |
|---|---|---|
| Hum/MRP | MALRGFCSADGSDPLWDWNVTWNTSNPDFTKCFQNTV | 37 |
| Hum/MRP | LVWVPCFYLWACFPFYFLYLSRHDRGYIQMTPLNKTK | 74 |
| Lei/PgpA |                              MVDNGHVT | 8 |
| Hum/MRP | TALGFLLWIVCWADLFY-SFWERSRGIFLAPVFLVSP | 110 |
| Lei/PgpA | IAMADLGTVVEIAQVRCQQEAQRKFAEQLDELWGGEP | 45 |
| Hum/MRP | TLLGITTLLATFLIQLERRKGVQSSGIMLTFWLVALV | 147 |
| Lei/PgpA | AYTPTVEDQASWFQQL------------YYGWIGDYI | 70 |
| Hum/MRP | CALAILRSKIMTALKEDAQVDLFRDITFYVYFSLLLI | 184 |
| Lei/PgpA | YKAAA--GNITEA---DLPPPTRSTRTYHIGRKLSRQ | 102 |
| Hum/MRP | QLVLSCFSDRSPLFSETIHDPNPCPESSASFLSRITF | 221 |
| Lei/PgpA | AHADIDASRRWQGYIGCEVVYKSCAEAKG------VL | 133 |
| Hum/MRP | WWITGLIVRGYRQPLEGSDLWSLNKEDTSEQVVPVLV | 258 |
| Lei/PgpA | RWVGHLQQSDYPRSLVAGVEWRMP------------P | 158 |
| Hum/MRP | KNWKKECAKTRKQPVKVVYSSKDPAQPKESSKVDANE | 295 |
| Lei/PgpA | RHRRLAVLGSAAALHNGVVHGERLFWPHEDNYLCSCE | 195 |
| Hum/MRP | EVEALIVKS------PQKEWNPSLFKVLYKTFGPYFL | 326 |
| Lei/PgpA | PVEQLYVKSKYNLIPPRPPPSPDLLRTLFKVHWYHVW | 232 |

Fig. 3A-1

| | | |
|---|---|---|
| Hum/MRP | MSFFFKAIHDLMMFSGPQILKLLIKFVNDTKAPDWQG | 363 |
| | . : . :. . : .: ..:...: : : | |
| Lei/PgpA | AQILPKLLSDVTALMLPVLLEYFVKYLNADNATWGWG | 269 |

| | | |
|---|---|---|
| Hum/MRP | YFYTVLLFVTACLQTLVLHQYFHICFVSGMRIKTAVI | 400 |
| | . .:.: .: : : :: : | |
| Lei/PgpA | LGLALTIFLTNVIQSCSAHKYDHISIRTAALFETSSM | 306 |

| | | |
|---|---|---|
| Hum/MRP | GAVYRKALVITNSA--RKSSTVGEIVNLMSVDAQRFM | 435 |
| | .. : . . : :: : :. : | |
| Lei/PgpA | ALLFEKCFTVSRRSLQRPDMSVGRIMNMVGNDVDNIG | 343 |

| | | |
|---|---|---|
| Hum/MRP | DLATYINMIWSAPLQVILALYLLWLNLGPSVLAGVAV | 472 |
| | : :. :::::::..: : :: .: . : :: | |
| Lei/PgpA | SLNWYVMYFWSAPLQLVLCLLLLIRLVGWLRVPGMAV | 380 |

| | | |
|---|---|---|
| Hum/MRP | MVLMVPVNAVMAMKTKTYQVAHMKSKDNRIKLMNEIL | 509 |
| | . . .:. :: : ::: ::.: | |
| Lei/PgpA | LFVTLPLQAVISKHVQDVSERMASVVDLRIKRTNELL | 417 |

| | | |
|---|---|---|
| Hum/MRP | NGIKVLKLYAWELAFKDKVLAIRQEELKVLKKSAYLS | 546 |
| | :.....:. :: : .. : ::. :. | |
| Lei/PgpA | SGVRIVKFMGWEPVFLARIQDARSRELRCLRDVHVAN | 454 |

| | | |
|---|---|---|
| Hum/MRP | AVGTFTWVCTPFLVALCTFAVYVTIDENNILDAQTAF | 583 |
| | : :: :: : .: .: : | |
| Lei/PgpA | VFFMFVNDATPTLVIAVVFILYHV--SGKVLKPEVVF | 489 |

| | | |
|---|---|---|
| Hum/MRP | VSLALFNILRFPLNILPMVISSIVQASVSLKRLRIFL | 620 |
| | .::.: .: . .: .::::.: :: ::. :. | |
| Lei/PgpA | PTIALLNTMRVSFFMIPIIISSILQCFVSAKRVTAFI | 526 |

| | | |
|---|---|---|
| Hum/MRP | SHEE-----------------LEPDSIE------- | 631 |
| | . . :: | |
| Lei/PgpA | ECPDTHSQVQDIASIDVPDAAAIFKGASIHTYLPVKL | 563 |

Fig. 3A-2

```
Hum/MRP   ------------------RRPVKD---------GGGT         641
                            :: :  .
Lei/PgpA  PRCKSRLTAMQRSTLWFRRRGVPETEWYEVDSPDASA         600

Hum/MRP   NSITVRNATFTWARSDPPT-------------------        660
          :. :    :
Lei/PgpA  SSLAVHSTTVHMGSTQTVITDSDGAAGEDEKGEVEEG         637

Hum/MRP   ------------LNGITFSIPEGALVAVVGQVGCGKL         685
                      :  . .:: : :   :.:  : ::
Lei/PgpA  DREYYQLVSKELLRNVSLTIPKGKLTMVIGSTGSGKS         674
                                         A

Hum/MRP   SLLSALLAEMDKVEGHVAIKGSVAYVPQQAWIQNDSL         722
          :: ::.. :        :  .    :..:::::::::  :   .
Lei/PgpA  TLLGALMGEYSVESGELWAERSIAYVPQQAWIMNATL         711

Hum/MRP   RENILFGCQLEEPYYRSVIQACALLPDLEILPSGDRT         759
          :  ::::         :: :  :  ::    .  :    :
Lei/PgpA  RGNILFFDEERAEDLQDVIRCCQLEADLAQFCGGLDT         748

Hum/MRP   EIGEKGVNLSGGQKQRVSLARAVYSNADIYLFDDPLS         796
          :::: ::::::::: ::::::::::: :  :.:.::::
Lei/PgpA  EIGEMGVNLSGGQKARVSLARAVYANRDVYLLDDPLS         785
                   C                      B

Hum/MRP   AVDAHVGKHIFENVIGPKGMLKNKTRILVTHSMSYLP         833
          :..::::: :   ::     : :. :::.: ::      ::
Lei/PgpA  ALDAHVGQRIVQDVI--LGRLRGKTRVLATHQIHLLP         820

Hum/MRP   QVDVIIVMSGGKISEMGSYQELLARDGAFAEFLRTYA         870
          : :.:.   :: ::     :  . . :    :. : ::
Lei/PgpA  LADYIVVLQHGSIVFAGDFAAFSA--TALEETLR---         852

Hum/MRP   STEQEQDAEENGVTGVSGPGKEAKQMENGMLVTDSAG         907
             :     :     :      .          . :.::
Lei/PgpA  -------GELKGSKDVESCSSD--------VDTESAT         874
```

Fig. 3A-3

```
Hum/MRP    KQLQRQLSSSSSYSGDISRHHNSTAELQKAEAKKEET          944
                   .        .      : :                :
Lei/PgpA   AETAPYVAKAKGLNAE---QETSLAGGEDPLRSDVEA          908

Hum/MRP    WKLMEADKAQTGQVKLSVYWDYMKAIGLFISFLSIF-          980
           .:: .    :: :   : :    :.:  :  .  ..
Lei/PgpA   GRLMTTEEKATGKVPWSTYVAYLKSCGGLEAWGCLLA          945
                                                ---

Hum/MRP    -LFMCNHVSALASNYWLSLWTDDPIVNGTQEHTKVRL         1016
            . .   : : ::  :::..:     .         : :
Lei/PgpA   TFALTECVTA-ASSVWLSIWSTGSLMWSADTYLYVYL          981
           ---------------

Hum/MRP    SVYGALGISQGIAVFGYSMAVSIGGILASRCLHVDLL         1053
             .          .    : .   . ::      :: .: :::
Lei/PgpA   FIVFLEIFGSPLRFFLCYYLIRIG----SRNMHRDLL         1014

Hum/MRP    HSILRSPMSFFERTPSGNLVNRFSKELDTVDSMIPEV         1090
           : :    :::::.  :: :  ..:::  :..   .:   . .
Lei/PgpA   ESIGVARMSFFDTTPVGRVLNRFTKDMSILDNTLNDG         1051

Hum/MRP    IKMFMGSLFNVIGACIVILLATPIAAIIPPLGLIYF          1127
            .. .:     :. .. :    . :        :.
Lei/PgpA   YLYLLEYFFSMCSTVIIMVVVQPFVLVAIVPCVYSYY         1088

Hum/MRP    FVQRFYVASSRQLKRLESVSRSPVYSHFNETLLGVSV         1164
             .  : :: :   .: .  :.  :::.   . : : :
Lei/PgpA   KLMQVYNASNRETRRIKSIAHSPVFTLLEESLQGQRT         1125

Hum/MRP    IRAFEEQERFIHQSDLKVDENQKAYYPSIVANRWLAV         1201
           :   .       .    ..:   : :     : ::::  :
Lei/PgpA   IATYGKLHLVLQEALGRLDVVYSALYMQNVSNRWLGV         1162

Hum/MRP    RLECVGNCIVLFAALFAVISR----HSLSAGLVGLSV         1234
           ::: .    . . :.  ::  .       :   ::. ::.
Lei/PgpA   RLEFLSCVVTFMVAFIGVIGKMEGASSQNIGLISLSL         1199

Fig. 3A-4
```

```
Hum/MRP    SYSLQVTTYLNWLVRMSSEMETNIVAVERLKEYS-ET         1270
           :.  .:  :::::::       : :      :::.   :   :
Lei/PgpA   TMSMTLTETLNWLVRQVAMVEANMNSVERVLHYTQEV         1236

Hum/MRP    EKE-----APWQIQETRPPSSWP--------------         1288
           : :             :   :   :  .
Lei/PgpA   EHEHVPEMGELVAQLVRSESGRGANVTETVVIESAGA         1273

Hum/MRP    --------QVGRVEFRNYCLRYREDLDFVLRHINVTI         1317
                   :  :  . .    .::::  :  .:::  .      :
Lei/PgpA   ASSALHPVQAGSLVLEGVQMRYREGLPLVLRGVSFQI         1310

Hum/MRP    NGGEKVGIVGRTGAGKSSLTLGLFRINESAEGEIIID         1354
           :::::::::::::  :::  :   .  :     :    : .  .
Lei/PgpA   APREKVGIV<u>GRTGSGKS</u>TLLLTFMRMVEVCGGVIHVN         1347
                    A

Hum/MRP    GINIAKIGLHDLRFKITIIPQDPVLFSGSLRMNLDPF         1391
           :         ::   .::      :::::::::   :   .:   :.:::
Lei/PgpA   GREMSAYGLRELRRHFSMIPQDPVLFDGTVRQNVDPF         1384

Hum/MRP    SQYSDEEVWTSLELAHLKDFVSALPDKLDHECAEGGE         1428
            :    :::    :::     :..   :         .   .:      :::
Lei/PgpA   LEASSAEVWAALELVGLRERVASESEGIDSRVLEGGS         1421

Hum/MRP    NLSVGQRQLVCLARALLRKTK-ILVLDEATAAVDLET         1464
           :  :::::::  :.::::::..      ...:::::   .:
Lei/PgpA   N<u>YSVGQRQLMCMA</u>RALLKRGSG<u>FILMD</u>EATANIDPAL         1458
            C                    B

Hum/MRP    DDLIQSTIRTQFEDCTVLTIAHRLNTIMDYTRVIVLD         1501
           :   ::  :.    :    .::.::::::  :.   :   ...:..:
Lei/PgpA   DRQIQATVMSAFSAYTVITIAHRLHTVAQYDKIIVMD         1495

Hum/MRP    KGEIQEYGAPSDL-LQQRGLFYSMAKDAGLV               1531
           :    :  :  :  .:  .      .:  ::      :
Lei/PgpA   HGVVAEMGSPRELVMNHQSMFHSMVESLGSRGSKDFY         1532

Lei/PgpA   ELLMGRRIVQPAVLSD                              1548
```

METHODS FOR IDENTIFYING MULTIDRUG RESISTANT TUMOR CELLS

CROSS REFERENCE TO RELATED APPLICATIONS

This application is a continuation-in-part of application Ser. No. 08/407,207 filed Mar. 20, 1995, pending, which is a continuation-in-part of application Ser. No. 08/141,893 filed Oct. 26, 1993, now U.S. Pat. No. 5,489,519, issued Feb. 6, 1996, which is a continuation-in-part of application Ser. No. 08/029,340 filed Mar. 8, 1993, now abandoned, which is a continuation-in-part of application Ser. No. 07/966,923 filed Oct. 27, 1992, now abandoned, the entire contents of each of which are incorporated herein by reference.

BACKGROUND OF THE INVENTION

It is well known that many types of cancer regress initially in response to currently available drugs. However, if the disease should recur, as it does with variable frequency, it is often refractory to further treatment with either the agent originally used for treatment or agents to which the patient has not been previously exposed. Currently there is little that can be done for patients whose tumors display this form of multidrug resistance.

One mechanism by which cancer cells can simultaneously develop resistance to an array of structurally diverse drugs has been elucidated over the last 15 years with the characterization of P-glycoprotein.

P-glycoprotein is a member of a superfamily of membrane proteins that serve to transport a variety of molecules, ranging from ions to proteins, across cell membranes. This superfamily is known as the ATP-binding cassette (ABC) superfamily of membrane transport proteins. For a review see C. F. Higgins, *Ann. Rev. Cell Biol.* 8, 67 (1992). For example, in addition to P-glycoprotein which transports chemotherapeutic drugs, this family includes the cystic fibrosis transmembrane conductance regulator, which controls chloride ion fluxes, as well as insect proteins that mediate resistance to antimalarial drugs. P-glycoprotein is believed to confer resistance to multiple anticancer drugs by acting as an energy dependent efflux pump that limits the intracellular accumulation of a wide range of cytotoxic agents and other xenobiotics. Compounds that are excluded from mammalian cells by P-glycoprotein are frequently natural product-type drugs but other large heterocyclic molecules are also "substrates" for this efflux pump.

The discovery of P-glycoprotein and its occurrence in a variety of tumor types has stimulated the search for compounds that are capable of blocking its function and consequently, of reversing resistance. These investigations have resulted in identification of a large number of so-called chemosensitizers or reversing agents. Some of these compounds act by inhibiting the pumping action of P-glycoprotein while the mechanism of action of others is still undetermined. A select group of these agents are currently under intensive clinical investigation and they show considerable promise as adjuncts to conventional chemotherapy. Chemosensitizers which can reverse P-glycoprotein-mediated multidrug resistance include verapamil and cyclosporin A.

Unfortunately, overexpression of P-glycoprotein does not explain the high frequency of multidrug resistance in some of the more prevalent forms of cancer, such as lung cancer. In the Western world, lung cancer accounts for approximately 30% of total cancer deaths. There are four major histological categories of lung tumors: epidermoid or squamous cell adenocarcinomas, large cell carcinomas, adenocarcinomas and small cell carcinomas. The first three categories, known collectively as non-small cell lung cancers, differ from the last in their initial response to chemotherapy and radiotherapy. Non-small cell lung cancers are relatively resistant to both forms of treatment from the outset. In contrast, small cell lung cancer, which accounts for 20% of all lung tumors, exhibits a high initial response rate (80–90% in limited disease) to chemotherapy. However, almost all patients relapse with a multidrug resistant form of the disease and two year survival rates are less than 10%. Although the drug resistance profile displayed in relapsed small cell lung cancer patients is similar to that conferred by P-glycoprotein, P-glycoprotein appears not to be involved. In addition, limited studies in cell culture and in patients indicate that multidrug resistance in small cell lung cancer does not respond to chemosensitizers, such as verapamil and cyclosporin A, that show promise with other types of drug resistant tumors.

Survival rates in lung cancer have not improved significantly in forty years and, because of its common occurrence, there is clearly a great need for improved therapy for this disease.

SUMMARY OF THE INVENTION

The present invention is based, at least in part, on the discovery of a nucleic acid which encodes a protein which can confer multidrug resistance on a drug sensitive mammalian cell when expressed in the cell and which is overexpressed in certain multidrug resistant cancer cell lines. The nucleic acid of the invention was isolated from a multidrug resistant cancer cell line which does not overexpress P-glycoprotein and whose resistance is not substantially reversed by chemosensitizers which inhibit P-glycoprotein. The nucleic acid and encoded protein of the present invention represent molecules which can be targeted therapeutically in multidrug resistant tumors expressing the nucleic acid and protein.

The present invention provides an isolated nucleic acid having a nucleotide sequence which encodes a protein associated with multidrug resistance which is overexpressed in multidrug resistant cells independently of overexpression of P-glycoprotein. The protein has been named multidrug resistance-associated protein (referred to as MRP). The protein of the invention differs in amino acid sequence from P-glycoprotein. The isolated nucleic acid, when expressed in a cell which is not multidrug resistant, can confer on the cell multidrug resistance.

In a preferred embodiment, an isolated nucleic acid is provided having a sequence which codes for a protein associated with multidrug resistance having an amino acid sequence which has substantial sequence homology with the amino acid sequence shown in SEQ ID NO: 2. Most preferably the isolated nucleic acid has a sequence having substantial sequence homology with the nucleotide sequence shown in SEQ ID NO: 1. In one embodiment, the invention provides an isolated human MRP nucleic acid molecule, as shown in SEQ ID NO: 1 and encoding a human MRP protein as shown in SEQ ID NO: 2. In another embodiment, the invention provides a natural variant of the human MRP nucleic acid molecule of SEQ ID NO: 1, shown in SEQ ID NO: 3 and encoding a human MRP protein shown in SEQ ID NO: 4, which differs by three nucleotide base pairs from the sequence of SEQ ID NO: 1. In yet another embodiment, the invention provides an isolated mouse MRP nucleic acid molecule, as shown in SEQ ID NO: 5 and encoding a mouse MRP protein as shown in SEQ ID NO: 6. The invention further provides an isolated nucleic acid which is antisense to a nucleic acid having substantial sequence homology with the nucleotide sequence shown in SEQ ID NO: 1.

The invention further provides a recombinant expression vector adapted for transformation of a host cell comprising the nucleic acid of the invention operatively linked to a regulatory sequence. The invention also provides a recombinant expression vector adapted for transformation of a host cell comprising a DNA molecule operatively linked to a regulatory sequence to allow expression of an RNA molecule which is antisense to a nucleotide sequence of SEQ ID NO: 1.

The invention also provides a method of preparing a protein capable of conferring multidrug resistance utilizing the nucleic acid of the invention. The method comprises culturing a transformant host cell including a recombinant expression vector comprising a nucleic acid of the invention and an regulatory sequence operatively linked to nucleic acid in a suitable medium until a multidrug resistance protein is formed and thereafter isolating the protein.

The invention further provides an isolated protein having the biological activity of MRP, which can confer multidrug resistance on a drug sensitive cell when the protein is expressed in the cell, said resistance not being substantially reversed by chemosensitizers of P-glycoprotein. The isolated protein of the invention is associated with multidrug resistance in tumor cells and is overexpressed in multidrug resistant cells which may or may not overexpress P-glycoprotein. In a preferred embodiment the protein has an amino acid sequence which has substantial homology with the amino acid sequence shown in SEQ ID NO: 2.

The invention further provides an antibody specific for an epitope of a protein of the invention. Preferably the antibody is a monoclonal antibody. The antibody can be coupled to a detectable substance or a substance having toxic or therapeutic activity. The invention also provides a bispecific antibody capable of binding to a tumor cell which expresses a protein of the invention and to a detectable substance, or a substance having toxic or therapeutic activity. Preferably, the toxic substance is a cytotoxic cell and the bispecific antibody is capable of crosslinking the tumor cell and the cytotoxic cell thereby facilitating lysis of the tumor cell. The invention further provides a tetrameric antibody complex of a first monoclonal antibody which is capable of binding to a tumor cell expressing a protein of the invention and a second monoclonal antibody which is capable of binding to a detectable substance or a substance having toxic or therapeutic activity wherein the first and second antibody are from a first animal species, conjugated to form a cyclic tetramer with two monoclonal antibodies of a second animal species directed against the Fc fragment of the antibodies of the first animal species.

The antibodies, bispecific antibodies or tetrameric antibody complexes can be incorporated in compositions suitable for administration in a pharmaceutically acceptable carrier.

Molecules which bind to a protein of the invention, including the antibodies, bispecific antibodies and tetrameric antibody complexes of the invention, can be used in a method for identifying multidrug resistant tumor cells by labelling the molecule with a detectable substance, contacting the molecule with tumor cells and detecting the detectable substance bound to the tumor cells. A molecule which binds to a protein of the invention can further be used in a method for inhibiting multidrug resistance of a cell by blocking activity of an MRP protein. A molecule which binds to a protein of the invention can further be used to kill a multidrug resistant cell which expresses the protein by contacting the molecule, coupled to a toxic or therapeutic substance, with the multidrug resistant cell.

Nucleic acids of the invention can be used in a method for protecting a drug sensitive cell from cytotoxicity due to exposure to a drug by transfecting the cell with a nucleic acid in a form suitable for expression of the protein encoded by the nucleic acid in the cell, thereby conferring drug resistance on the cell.

The recombinant molecules of the invention can be used to produce transformant host cells expressing the protein of the invention. The recombinant molecules of the invention can be also used to produce transgenic nonhuman animals and nonhuman knockout animals. The transfected cells, transgenic animals and knockout animals can be used to test substances for their effect on multidrug resistance. A method for identifying a substance which is a chemosensitizer of a therapeutic agent and a method for identifying a cytotoxic substance for multidrug resistant cells, using transformant host cells or animals of the invention, are provided.

The invention also relates to a cell line which is multidrug resistant, does not overexpress P-glycoprotein and is substantially resistant to hydrophobic drugs. The cell line may be derived from small cell lung cancer cells, preferably the cell line NCI-H69. Most preferably the multidrug resistant cell line is H69AR (ATCC CRL 11351). A revertant drug sensitive cell line may be obtained from the multidrug resistant cell line by culturing the multidrug resistant cell line in the absence of a drug for a period of time sufficient to produce a revertant drug sensitive cell line. Preferably the revertant drug sensitive cell line is H69PR (ATCC CRL 11350).

BRIEF DESCRIPTIONS OF THE DRAWINGS

FIG. 3A is the complete amino acid sequence of the multidrug resistance protein of the invention aligned with the complete amino acid sequence of ltPgpA (Lei/PgpA).

FIG. 3B is a diagram showing the alignment of the extended nucleotide binding regions of the multidrug resistance protein of the invention, human CFTR and leishmania ltPgpA and human P-glycoprotein (Hum/Mdr1).

Figure 11:
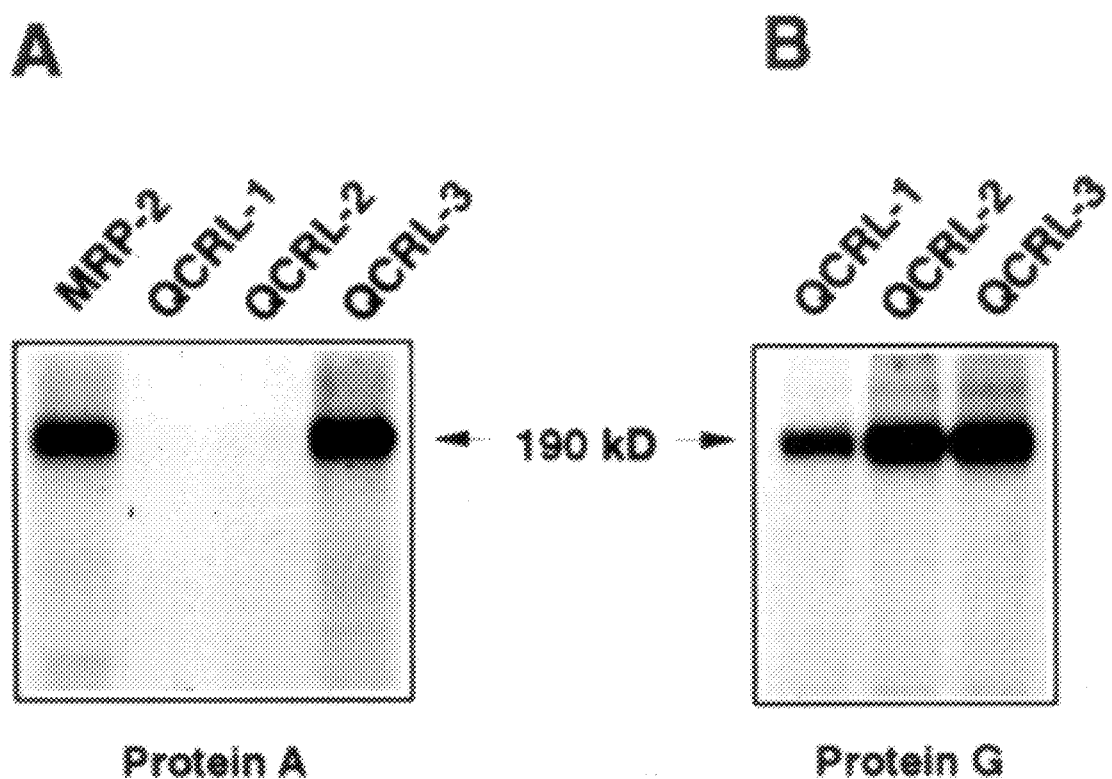

FIG. 11A is a photograph of an immunoprecipitation autoradiograph of labelled proteins from H69AR cells immunoprecipitated with anti-MRP mAbs (QCRL-1, -2 or -3) or anti-MRP peptide antisera (MRP-2). Immune complexes were precipitated with protein A-Sepharose. FIG. 11B is a photograph of an immunoprecipitation autoradiograph of labelled proteins from H69AR cells immunoprecipitated with anti-MRP mAbs (QCRL-1, -2 or -3). Immune complexes were precipitated with protein G-Sepharose.

Figure 12:
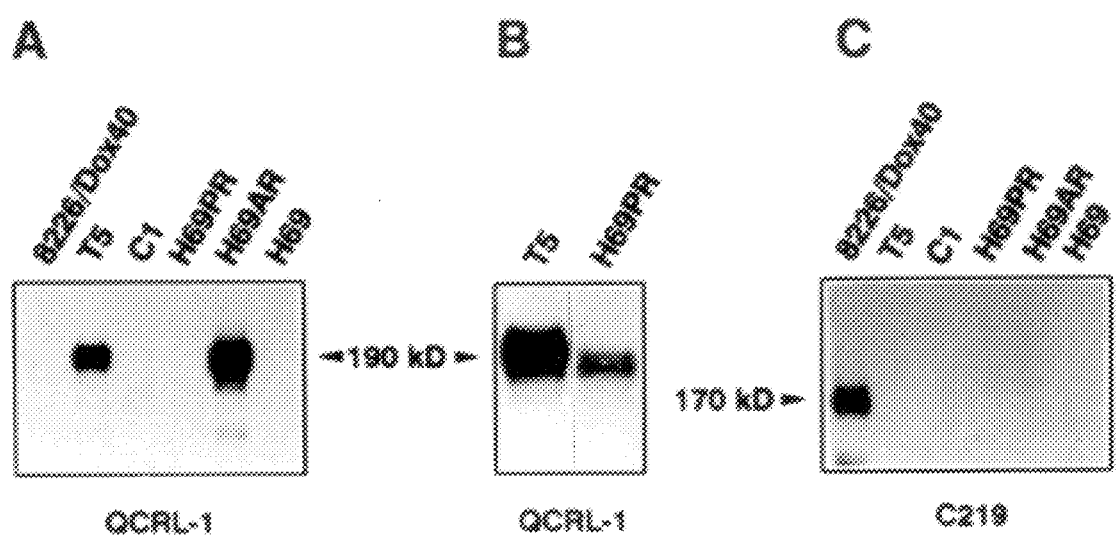

FIG. 12A is a photograph of a western blot of proteins from membrane-enriched fractions of MRP-overexpressing cells (H69AR and T5), P-glycoprotein-overexpressing cells (8226/Dox40) or control cells (H69, H69PR and C1) screened with an anti-MRP mAb A). FIG. 12B is a photograph of a Western blot of proteins from membrance-enriched fractions of MPR-overexpressing cells (T5) or control cells (H69PR) screened with an anti-MRP mAb (QCRL-1). FIG. 12C is a photograph of a Western blot of proteins from membrane-enriched fraction of MRP-overexpressing cells (H69AR and T5), P-glycoprotein-overexpressing cells (8226/Dox40) or control cells (H69, H69PR and C1) screened with an anti-Pgp mAb (C219).

FIG. 13A is a flow cytometric profile of fixed H69, H69AR or H69PR cells reacted with anti-MRP QCRL-3.

FIG. 13B is a flow cytometric profile of fixed T5 or C1 cells reacted with anti-MRP mAb QCRL-3.

DETAILED DESCRIPTION OF THE INVENTION

Multidrug resistant mammalian cell lines have been derived from a number of tumor types and have provided in vitro models for the study of acquired resistance. Although selected by a single natural product-type drug, these cell lines are cross-resistant to a wide range of chemically unrelated xenobiotics with multiple subcellular targets. Typically, these cells are resistant to anthracyclines [e.g. doxorubicin (DOX), epipodophyllotoxins (e.g. VP-16) and the Vinca alkaloids (e.g. vinblastine)] but not to antimetabolites such as 5-fluorouracil, or to platinum-containing drugs. Multidrug resistant cells also frequently exhibit a collateral sensitivity to certain hydrophobic drugs including local anesthetics and steroid hormones.

The most commonly reported alteration in multidrug resistant tumor cells has been the increased expression of the 170 kDa plasma membrane glycoprotein, P-glycoprotein (P-gp), which is encoded by the MDR1 gene. Studies carried out in several laboratories with clinical samples and cell lines representing many tumor types have lead to the conclusion that P-gp, while clinically relevant in some malignancies, is unlikely to be important in others. Overexpression of P-gp is an infrequent occurrence in both small cell lung cancer (SCLC) and non small cell lung cancer (NSCLC).

One of the most widely used cell lines in experimental studies of SCLC is NCI-H69 (H69) (Gazdar et al., *Cancer Res.* 40, 3502–3507 (1980)) (ATCC HTB 119). This cell line was treated repeatedly with an anthracycline, such as daunorubicin or epirubicin and preferably DOX, and step-wise selected to a final concentration of 0.8 $\mu$M, to produce a multidrug resistant cell line, designated as H69AR. A description of the procedures which can be used to produce a multidrug resistant cell line such as H69AR is found in Cole, *Cancer Chemother Pharmacol.* 17, 259–263 (1986) and in Mirski et al., *Cancer Research* 47, 2594–2598 (1987).

The H69AR cell line (ATCC CRL 11351) is about 50-fold resistant to DOX as compared to the parental H69 cell line. H69AR is also cross-resistant to a wide variety of natural product-type drugs. On the other hand, drugs such as carboplatin, 5-fluorouracil and bleomycin are equally toxic to both sensitive H69 and resistant H69AR cells. Although the cross-resistance pattern of H69AR cells is typical of resistance associated with increased levels of P-gp, these cells are different in that they display little or no collateral sensitivity to hydrophobic drugs such as steroids or local anaesthetics. Another distinguishing feature of H69AR of potential clinical relevance that distinguishes it from P-gp overexpressing cell lines is the limited ability of verapamil, cyclosporin A and other chemosensitizing agents that interact with P-gp, to reverse DOX resistance in these cells. The absence of P-gp overexpression supports the suggestion that H69AR provides a clinically relevant model of drug resistance in lung cancer.

A revertant drug sensitive cell line H69PR (Cole et al., *Br J. Cancer* 65, 498–502, 1992) (ATCC CRL 11350) was isolated by culturing the H69AR cell line in the absence of drugs such as DOX for a sufficient time to produce a revertant cell line. Preferably the cell line H69PR is cultured in the absence of drugs for at least 3 months and up to about 48 months, most preferably 42 months.

The cell lines of the invention may be used to assay for a substance that affects a multidrug resistant tumor cell. Cells from a cell line of the invention may be incubated with a test substance which is suspected of affecting multidrug resistance. The effect of the substance can be determined by analyzing the drug resistance pattern of the cells and comparing the results to a control. As discussed above, the multidrug resistant cell line of the invention is resistant to anthracyclines, epipodophyllotoxins, Vinca alkaloids and other natural-product type drugs. Thus, it is possible to screen for an agonist or antagonist substance of multidrug resistance or an antagonist that inhibits the effects of an agonist.

In an embodiment of the invention, a substance that is suspected of being cytotoxic to a multidrug resistant tumor cell can be identified. Therefore, it is possible using the above described method to identify substances which may be useful in the treatment of multidrug resistant tumors.

As described in the Examples, the H69AR cell line has been used to identify a cDNA encoding a novel protein associated with multidrug resistance designated MRP. The DNA sequence and deduced amino acid sequence of MRP are shown in SEQ ID NO: 1 and SEQ ID NO. 2, respectively. MRP mRNA is overexpressed in certain multidrug resistant tumor cell lines, including H69AR. Furthermore, expression of MRP protein in a drug sensitive mammalian cell line confers multidrug resistance on the cell line. A protein described herein as "having biological activity of MRP" can confer on a mammalian cell multidrug resistance to anthracyclines, epipodophyllotoxins and Vinca alkaloids when the protein is expressed in the mammalian cell, and this resistance is not substantially reversed by chemosensitizers which reverse P-glycoprotein-mediated multidrug resistance, such as verapamil or cyclosporin A, in an MRP-dependent manner.

The terms "drug resistant" or "drug resistance" as used herein to describe a property of a cell refer to the ability of the cell to withstand without cytotoxicity increased concentrations of a drug as compared to an appropriate control cell. An appropriate control cell for a cell which has been made drug resistant by continued exposure to a drug is the parental cell from which the drug resistant cell was derived. An appropriate control cell for a cell which has been made drug resistant by expression in the cell of a protein which confers drug resistance on the cell is the same cell without the protein expressed. Appropriate control cells for naturally occurring tumor cells in vivo made drug resistant by continued exposure to a drug are the same tumor cells at the time of initial exposure to the drug.

The invention provides isolated nucleic acids encoding proteins having biological activity of MRP. In a preferred embodiment, the nucleic acid is a cDNA comprising a nucleotide sequence shown in SEQ ID NO: 1. The invention further provides antisense nucleic acids of nucleic acids encoding proteins having biological activity of MRP. The invention further provides recombinant expression vectors comprising the nucleic acids and antisense nucleic acids of the invention and transformant host cells containing recombinant nucleic acids of the invention.

The invention provides isolated proteins having biological activity of MRP and a method for preparing such proteins. In a preferred embodiment, the isolated protein having biological activity of MRP comprises an amino acid sequence shown in SEQ ID NO: 2. The protein comprising the amino acid sequence of SEQ ID NO: 2 is a member of the ABC superfamily of membrane transport proteins. The invention further provides antibodies specific for the isolated proteins of the invention and compositions suitable for administration comprising such antibodies. The invention further provides transgenic and knockout nonhuman animals produced using the nucleic acids of the invention.

The invention provides a method for identifying multidrug resistant cell using the nucleic acids and antibodies of the invention. The invention further provides methods for inhibiting multidrug resistance of a multidrug resistant cell and for killing a multidrug resistant cell using the nucleic acids and antibodies of the invention. The invention further provides methods for identifying substances which are chemosensitizers of therapeutic agents or cytotoxic to drug resistant cells using the transformant host cells and animals of the invention. Furthermore, the invention provides diagnostic kits for identifying drug resistant tumor cells.

These and other aspects of this invention are described in detail in the following subsections.

I. Isolated Nucleic Acids

The invention provides isolated nucleic acids encoding proteins having biological activity of MRP. The term "isolated" refers to a nucleic acid substantially free of cellular material or culture medium when produced by recombinant DNA techniques, or chemical precursors or other chemicals when chemically synthesized. An "isolated" nucleic acid is also free of sequences which naturally flank the nucleic acid (i.e., sequences located at the 5' and 3' ends of the nucleic acid) in the organism from which the nucleic acid is derived. The term "nucleic acid" is intended to include DNA and RNA and can be either double stranded or single stranded. In a preferred embodiment, the nucleic acid is a cDNA comprising a nucleotide sequence shown in SEQ ID NO: 1. In another embodiment, the nucleic acid is a cDNA comprising the coding region of the nucleotide sequence shown in SEQ ID NO: 1. In another embodiment, the nucleic acid encodes a protein comprising an amino acid sequence shown in SEQ ID NO: 2.

It will be appreciated that the invention includes nucleic acids having substantial sequence homology with the nucleotide sequence shown in SEQ ID NO: 1 or encoding proteins having substantial homology to the amino acid sequence shown in SEQ ID NO: 2. Homology refers to sequence similarity between sequences and can be determined by comparing a position in each sequence which may be aligned for purposes of comparison. When a position in the compared sequence is occupied by the same nucleotide base or amino acid, then the molecules are homologous at that position. A degree of homology between sequences is a function of the number of matching or homologous positions shared by the sequences. Examples of sequences having substantial homology to that of SEQ ID NOs: 1 and 2 are naturally-occuring variants thereof from the same species (i.e., humans, from which the nucleic acid of SEQ ID NO: 1 is derived) and homologues from other species (e.g., non-human mammalian forms of MRP). Regarding the former, in one embodiment the invention provides a natural human MRP variant having the nucleotide and encoded amino-acid sequences shown in SEQ ID NOs: 3 and 4, respectively. This variant differs from in nucleotide sequence from that of SEQ ID NO: 1 at three nucleotide positions: 2249 (a change from T to C), 4039 (a change from C to G) and 4040 (a change from G to C).

These nucleotide changes in this human variant lead to two changes in the amino acid sequence of the encoded MRP protein, one at position 685 (a change from a Leu to a Ser) and the other at position 1282 (a change from an Arg to an Ala). Regarding species homologues of the human MRP sequence of SEQ ID NO: 1, in another embodiment the invention provides a murine nucleic acid molecule encoding a murine MRP. The nucleotide sequence and encoded amino acid sequence of a murine MRP cDNA is shown in SEQ ID NOs: 5 and 6, respectively. The human and murine MRP proteins exhibit 88% amino acid identity. The strongest conservation between the two protein is within a stretch of amino acid residues located at positions 1126 to 1239 of the human MRP protein and positions 1123 to 1236 of the mouse MRP protein.

The term "sequences having substantial sequence homology" means those nucleotide and amino acid sequences which have slight or inconsequential sequence variations from the sequences disclosed in SEQ ID NO: 1 and SEQ ID NO: 2, i.e. the homologous nucleic acids function in substantially the same manner to produce substantially the same polypeptides as the actual sequences. The variations may be attributable to local mutations or structural modifications. It is expected that substitutions or alterations can be made in various regions of the nucleotide or amino acid sequence without affecting protein function, particularly if they lie outside the regions predicted to be of functional significance.

Analysis of the protein encoded by SEQ ID NO: 1, comprising the amino acid sequence of SEQ ID NO: 2, reveals 12 hydrophobic stretches predicted to be membrane-spanning regions and of functional importance. These amino acid residues correspond to positions 99–115, 137–153, 175–191, 365–381, 444–460, 466–482, 555–571, 591–607, 969–985, 1028–1044, 1102–1118 and 1205–1221 of SEQ ID NO: 2. Nucleotide substitutions that result in amino acid sequence changes within these regions, especially those that reduce the hydrophobic nature of these regions, are not likely to be translated into a functional protein.

Analysis of the protein encoded by SEQ ID NO: 1, comprising the amino acid sequence of SEQ ID NO: 2, reveals two regions having the structural characteristics of nucleotide binding folds (NBFs) typical of ATP-binding cassette domains (ABC domains). See Hyde, S. C. et al., *Nature* 346, 362–365 (1990). Elements comprising part of the structure of these NBFs are conserved in other members of the ABC superfamily of membrane transport proteins and the domains have been shown to bind nucleotides and to be functionally important. For example see Higgins, C. F., *Ann. Rev. Cell Biol.* 8, 67–113 (1992). In the protein comprising the amino acid sequence shown in SEQ ID NO: 2, the two NBFs are located between about amino acid residues 661–810 and 1310–1469 of SEQ ID NO: 2. Nucleotide and corresponding amino acid substitutions which decrease the degree of homology of these regions compared to other members of the ABC superfamily of membrane transport proteins are likely not to be tolerated in a functional protein. Alternatively, nucleotide and corresponding amino acid substitutions which maintain the structure of an NBF are likely to be tolerated. For example, it has been demonstrated that nucleotides encoding an NBF of one member of the ABC superfamily of membrane transport proteins can be substituted for the homologous domain of another member while maintaining function of the protein. See Buschman, F. and Gros, P. *Mol. Cell. Bio.* 11, 595–603 (1991). Accordingly, the invention provides for a nucleic acid encoding a protein comprising an amino acid sequence represented by V-W-X-Y-Z, wherein V are amino acid residues corresponding to amino acid residues from about 1 to 660 of SEQ ID NO: 2, W are amino acid residues of an NBF substantially homologous with amino acid residues from about 661 to 810 of SEQ ID NO: 2, X are amino acid residues corresponding to amino acid residues from about 811 to 1309 of SEQ ID NO: 2, Y are amino acid residues of an NBF substantially homologous with amino acid residues from about 1310 to 1469 of SEQ ID NO: 2 and Z are amino acid residues corresponding to amino acid residues from about 1470 to 1531 of SEQ ID NO: 2. The term "from about" is intended to mean that the junction between two regions of the protein (e.g. between V and W) may vary by a few amino acids from those specifically indicated.

It is anticipated that, outside of the regions specified above, a nucleic acid encoding a protein comprising an amino acid sequence which is about 50% similar with the amino acid sequence shown SEQ ID NO: 2 will provide functional proteins. Alternatively, proteins comprising an amino acid sequence which is 60%, 70%, 80% or 90% homologous with the amino acid sequence shown SEQ ID NO: 2 may provide proteins having MRP activity. The invention encompasses a nucleic acid encoding a protein having biological activity of MRP which is at least 50% homologous with the amino acid sequence of SEQ ID NO: 2. Specific examples of such additional nucleic acid molecules encoded by the invention include the human MRP variant shown in SEQ ID NOs: 3 (which differs in nucleotide sequence from that of SEQ ID NO: 1 by only three nucleotide base pairs) and the mouse MRP cDNA shown in SEQ ID: 5 (which encodes a mouse MRP protein, shown in SEQ ID NO: 6, which is 88% identical in amino acid sequence to the human MRP protein of SEQ ID NO: 2).

It will further be appreciated that variant forms of the nucleic acids of the invention which arise by alternative splicing of an mRNA corresponding to a cDNA of the invention are encompassed by the invention. Hybridization of a cDNA of the invention, containing all or part of SEQ ID NO: 1, to cellular RNA identifies an mRNA of approximately 6.5 kb with an extended open reading frame of 1531 amino acids. Several cDNA clones have been isolated that contain internal deletions which maintain the original reading frame, suggesting that they may be produced by alternative splicing. The existence of mRNA species containing these deletions was confirmed by reverse PCR of RNA from both multidrug resistant and sensitive cells. In most cases, the variant mRNAs represent minor components of 10% or less. However, some comprise more than 20% of total MRP mRNA. Alternative splice forms have been identified which remove nucleotides 657 to 783 of SEQ ID NO: 1 (amino acids 155–196 inclusive of SEQ ID NO: 2), 1845 to 1992 (amino acids 551–599 inclusive), 2287 to 2463 (amino acids 698–756 inclusive), 2287 to 2628 (amino acids 698–811 inclusive) and 4230 to about 4818 (amino acids 1346 to 1531 inclusive). Two of the more common variants lack segments of the $NH_2$ proximal NBF. Both begin at the same site (amino acid 698) and they affect regions of the cassette that are very near and COOH proximal to the common exon 9 splicing variant of the cystic fibrosis transmembrane conductance regulator (CFTR) mRNA. See Chu, C-S. et al., *EMBO Journal* 10, 1355–1363 (1991). The shorter of the two (amino acids 698–756) eliminates a phenylalanine at a position corresponding to F508 of CFTR. The longer one (amino acids 698–811) removes the active transport family signature that includes the conserved LSGGQ sequence and the Walker B motif. Another of the more common variants (amino acids 1346–1531) lacks a region specifying a segment of the protein close to the COOH terminus, similar to the location affected by alternative splicing of exon 23 of CFTR mRNA. See Yoshimura. K., et al. *J. Biol. Chem.* 268, 686–690 (1993). In addition, two other deletions have been identified, one of which eliminates two of the transmembrane domains in the NH2 proximal half of the molecule (amino acids 551–599), and another which removes a potential secretory signal cleavage site located between amino acids 189/190 (amino acids 155–196).

Another aspect of the invention provides a nucleic acid which hybridizes under high or low stringency conditions to a nucleic acid which encodes a protein having all or a portion of an amino acid sequence shown SEQ ID NO: 2. Appropriate stringency conditions which promote DNA hybridization, for example, 6.0×sodium chloride/sodium citrate (SSC) at about 45° C., followed by a wash of 2.0×SSC at 50° C. are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C. to high stringency conditions, at about 65° C.

Isolated nucleic acids encoding a protein having the biological activity of MRP, as described herein, and having a sequence which differs from a nucleotide sequence shown in SEQ ID NO: 1 due to degeneracy in the genetic code are also within the scope of the invention. Such nucleic acids encode functionally equivalent proteins (e.g., a protein having MRP activity) but differ in sequence from the sequence of SEQ ID NO: 1 due to degeneracy in the genetic code. For example, a number of amino acids are designated by more than one triplet. Codons that specify the same amino acid, or synonyms (for example, CAU and CAC are synonyms for histidine) may occur due to degeneracy in the genetic code. As one example, DNA sequence polymorphisms within the nucleotide sequence of an MRP protein (especially those within the third base of a codon) may result in "silent" mutations in the DNA which do not affect the amino acid encoded. However, it is expected that DNA sequence polymorphisms that do lead to changes in the amino acid sequences of an MRP protein will exist within a population. It will be appreciated by one skilled in the art that these variations in one or more nucleotides (up to about 3–4% of the nucleotides) of the nucleic acids encoding proteins having the biological activity of MRP may exist among individuals within a population due to natural allelic variation. Any and all such nucleotide variations and resulting amino acid polymorphisms are within the scope of the invention. Furthermore, there may be one or more isoforms or related, cross-reacting family members of MRP described herein. Such isoforms or family members are defined as proteins related in biological activity and amino acid sequence to MRP, but encoded by genes at different loci.

An isolated nucleic acid of the present invention encoding a protein having the biological activity of MRP can be isolated from a multidrug resistant cell line which displays resistance to such drugs as anthracyclines, epipodophyllotoxins and Vinca alkaloids that is not substantially reversed by chemosensitizers which reverse P-glycoprotein-mediated multidrug resistance, such as verapamil or cyclosporin A. One example of such a cell line is H69AR. Other suitable cell lines can be produced by stepwise selection of a non-resistant cell line in the presence of increasing concentrations of a drug for which resistance is to be acquired over a period of several months to years. For example, a cell line is cultured in the presence of an anthracycline, preferably doxorubicin, for about 14 months. Multidrug resistance is then assessed by exposing the selected cell line to other drugs, e.g. an epipodo-phyllotoxin such as VP-16 and a Vinca alkaloid such as vincristine, and determining the cytotoxicity of the drug for the cell line. The ability of chemosensitizers which reverse P-glycoprotein-mediated multidrug resistance, such as verapamil and cyclosporin A, to reverse the multidrug resistance is then assessed by exposing the selected cell line to these agents in the presence of the resistant drugs. A detailed description of the procedures which can be used to produce appropriate multidrug resistant cell line such as H69AR is found in Cole, *Cancer Chemother Pharmacol.* 17, 259–263 (1986), Mirski et al., *Cancer Research* 47, 2594–2598 (1987) and Cole, et al. *British J. Cancer* 9:42–46 (1989).

An appropriate multidrug resistant cell line (e.g. a multidrug resistant cell line which displays resistance to anthracyclines, epipodophyllotoxins and Vinca alkaloids that is not substantially reversed by verapamil or cyclosporin A) is used to isolate a nucleic acid of the invention by preparing a cDNA library from this cell line by standard techniques and screening this library with cDNA produced from total mRNA isolated from the multidrug resistant cell line and its drug sensitive parental cell line. For example, a cDNA library constructed from total mRNA from H69AR cells is prepared. The library is plated and two sets of replica filters are prepared by standard methods. One set of filters is then screened with cDNA prepared from H69AR mRNA and the other set of filters is screened with a comparable amount of cDNA prepared from H69 mRNA. The cDNA used for screening the library is labelled, typically with a radioactive label. Following visualization of the hybridization results by standard procedures, cDNA clones displaying increased hybridization with H69AR cDNA when compared to H69 cDNA can be selected from the library. These cDNAs are derived from mRNAs overexpressed in H69AR cells when compared with H69 cells. For descriptions of differential cDNA library screening see King, C. R., et al. *J. Biol. Chem.* 254, 6781 (1979); Van der Bliek, A. M., et al., *Mol. Cell. Biol.* 6, 1671 (1986).

Determination of whether a cDNA so isolated has the biological activity of MRP can be accomplished by expressing the cDNA in a nonresistant mammalian cell, by standard techniques, and assessing whether expression in the cell of the protein encoded by the cDNA confers on the cell multidrug resistance to anthracyclines, epipodophyllotoxins and Vinca alkaloids that is not substantially reversed by verapamil or cyclosporin A. A cDNA having the biological activity of MRP so isolated can be sequenced by standard techniques, such as dideoxynucleotide chain termination or Maxam-Gilbert chemical sequencing, to determine the nucleic acid sequence and the predicted amino acid sequence of the encoded protein.

An isolated nucleic acid of the invention which is DNA can also be isolated by preparing a labelled nucleic acid probe encompassing all or part of the nucleotide sequence shown in SEQ ID NO: 1 and using this labelled nucleic acid probe to screen an appropriate DNA library (e.g. a cDNA or genomic DNA library). For instance, a cDNA library made from a multi-drug resistant cell line as described above can be used to isolate a cDNA encoding a protein having MRP activity by screening the library with the labelled probe using standard techniques. Preferably, an H69AR cDNA library is used. Alternatively, a genomic DNA library can be similarly screened to isolate a genomic clone encompassing a gene encoding a protein having MRP activity. As demonstrated in Example 4, a human MRP gene has been mapped to chromosome 16. Therefore, a chromosome 16 library rather than a total genomic DNA library can also be used to isolate a human MRP gene. Nucleic acids isolated by screening of a cDNA or genomic DNA library can be sequenced by standard techniques.

An isolated nucleic acid of the invention which is DNA can also be isolated by selectively amplifying a nucleic acid encoding a protein having MRP activity using the polymerase chain reaction (PCR) method and genomic DNA or mRNA. To prepare cDNA from mRNA, total cellular mRNA can be isolated, for instance from a multidrug resistant cell line, by a variety of techniques, e.g., by using the guanidinium-thiocyanate extraction procedure of Chirgwin et al., *Biochemistry*, 18, 5294–5299 (1979). cDNA is then synthesized from the mRNA using reverse transcriptase. Moloney MLV reverse transcriptase available from Gibco/BRL, Bethesda, Md., or AMV reverse transcriptase available from Seikagaku America, Inc., St. Petersburg, Fla., are preferably employed. It is possible to design synthetic oligonucleotide primers from the nucleotide sequence shown in SEQ ID NO: 1 for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis.

A isolated nucleic acid of the invention which is RNA can be isolated by cloning a cDNA of the invention into an appropriate vector which allows for transcription of the cDNA to produce an RNA molecule which encodes a protein having MRP activity. For example, a cDNA can be cloned downstream of a bacteriophage promoter, e.g. a T7 promoter, in a vector and the cDNA can be transcribed in vitro with T7 polymerase. A resultant RNA can be isolated by standard techniques.

A nucleic acid of the invention, for instance an oligonucleotide, can also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

Analysis of the nucleotide sequence of SEQ ID NO: 1 using currently available computer software designed for the purpose, such as PC/Gene—IntelliGenetics Inc., California, permits the identification of the initiation codon and untranslated sequences of an MRP cDNA. The cDNA coding strand, depicted as SEQ ID NO: 1, contains a 4593 nucleotide open reading frame encoding 1531 amino acids, as well as 195 5' untranslated nucleotides and 223 3' untranslated nucleotides. The intron-exon structure and the transcription regulatory sequences of the gene encoding the MRP cDNA can be identified by using a nucleic acid of the invention to probe a genomic DNA clone library. Regulatory elements, such as promoter and enhancers necessary for expression of the gene encoding the MRP in various tissues, can be identified using conventional techniques. The function of the elements can be confirmed by using them to express a reporter gene such as the bacterial gene lacZ which is operatively linked to the fragments. Such a construct can be introduced into cultured cells using standard procedures or into non-human transgenic animal models. In addition to identifying regulatory elements in DNA, such constructs can also be used to identify nuclear proteins interacting with said elements, using techniques known in the art.

A number of unique restriction sites for restriction enzymes are present in the nucleic acid comprising the nucleotide sequence shown in SEQ ID NO: 1 These restriction sites provide access to nucleotide fragments which code for polypeptides unique to the protein encoded by SEQ ID NO: 1 (i.e. a protein of the invention).

The isolated nucleic acids of the invention or oligonucleotide fragments of the isolated nucleic acids, allow those skilled in the art to construct nucleotide probes for use in the detection of nucleotide sequences in biological materials, such as tumor cell samples. A nucleotide probe can be labelled with a radioactive element which provides for an adequate signal as a means for detection and has sufficient half-life to be useful for detection, such as $^{32}P$, $^{3}H$, $^{14}C$ or the like. Other materials which can be used to label the probe include antigens that are recognized by a specific labelled antibody, fluorescent compounds, enzymes, antibodies specific for a labelled antigen, and chemiluminescent compounds. An appropriate label can be selected having regard to the rate of hybridization and binding of the probe to the nucleotide to be detected and the amount of nucleotide available for hybridization.

II. Antisense Nucleic Acids

The invention also relates to an antisense nucleic acid, or oligonucleotide fragment thereof, of a nucleic acid of the invention. An antisense nucleic acid can comprise a nucleotide sequence which is complementary to a coding strand of a nucleic acid, e.g. complementary to an mRNA sequence, constructed according to the rules of Watson and Crick base pairing, and can hydrogen bond to the coding strand of the nucleic acid. The antisense sequence complementary to a sequence of an mRNA can be complementary to a sequence found in the coding region of the mRNA or can be complementary to a 5' or 3' untranslated region of the mRNA. Furthermore, an antisense nucleic acid can be complementary in sequence to a regulatory region of the gene encoding the mRNA, for instance a transcription initiation sequence or regulatory element. Preferably, an antisense nucleic acid complementary to a region preceding or spanning the initiation codon or in the 3' untranslated region of an mRNA is used. An antisense nucleic acid can be designed based upon the nucleotide sequence shown in SEQ ID NO: 1. A nucleic acid is designed which has a sequence complementary to a sequence of the coding or untranslated region of the shown nucleic acid. Alternatively, an antisense nucleic acid can be designed based upon sequences of an MRP gene, identified by screening a genomic library as described above. For example, the sequence of an important regulatory element can be determined as described above and a sequence which is antisense to the regulatory element can be designed.

The antisense nucleic acids and oligonucleotides of the invention can be constructed using chemical synthesis and enzymatic ligation reactions using procedures known in the art. The antisense nucleic acid or oligonucleotide can be chemically synthesized using naturally occurring nucleotides or variously modified nucleotides designed to increase the biological stability of the molecules or to increase the physical stability of the duplex formed between the antisense and sense nucleic acids e.g. phosphorothioate derivatives and acridine substituted nucleotides can be used. Alternatively, the antisense nucleic acids and oligonucleotides can be produced biologically using an expression vector into which a nucleic acid has been subcloned in an antisense orientation (i.e. nucleic acid transcribed from the inserted nucleic acid will be of an antisense orientation to a target nucleic acid of interest). The antisense expression vector is introduced into cells in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

III. Recombinant Expression Vectors

The nucleic acids of the present invention which encode proteins having MRP activity can be incorporated in a known manner into a recombinant expression vector which ensures good expression of the encoded protein or part thereof. The recombinant expression vectors are "suitable for transformation of a host cell", which means that the recombinant expression vectors contain a nucleic acid or an oligonucleotide fragment thereof of the invention and a regulatory sequence, selected on the basis of the host cells to be used for expression, which is operatively linked to the nucleic acid or oligonucleotide fragment. Operatively linked is intended to mean that the nucleic acid is linked to a regulatory sequence in a manner which allows expression of the nucleic acid. Regulatory sequences are art-recognized and are selected to direct expression of the desired protein in an appropriate host cell. Accordingly, the term regulatory sequence includes promoters, enhancers and other expression control elements. Such regulatory sequences are known to those skilled in the art or one described in Goeddel, *Gene Expression Technology: Methods in Enzymology* 185, Academic Press, San Diego, Calif. (1990) can be used. It should be understood that the design of the expression vector may depend on such factors as the choice of the host cell to be transfected and/or the type of protein desired to be expressed. Such expression vectors can be used to transfect cells to thereby produce proteins or peptides encoded by nucleic acids as described herein.

The recombinant expression vectors of the invention can be designed for expression of encoded proteins in prokaryotic or eukaryotic cells. For example, proteins can be expressed in bacterial cells such as *E. coli*, insect cells (using baculovirus), yeast cells or mammalian cells. Other suitable host cells can be found in Goeddel, *Gene Expression Technology: Methods in Enzymology* 185, Academic Press, San Diego, Calif. (1990).

Expression in prokaryotes is most often carried out in *E. coli* with vectors containing constitutive or inducible promoters directing the expression of either fusion or non-fusion proteins. Fusion vectors add a number of amino acids usually to the amino terminus of the expressed target gene. Such fusion vectors typically serve three purposes: 1) to increase expression of recombinant protein; 2) to increase the solubility of the target recombinant protein; and 3) to aid in the purification of the target recombinant protein by acting as a ligand in affinity purification. Often, in fusion expression vectors, a proteolytic cleavage site is introduced at the junction of the fusion moiety and the target recombinant protein to enable separation of the target recombinant protein from the fusion moiety subsequent to purification of the fusion protein. Such enzymes, and their cognate recognition sequences, include Factor Xa, thrombin and enterokinase. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase, maltose E binding protein, or protein A, respectively, to the target recombinant protein.

Inducible non-fusion expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). While target gene expression relies on host RNA polymerase transcription from the hybrid trp-lac fusion promoter in pTrc, expression of target genes inserted into pET 11d relies on transcription from the T7 gn10-lac 0 fusion promoter mediated by coexpressed viral RNA polymerase (T7 gn1). This viral polymerase is supplied by host strains BL21(DE3) or HMS174(DE3) from a resident λ prophage harboring a T7 gn1 under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector (e.g. a nucleic acid encoding an MRP protein) so that the individual codons for each amino acid would be those preferentially utilized in highly expressed *E. coli* proteins (Wada et al., (1992) *Nuc. Acids Res.* 20:2111–2118). Such alteration of nucleic acid sequences of the invention could be carried out by standard DNA synthesis techniques.

Examples of vectors for expression in yeast *S. cerivisae* include pYepSecl (Baldari. et al., (1987) *Embo J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.).

Baculovirus vectors available for expression of proteins in cultured insect cells (SF 9 cells) include the pAc series (Smith et al., (1983) *Mol. Cell Biol.* 3:2156–2165) and the pVL series (Lucklow, V. A., and Summers, M. D., (1989) *Virology* 170:31–39).

Expression of an MRP protein in mammalian cells is accomplished using a mammalian expression vector. Examples of mammalian expression vectors include pCDM8 (Seed, B., (1987) *Nature* 329:840) and pMT2PC (Kaufman et al. (1987), *EMBO J.* 6:187–195). When used in mammalian cells, the expression vector's control functions are often provided by viral material. For example, commonly used promoters are derived from polyoma, Adenovirus 2, cytomegalovirus and most frequently, Simian Virus 40. Preferably, the pRc/CMV expression vector (Invitrogen) is used. In the pRc/CMV vector, nucleic acid introduced into the vector to be expressed is under the control of the enhancer/promoter sequence from the immediate early gene of human cytomegalovirus. Additionally, a gene conferring neomycin resistance is encoded by the vector. In one embodiment, the recombinant expression vector is capable of directing expression of the nucleic acid preferentially in a particular cell type. This means that the expression vector's control functions are provided by regulatory sequences which allow for preferential expression of a nucleic acid contained in the vector in a particular cell type, thereby allowing for tissue or cell-type specific expression of an encoded protein. For example, a nucleic acid encoding a protein with MRP activity can be preferentially expressed in cardiac muscle cells using promoter and enhancer sequences from a gene which is expressed preferentially in cardiac muscle cells, such as a cardiac myosin gene or a cardiac actin gene.

The recombinant expression vector of the invention can be a plasmid. The recombinant expression vector of the invention further can be a virus, or portion thereof, which allows for expression of a nucleic acid introduced into the viral nucleic acid. For example, replication defective retroviruses, adenoviruses and adeno-associated viruses can be used.

The invention further provides a recombinant expression vector comprising a DNA molecule of the invention cloned into the expression vector in an antisense orientation. That is, the DNA molecule is operatively linked to a regulatory sequence in a manner which allows for expression, by transcription of the DNA molecule, of an RNA molecule which is antisense to the nucleotide sequence of SEQ ID NO: 1. Regulatory sequences operatively linked to the antisense nucleic acid can be chosen which direct the continuous expression of the antisense RNA molecule in a variety of cell types, for instance a viral promoter and/or enhancer, or regulatory sequences can be chosen which direct tissue or cell type specific expression of antisense RNA, as described above.

IV. Transformant Host Cells

The recombinant expression vectors of the invention can be used to make a transformant host cell including the recombinant expression vector. The term "transformant host cell" is intended to include prokaryotic and eukaryotic cell which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (*Molecular Cloning: A Laboratory Manual*, 2nd Edition, Cold Spring Harbor Laboratory press (1989)), and other laboratory textbooks.

The number of host cells transformed with a recombinant expression vector of the invention by techniques such as those described above will depend upon the type of recombinant expression vector used and the type of transformation technique used. Plasmid vectors introduced into mammalian cells are integrated into host cell DNA at only a low frequency. In order to identify these integrants, a gene that contains a selectable marker (i.e., resistance to antibiotics) is generally introduced into the host cells along with the gene of interest. Preferred selectable markers include those which confer resistance to certain drugs, such as G418 and hygromycin. Selectable markers can be introduced on a separate plasmid from the nucleic acid of interest or, preferably, are introduced on a the same plasmid. Host cells transformed with a one or more recombinant expression vectors containing a nucleic acid of the invention and a gene for a selectable marker can be identified by selecting for cells using the selectable marker. For example, if the selectable marker encoded a gene conferring neomycin resistance (such as pRc/CMV), transformant cells can be selected with G418. Cells that have incorporated the selectable marker gene will survive, while the other cells die.

As demonstrated in Examples 5 and 6, the nucleic acids of the invention can confer multidrug resistance to drugs including anthracyclines, epipodophyllotoxins and Vinca alkaloids on a drug sensitive cell when transfected into the cell. Thus, these drugs can be used as selecting agents when preparing a transformant host cell rather than using an independent selectable marker (such as neomycin resistance). Therefore, the nucleic acids of the invention are useful not only for conferring multidrug resistance on a cell but also as selectable markers for cells into which the nucleic acid has been introduced. See for example Pastan et al. U.S. Pat. No. 5,166, 059; Croop et al. U.S. Pat. No. 5,198,344. Cells are selected by exposure to one or more drugs for which resistance is conferred by the nucleic acid. An MRP-encoding nucleic acid in a recombinant expression vector can be introduced into a cell together with a second nucleic acid comprising a gene of interest, either in the same vector or in separate vectors, and transformant cells can be selected based upon their acquired drug resistance. Drug resistant cells which are selected will contain the MRP-encoding nucleic acid often cointegrated with the gene of interest. Furthermore, by increasing stepwise the concentration of drug used in selecting the cells, it is possible to obtain transformant cells with a higher number of copies of the introduced nucleic acid, including both the MRP-encoding nucleic acid and a gene of interest. Therefore, the nucleic acids of the invention are also useful as amplifiable markers.

The nucleic acids of the invention encode proteins "having biological activity of MRP". The biological activity of MRP is defined as the ability of the protein, when expressed in a drug sensitive mammalian cell, to confer on the cell multidrug resistance to such drugs as anthracyclines, epipodophyllotoxins and Vinca alkaloids that is not substantially reversed by chemosensitizers which reverse P-glycoprotein-mediated multidrug resistance, such as verapamil or cyclosporin A. An isolated nucleic acid of the invention can be tested for MRP activity by incorporating the nucleic acid into a recombinant expression vector of the invention, transforming a drug sensitive mammalian cell with the recombinant expression vector to make a transformant host cell of the invention as described above and testing the multidrug resistance of the transformant host cell. The multidrug resistance of the transformant host cell is tested by determining the cytotoxicity of the drugs to be tested (i.e. anthracyclines, epipodophyllotoxins and Vinca alkaloids) for the transformed cell as compared to the untransformed cell, and the ability of other drugs (i.e. verapamil and cyclosporin A) to reverse multidrug resistance. For example, in a preferred embodiment, the transformant host cell is a HeLa cell, and the multidrug resistance of transfected HeLa cells is compared to that of untransfected HeLa cells or preferably to HeLa cells transfected with the parental expression vector lacking the nucleic acid encoding a protein having MRP activity.

V. Isolated Proteins

The invention provides isolated proteins having biological activity of MRP. The term "isolated" refers to a protein substantially free of cellular material or culture medium when produced by recombinant DNA techniques, or chemical precursors or other chemicals when chemically synthesized. In a preferred embodiment the protein having biological activity of MRP comprises an amino acid sequence shown in SEQ ID NO: 2. Alternatively, the protein can be encoded by a nucleic acid comprising the nucleotide sequence of SEQ ID NO: 1. Proteins having biological activity of MRP which have substantial sequence homology to the amino acid sequence of SEQ ID NO: 2, as defined above, are also encompassed by the invention. Furthermore, proteins having biological activity of MRP that are encoded by nucleic acids which hybridize under high or low stringency conditions, as defined above, to a nucleic acid comprising a nucleotide sequence shown in SEQ ID NO: 1 are encompassed by the invention. Additionally, immunogenic portions of MRP proteins are within the scope of the invention. As demonstrated in Example 7, two immunogenic portions of a protein comprising an amino acid sequence shown in SEQ ID NO: 2 correspond to amino acid residues 932–943 shown in SEQ ID NO: 2 (residues AELQKAEAKKEE) and amino acid residues 1427–1441 (residues GENLSVGQRQLVCLA). Two other immunogenic portions correspond to amino acid residues 243–252 shown in SEQ ID NO: 2 (residues SLNKEDTSEQ) and amino acid residues 765–779 (residues GVNLSGGQKQRVSLA). Preferred immunogenic portions correspond to regions of the protein not conserved in other ABC superfamily members, i.e. outside of the two NBF domains (amino acid residues 661–810 and 1310–1469), and include regions between the 12 membrane spanning regions. An immunogenic portion will be of at least about eight amino acids in length. See Almquist et al. *Cancer Research* 55:102–110 (1995).

The MRP protein, or isoforms or parts thereof, of the invention can be isolated by expression in a suitable host cell using techniques known in the art. Suitable host cells include prokaryotic or eukaryotic organisms or cell lines, for example, yeast, *E. coli* and insect cells. The recombinant expression vectors of the invention, described above, can be used to express a protein having MRP activity in a host cell in order to isolate the protein. The invention provides a method of preparing an isolated protein of the invention comprising introducing into a host cell a recombinant nucleic acid encoding the protein, allowing the protein to be expressed in the host cell and isolating the protein. Preferably, the recombinant nucleic acid is a recombinant expression vector. Proteins can be isolated from a host cell expressing the protein according to standard procedures of the art, including ammonium sulfate precipitation, fractionation column chromatography (e.g. ion exchange, gel filtration, electrophoresis, affinity chromatography, etc.) and ultimately, crystallization (see generally, "Enzyme Purification and Related Techniques", *Methods in Enzymology*, 22, 233–577 (1971)).

Alternatively, the protein or parts thereof can be prepared by chemical synthesis using techniques well known in the chemistry of proteins such as solid phase synthesis (Merrifield, 1964, J. Am. Chem. Assoc. 85:2149–2154) or synthesis in homogeneous solution (Houbenweyl, 1987, Methods of Organic Chemistry, ed. E. Wansch, Vol. 15 I and II, Thieme, Stuttgart).

VI. Antibodies

The proteins of the invention, or portions thereof, can be used to prepare antibodies specific for the proteins. Antibodies can be prepared which bind a distinct epitope in an unconserved region of the protein. An unconserved region of the protein is one which does not have substantial sequence homology to other proteins, for example other members of the ABC superfamily of membrane transport proteins. For example, unconserved regions encompassing sequences between the twelve membrane spanning regions, excluding the NBF domains, can be used. Alternatively, a region from one of the two NBF domains can be used to prepare an antibody to a conserved region of an MRP protein. An antibody to a conserved region may be capable of reacting with other members of the ABC family of membrane transport proteins. Conventional methods can be used to prepare the antibodies. For example, by using a peptide of an MRP protein, polyclonal antisera and monoclonal antibodies can be made using standard methods. As demonstrated in Example 7, a mammal, (e.g., a mouse, hamster, or rabbit) can be immunized with an immunogenic form of the peptide which elicits an antibody response in the mammal. Alternatively, polyclonal antisera and monoclonal antibodies can made by immunizing an animal with a cell which expresses MRP or by immunizing with a membrane fraction of an MRP expressing cell. As demonstrated in Example 8, a mammal (e.g., a mouse, hamster, or rabbit) can be immunized with enriched membrane fractions of the H69AR cell line to elicit a polyclonal antibody response against antigens expressed by the membrane fractions, including MRP. Monoclonal antibodies can then be made by conventional techniques and a monoclonal antibody specific for an MRP protein can be selected, as described further in Example 8.

Two hybridomas, designated QCRL-1 and QCRL-3, producing monoclonal antibodies QCRL-1 and QCRL-3 described in further detail in Example 8, have been deposited with the American Type Culture Collection 10801 University Boulevard, Manassas, Va. 20110-2209 on Nov. 30, 1994, under the provisions of the Budapest Treaty and have been assigned accession numbers HB 11765 and HB 11766, respectively.

To generate suitable anti-MRP antibodies, the immunogen should contain an effective, immunogenic amount of an MRP peptide or protein, e.g., as a membrane-bound protein, isolated protein, recombinantly produced protein, synthetic peptide, or other suitable form of the immunogen. The immunogen can optionally be used as a conjugate linked to a carrier. The effective amount of immunogen per unit dose depends, among other things, on the species of animal inoculated, the body weight of the animal and the chosen immunization regimen, as is well known in the art. An immunization preparation can also include an adjuvant as part of the diluent. Adjuvants such as complete Freund's adjuvant (CFA), incomplete Freund's adjuvant (IFA) and alum are materials well known in the art, and are available commercially from several sources. Techniques for conferring immunogenicity on a peptide include conjugation to a carrier. The progress of immunization can be monitored by detection of antibody titers in plasma or serum. Standard ELISA or other immunoassay can be used with the immunogen as antigen to assess the level of antibody titers. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein (*Nature* 256, 495–497 (1975)) as well as other techniques such as the human B-cell hybridoma technique (Kozbor et al., *Immunol. Today* 4, 72 (1983)), the EBV-hybridoma technique to produce human monoclonal antibodies (Cole et al. *Monoclonal Antibodies in Cancer Therapy* (1985) Allen R. Bliss, Inc., pages 77–96), and screening of combinatorial antibody libraries (Huse et al., *Science* 246, 1275 (1989)). Hybridoma cells can be screened immunochemically for production of antibodies specifically reactive with an MRP protein or peptide and monoclonal antibodies isolated by standard techniques (see Example 8).

The term antibody as used herein is intended to include fragments thereof which are also specifically reactive with a protein, or peptide thereof, having the biological activity of MRP. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments.

When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing an immunoglobulin variable region which recognizes an MRP protein of the invention. See, for example, Morrison et al., *Proc. Natl. Acad. Sci. U.S.A.* 81, 6851 (1985); Takeda et al., *Nature* 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B. It is expected that such chimeric antibodies would be less immunogenic in a human subject than the corresponding non-chimeric antibody.

For human therapeutic purposes, the monoclonal or chimeric antibodies specifically reactive with a protein, or peptide thereof, having the biological activity of a MRP as described herein can be further humanized by producing human variable region chimeras, in which parts of the variable regions, especially the conserved framework regions of the antigen-binding domain, are of human origin and only the hypervariable regions are of non-human origin. Such altered immunoglobulin molecules, referred to herein as "humanized" antibodies, may be made by any of several techniques known in the art, (e.g., Teng et al., *Proc. Natl. Acad. Sci. U.S.A.*, 80, 7308–7312 (1983); Kozbor et al., *Immunology Today*, 4, 7279 (1983); Olsson et al., *Meth. Enzymol.*, 92, 3–16 (1982)), and are preferably made according to the teachings of PCT Publication WO92/06193 or EP 0239400. Humanized antibodies can be commercially produced by, for example, Scotgen Limited, 2 Holly Road, Twickenham, Middlesex, Great Britain. Humanized antibodies which have reduced immunogenicity are preferred for immunotherapy in human subjects. Immunotherapy with a humanized antibody will likely reduce the necessity for any concomitant immunosuppression and may result in increased long term effectiveness for the treatment of chronic disease situations or situations requiring repeated antibody treatments.

Another method of generating specific antibodies, or antibody fragments, reactive against protein, or peptide thereof, having the biological activity of a MRP is to screen expression libraries encoding immunoglobulin genes, or portions thereof, expressed in bacteria with peptides produced from the nucleic acid molecules of the present invention. For example, complete Fab fragments, $V_H$ regions, $V_L$ regions, and $F_V$ regions can be expressed in bacteria using phage expression libraries. See for example Ward et al., *Nature* 341, 544–546: (1989); Huse et al., *Science* 246, 1275–1281 (1989); and McCafferty et al. *Nature* 348, 552–554 (1990). To identify an anti-MRP antibody, or antibody fragment, such libraries can be screened with an MRP protein of the invention, or peptide thereof. Alternatively, the SCID-hu mouse available from Genpharm can be used to produce antibodies, or fragments thereof.

The polyclonal, monoclonal or chimeric monoclonal antibodies can be used to detect the proteins of the invention, portions thereof or closely related isoforms in various biological materials, for example they can be used in an ELISA, radioimmunoassay or histochemical tests. Thus, the antibodies can be used to quantify the amount of an MRP protein of the invention, portions thereof or closely related isoforms in a sample in order to diagnose multidrug resistance, and to determine the role of MRP proteins in particular cellular events or pathological states, particularly its role in multidrug resistance. Using methods described hereinbefore, polyclonal, monoclonal antibodies, or chimeric monoclonal antibodies can be raised to nonconserved regions of MRP and used to distinguish MRP from closely related isoforms and other proteins that share a common conserved epitope.

The polyclonal or monoclonal antibodies can be coupled to a detectable substance. The term "coupled" is used to mean that the detectable substance is physically linked to the antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic-group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$ or $^{3}H$.

The present invention allows the skilled artisan to prepare bispecific antibodies and tetrameric antibody complexes. Bispecific antibodies can be prepared by forming hybrid hybridomas. The hybrid hybridomas can be prepared using the procedures known in the art such as those disclosed in Staerz & Bevan, (PNAS (USA) 83: 1453, 1986 and Immunology Today, 7:241, 1986). In general, a hybrid hybridoma is formed by fusing a first cell line which produces a first monoclonal antibody which is capable of binding to a tumor cell expressing a protein of the invention and a second cell line which produces a second monoclonal antibody which is capable of binding to a detectable substance, or a substance having toxic or therapeutic activity. The bispecific antibodies can also be constructed by chemical means using procedures such as those described by Staerz et al., (Nature, 314:628, 1985) and Perez et al., (Nature 316:354, 1985).

Bispecific monoclonal antibodies containing a variable region of an antibody, preferably a human antibody, specific for an MRP protein of the invention or portion thereof, a variable region of an antibody which is capable of binding to a detectable substance, or a substance having toxic or therapeutic activity and the constant regions of human immunoglobulins such as human IgG1, IgG2, IgG3 and IgG4 can also be constructed as described above. Bispecific chimeric monoclonal antibodies can also be constructed as described above.

A tetrameric antibody complex can be prepared by preparing a first monoclonal antibody which is capable of binding to a tumor cell expressing a protein of the invention and a second monoclonal antibody which is capable of binding to a detectable substance or a substance having toxic or therapeutic activity. The first and second antibody are from a first animal species. The first and second antibody are reacted with an about equimolar amount of antibodies of a second animal species or Fab fragments thereof, which are directed against the Fc-fragments of the antibodies of the first animal species. The tetrameric complex formed is then isolated. (See U.S. Pat. No. 4,868,109 to Lansdorp for a description of methods for preparing tetrameric antibody complexes).

Examples of detectable substances are enzymes, such as horseradish peroxidase, alkaline phosphatase, glucose oxidase and galactosidase. Examples of substances having toxic activity are cytotoxic cells such as macrophages, neutrophils, eosinophils, NK cells, LAK cells, and large granular lymphocytes or substances which are toxic to tumor cells such as radionuclides, and toxins such as diptheria toxin and ricin or attenuated derivatives thereof It will be appreciated that the antibody can be directed against the Fc receptor on cytotoxic cells. Examples of substances having therapeutic activity are chemotherapeutic agents such as carboplatin and methotrexate. Preferably, the chemotherapeutic agent is not a drug to which a protein having MRP activity confers resistance.

The antibodies, bispecific antibodies and tetrameric antibody complexes of the invention directed against a protein having MRP activity, optionally coupled with a substance having toxic or therapeutic activity, can be used to treat multidrug resistant tumors. Accordingly, the invention provides a composition comprising antibodies, bispecific antibodies or tetrameric antibody complexes in a pharmaceutically acceptable carrier. Preferably, the antibodies, bispecific antibodies or tetrameric antibody complexes are coupled to or capable of binding to a substance having toxic or therapeutic activity and to a tumor cell expressing a protein of the invention.

The compositions of the invention are administered to subjects in a biologically compatible form suitable for pharmaceutical administration in vivo. By "biologically compatible form suitable for administration in vivo" is meant a form of the antibody to be administered in which any toxic effects are outweighed by the therapeutic effects of the antibody. The term subject is intended to include living organisms in which an immune response can be elicited, e.g., mammals. Examples of subjects include humans, dogs, cats, mice, rats, and transgenic species thereof. Administration of a therapeutically active amount of the therapeutic compositions of the present invention is defined as an amount effective, at dosages and for periods of time necessary to achieve the desired result. For example, a therapeutically active amount of an antibody reactive with an MRP protein of the invention may vary according to factors such as the disease state, age, sex, and weight of the individual, and the ability of antibody to elicit a desired response in the individual. Dosage regima may be adjusted to provide the optimum therapeutic response. For example, several divided doses may be administered daily or the dose may be proportionally reduced as indicated by the exigencies of the therapeutic situation.

The active compound (e.g., antibody) may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound.

An antibody composition can be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions. To administer an antibody reactive with an MRP protein by other than parenteral administration, it may be necessary to coat the antibody with, or co-administer the antibody with, a material to prevent its inactivation. Enzyme inhibitors include pancreatic trypsin inhibitor, diisopropylfluorophosphate (DEP) and trasylol. Liposomes include water-in-oil-in-water emulsions as well as conventional liposomes (Strejan et al., (1984) *J. Neuroimmunol* 7:27). The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound (e.g., antibody reactive against an MRP protein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., antibody) plus any additional desired ingredient from a previously sterile-filtered solution thereof.

When the active compound is suitably protected, as described above, the composition may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the therapeutic treatment of individuals.

VII. Transgenic and Knockout Animals

Nucleic acids which encode proteins having biological activity of MRP can be used to generate either transgenic animals or "knock out" animals which, in turn, are useful in the development and screening of therapeutically useful reagents. A transgenic animal (e.g., a mouse) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, a human MRP cDNA, comprising the nucleotide sequence shown in SEQ ID NO: 1, or an appropriate sequence thereof, can be used to clone a murine MRP gene in accordance with established techniques and the genomic nucleic acid used to generate transgenic animals that contain cells which express MRP protein. Methods for generating transgenic animals, particularly animals such as mice, have become conventional in the art and are described, for example, in U.S. Pat. Nos. 4,736,866 and 4,870,009. In a preferred embodiment, plasmids containing recombinant molecules of the invention are microinjected into mouse embryos. In particular, the plasmids are microinjected into the male pronuclei of fertilized one-cell mouse eggs; the injected eggs are transferred to pseudo-pregnant foster females; and, the eggs in the foster females are allowed to develop to term. [Hogan, B. et al., (1986) A Laboratory Manual, Cold Spring Harbor, N.Y., Cold Spring Harbor Laboratory].

Alternatively, an embryonal stem cell line can be transfected with an expression vector containing nucleic acid encoding a protein having MRP activity and cells containing the nucleic acid can be used to form aggregation chimeras with embryos from a suitable recipient mouse strain. The chimeric embryos can then be implanted into a suitable pseudopregnant female mouse of the appropriate strain and the embryo brought to term. Progeny harbouring the transfected DNA in their germ cells can be used to breed uniformly transgenic mice.

Typically, particular cells would be targeted for MRP transgene incorporation by use of tissue specific enhancers operatively linked to the MRP-encoding gene. For example, promoters and/or enhancers which direct expression of a gene to which they are operatively linked preferentially in cardiac muscle cells can be used to create a transgenic animal which expresses an MRP protein preferentially in cardiac muscle tissue. Examples of suitable promoters and enhancers include those which regulate the expression of the genes for cardiac myosin and cardiac actin. Transgenic animals that include a copy of an MRP transgene introduced into the germ line of the animal at an embryonic stage can also be used to examine the effect of increased MRP expression in various tissues.

The pattern and extent of expression of a recombinant molecule of the invention in a transgenic mouse is facilitated by fusing a reporter gene to the recombinant molecule such that both genes are co-transcribed to form a polycistronic mRNA. The reporter gene can be introduced into the recombinant molecule using conventional methods such as those described in Sambrook et al., 1989, Molecular Cloning, A Laboratory Manual. Cold Spring Harbor Laboratory Press. Efficient expression of both cistrons of the polycistronic mRNA encoding the protein of the invention and the reporter protein can be achieved by inclusion of a known internal translational initiation sequence such as that present in poliovirus mRNA. The reporter gene should be under the control of the regulatory sequence of the recombinant molecule of the invention and the pattern and extent of expression of the gene encoding a protein of the invention can accordingly be determined by assaying for the phenotype of the reporter gene. Preferably the reporter gene codes for a phenotype not displayed by the host cell and the phenotype can be assayed quantitatively. Examples of suitable reporter genes include lacZ (B-galactosidase), neo (neomycin phosphotransferase), CAT (chloramphenicol acetyltransferase) dhfr (dihydrofolate reductase), aphIV (hygromycin phosphotransferase), lux (luciferase), uidA (B-glucuronidase). Preferably, the reporter gene is lacZ which codes for B-galactosidase. B-galactosidase can be assayed using the lactose analogue X-gal(5-bromo-4-chloro-3-indolyl-b-D-galactopyranoside) which is broken down by B-galactosidase to a product that is blue in color. (See for example Old R. W. & Primrose S. B., Principles of Gene Manipulation. An Introduction to Genetic Engineering, 4th ed. Oxford University Press at pages 63–66 for a discussion of procedures for screening for recombinants).

Although experimental animals used in the preferred embodiment disclosed are mice, the invention should not be limited thereto. It can be desirable to use other species such as rats, hamsters and rabbits.

The transgenic animals of the invention can be used to investigate the molecular basis of multidrug resistance. The transgenic animals of the invention can also be used to test substances for the ability to prevent, slow or reverse the development of multidrug resistance. A transgenic animal can be treated with the substance in parallel with an untreated control transgenic animal.

Cells from the transgenic animals of the invention can be cultured using standard tissue culture techniques. In particular, cells carrying the recombinant molecule of the invention can be cultured and used to test substances for the ability to prevent, slow or reverse multidrug resistance.

Additionally, the non-human homologues of genes encoding proteins having MRP activity can be used to construct an MRP "knock out" animal which has a defective or altered MRP gene. For example, a human MRP cDNA, comprising the nucleotide sequence shown in SEQ ID NO: 1, or an appropriate sequence thereof, can be used to clone a murine MRP gene in accordance with established techniques. A portion of the isolated genomic MRP DNA (e.g., an exon) can be deleted or replaced with another gene, such as a gene encoding a selectable marker which can be used to monitor integration. The altered MRP DNA can then be transfected into an embryonal stem cell line. The altered MRP DNA will homologously recombine with the endogenous MRP gene in certain cells and clones containing the altered gene can be selected. Cells containing the altered gene are injected into a blastocyst of an animal, such as a mouse, to form aggregation chimeras as described for transgenic animals. Chimeric embryos are implanted as described above. Transmission of the altered gene into the germline of a resultant animal can be confirmed using standard techniques and the animal can be used to breed animals having an altered MRP gene in every cell. Accordingly, a knockout animal can be made which cannot express a functional MRP protein. Such a knockout animal can be used, for example, to test the effectiveness of a chemotherapeutic agent in the absence of an MRP multidrug resistance protein.

VIII. Uses of the Invention

The isolated nucleic acids of the invention are useful as molecular probes for use diagnostically to determine multidrug resistance of a tumor. As demonstrated in Example 1, multidrug resistance of certain tumor cell lines is associated with increased expression of cellular mRNA corresponding to the nucleotide sequence of SEQ ID NO: 1. Accordingly, the nucleic acids of the invention can be labelled with a detectable marker, such as a radioactive, fluorescent or biotinylated marker, and used in conventional dot blot, Northern hybridization or in situ hybridization procedures to probe mRNA molecules of total cellular or poly(A)+ RNAs from a biological sample, for instance cells of a tumor biopsy.

The nucleic acid probes can be used to detect genes, preferably in human cells, that encode proteins related to or analogous to the MRP of the invention. Preferably, nucleic acid comprising the nucleotide sequence of the invention, or a segment thereof, can be used as a probe to identify DNA fragments comprising genes or parts of genes that are co-amplified with the gene of the invention and which reside within the same amplification unit, or amplicon, at the chromosomal location 16p 13.1. More specifically a nucleic acid of the invention can be used as a probe to screen human genomic DNA libraries constructed in cosmid or yeast artificial chromosome vectors, using procedures standard in the art, to define a contiguous segment of DNA that comprises the amplification unit detected in a multidrug resistant cell line such as H69AR. In this manner additional genes can be identified which also confer or contribute to the multidrug resistance phenotype of H69AR and other human cell lines yet to be examined but which are known to include the HeLa cell line J2c and HT1080 DR4 cell line.

The antisense nucleic acids of the invention are useful for inhibiting expression of nucleic acids (e.g. mRNAs) encoding proteins having MRP activity, thereby decreasing expression of proteins having MRP activity. Since increased expression of proteins having MRP activity is associated with and can confer multidrug resistance on a cell, decreasing expression of such proteins can inhibit or reverse multidrug resistance of a cell into which the antisense nucleic acid has been introduced. Antisense nucleic acids can be introduced into a multidrug resistant cell in culture to inhibit MRP expression. Qne or more antisense nucleic acids, such as oligonucleotides, can be added to cells in culture media, typically at 200 $\mu$g/ml. A cultured multidrug resistant cell in which MRP expression is inhibited is useful for testing the efficacy of potential therapeutic agents. For example, MRP expression could be inhibited in a tumor cell line which expresses both MRP and P-glycoprotein to determine the contribution of MRP to an observed resistance or sensitivity of the cell to a particular therapeutic agent.

The antisense nucleic acids of the invention, or oligonucleotides thereof, can also be used in gene therapy to correct or prevent multidrug resistance in a subject. For example, antisense sequences can be used to render multidrug resistant malignant cells sensitive to chemotherapeutic agents. Administration of antisense nucleic acids to a subject may be most effective when the antisense nucleic acid is contained in a recombinant expression vector which allows for continuous production of antisense RNA. Recombinant molecules comprising an antisense nucleic acid or oligonucleotides thereof, can be directly introduced into tissues, including lung tissue in vivo, using delivery vehicles such as liposomes, retroviral vectors, adenoviral vectors and DNA virus vectors. A delivery vehicle can be chosen which can be targeted to a cell of interest in the subject (e.g. a multidrug resistant tumor cell). Antisense nucleic acids can also be introduced into isolated cells, such as those of the hematopoietic system, ex vivo using viral vectors or physical techniques such as microinjection and electroporation or chemical methods such as coprecipitation and incorporation of DNA into liposomes and such cells can be returned to the donor. Recombinant molecules can also be delivered in the form of an aerosol or by lavage. In the treatment of lung malignancies, antisense sequences can be directly delivered to lung tissue by an aerosol or by lavage.

Accordingly, the invention provides a method for inhibiting multidrug resistance of a multidrug resistant cell by introducing into the multidrug resistant cell a nucleic acid which is antisense to a nucleic acid which encodes the protein shown in SEQ ID NO: 2.

The nucleic acids of the invention can further be used to design ribozymes which are capable of cleaving a single-stranded nucleic acid encoding a protein having MRP activity, such as an mRNA. A catalytic RNA (ribozyme) having ribonuclease activity can be designed which has specificity for an MRP-encoding mRNA based upon the sequence of a nucleic acid of the invention. For example, a derivative of a Tetrahymena L-19 IVS RNA can be constructed in which the base sequence of the active site is complementary to the base sequence to be cleaved in an MRP-encoding mRNA. See for example Cech et al. U.S. Pat. No. 4,987,071; Cech et al. U.S. Pat. No. 5,116,742. Alternatively, a nucleic acid ofthe invention could be used to select a catalytic RNA having a specific ribonuclease activity from a pool of RNA molecules. See for example Bartel, D. and Szostak, J. W. *Science* 261, 1411–1418 (1993).

The isolated nucleic acids and antisense nucleic acids of the invention can be used to construct recombinant expression vectors as described previously. These recombinant expression vectors are then useful for making transformant host cells containing the recombinant expression vectors, for expressing proteins encoded by the nucleic acids of the invention, and for isolating proteins of the invention as described previously. The isolated nucleic acids and antisense nucleic acids of the invention can also be used to construct transgenic and knockout animals as described previously.

As demonstrated in Examples 5 and 6, a recombinant expression vector containing a nucleic acid of the invention can be used to transfect a drug sensitive cell line to produce a protein in the cell which can confer multidrug resistance on the transfected cell line. Thus, the recombinant expression vectors of the invention are useful for conferring multidrug resistance on a drug sensitive cell. Accordingly, the invention provides a method for protecting a drug sensitive cell from cytotoxicity due to exposure to a drug by transfecting the cell with nucleic acid comprising a nucleotide sequence shown in SEQ ID NO: 1 to confer drug resistance on the cell. In preferred embodiments, the drug sensitive cell is a cardiac muscle cell or a hematopoietic stem cell. The ability to confer drug resistance on a cell has important clinical applications. A major dose-limiting factor for chemotherapeutic agents is their cytotoxicity for normal cells in a patient as well as tumor cells. In patients with multi-drug resistant tumors, increasing the dosage of chemotherapeutic agents is prohibited by the toxicity of these agents for normal cells. In the case of anthracyclines, cardiotoxicity of the drugs can be a major clinical limitation. For chemotherapeutic drugs which target rapidly dividing cells, toxicity to hematopoietic cells can be a major clinical limitation. Additionally, neurotoxicity can occur. Protecting nonresistant nontumor cells from the effects of chemotherapeutic agents, by conferring on the cell multidrug resistance, thus has major clinical importance.

The transformant host cells of the invention, and recombinant expression vectors used to make them, are useful for testing potential therapeutic agents for their effectiveness against multidrug resistant cells. These agents include agents which are themselves cytotoxic for multidrug resistant cells or which are chemosensitizers of other therapeutic agents. As used herein, the term "chemosensitizer" refers to a substance which can increase the efficacy of a therapeutic agent against a multidrug resistant cell and/or decrease the resistance of a multidrug resistant cell for a therapeutic agent.

A method is provided for identifying a chemosensitizer of a therapeutic agent. The method involves incubating the therapeutic agent with a cell transfected with a nucleic acid which confers resistance to the therapeutic agent on the cell, both with and without a substance to be tested, determining resistance of the cell to the therapeutic agent when incubated with and without the substance to be tested and identifying a substance which is a chemosensitizer of the therapeutic agent by the ability of the substance to decrease the resistance of the cell to the therapeutic agent when incubated with the substance as compared to the resistance of the cell to the therapeutic agent when incubated without the substance. In a preferred embodiment, the nucleic acid is a recombinant expression vector containing nucleic acid comprising a nucleotide sequence shown in SEQ ID NO: 1. Preferably, the cell into which the nucleic acid is transfected is drug sensitive prior to transfection so that the effects of a potential chemosensitizer are assessed in the presence of a single, isolated multidrug resistance-conferring protein. The cell used to test potential chemosensitizing substances can be a cell in culture, e.g. a transformant host cell of the invention, and the therapeutic agent and substance to be tested are incubated in culture with the cell. Alternatively, the cell can be a multidrug resistant cell in a transgenic animal, transgenic for a nucleic acid of the invention, and the therapeutic agent and substance to be tested are administered to the transgenic animal. Furthermore, the cell can be a cell in culture isolated from a multidrug resistant transgenic animal of the invention. The resistance of the cell for the therapeutic agent in the presence and absence of the potential therapeutic agent is assessed by determining the concentration of the therapeutic agent which is cytotoxic for the cell either in the presence or in the absence of the substance being tested.

The invention provides a method for identifying a substance which is directly cytotoxic to a multidrug resistant cell involving incubating a substance to be tested with a cell transfected with a nucleic acid which confers multidrug resistance on the cell and determining the cytotoxicity of the substance for the cell. In a preferred embodiment, the nucleic acid is a recombinant expression vector containing nucleic acid comprising a nucleotide sequence shown in SEQ ID NO: 1. Preferably, the cell into which the nucleic acid is transfected is drug sensitive prior to transfection so that the effects of a potential chemosensitizer are assessed in the presence of a single, isolated multidrug resistance-conferring protein. The cell used to test potential cytotoxic substances can be a cell in culture, e.g. a transformant host cell of the invention, and the substance to be tested is incubated in culture with the cell. Alternatively, the cell can be a multidrug resistant cell in a transgenic animal, transgenic for a nucleic acid of the invention and the substance to be tested is administered to the transgenic animal. Furthermore, the cell can be a cell in culture isolated from a multidrug resistant transgenic animal of the invention.

Additionally, a multidrug resistant cell line such as H69AR, or an equivalent cell line, can be used in the same methods for identifying a chemosensitizer of a therapeutic agent or for identifying a substance which is directly cytotoxic to a multidrug resistant cell.

The isolated proteins of the invention are useful for making antibodies reactive against proteins having MRP activity, as described previously. Alternatively, the antibodies of the invention can be used to isolate a protein of the invention by standard immunoaffinity techniques. Furthermore, the antibodies of the invention, including bispecific antibodies and tetrameric antibody complexes, are useful for diagnostic purposes and for therapeutic purposes.

In one embodiment of the invention, antibodies labelled with a detectable substance, such as a fluorescent marker, an enzyme or a radioactive marker, can be used to identify multidrug resistant tumor cells in a tumor sample or in vivo. Tumor tissue removed from a patient can be used as the tumor sample. In order to prevent tumor samples from being degraded, the samples can be stored at temperatures below $-20°$ C. A tissue section, for example, a freeze-dried or fresh frozen section of tumor tissue removed from a patient, can also be used as the tumor sample. The samples can be fixed and the appropriate method of fixation is chosen depending upon the type of labelling used for the antibodies. Alternatively, a cell membrane fraction can be separated from the tumor tissue removed from a patient and can be used as the tumor sample. Conventional methods such as differential or density gradient centrifugation can be used to separate out a membrane fraction.

A multidrug resistant tumor cell is identified by incubating an antibody of the invention, for example a monoclonal antibody, with a tumor cell to be tested for multidrug resistance. Binding of the antibody to the tumor cell is indicative of the presence on the tumor cell of a protein having MRP activity. The level of antibody binding to the tumor cell can be compared to the level of antibody binding to a normal control cell, and increased binding of the antibody to the tumor cell as compared to the normal cell can be used as an indicator of multidrug resistance. Binding of the antibody to a cell (e.g. a tumor cell to be tested or a normal control cell) can be determined by detecting a detectable substance with which the antibody is labelled. The detectable substance may be directly coupled to the antibody, or alternatively, the detectable substance may be coupled to another molecule which can bind the antibody. For example, an antibody of the invention which has a rabbit Fc region (e.g. which was prepared by immunization of a rabbit) can be detected using a second antibody directed against the rabbit Fc region, wherein the second antibody is coupled to a detectable substance.

A multidrug resistant tumor cell can be detected as described above in vitro in a tumor sample prepared as described above. For example, a tumor section on a microscope slide can be reacted with antibodies using standard immunohistochemistry techniques. Additionally, if a single cell suspension of tumor cells can be achieved, tumor cells can be reacted with antibody and analyzed by flow cytometry. Alternatively, a multidrug resistant tumor cell can be detected in vivo in a subject bearing a tumor. Labelled antibodies can be introduced into the subject and antibodies bound to the tumor can be detected. For example, the antibody can be labelled with a radioactive marker whose presence and location in a subject can be detected by standard imaging techniques.

The antibodies of the invention, and compositions thereof, can also be used to inhibit the multidrug resistance of a multidrug resistant cell. The invention provides a method for inhibiting the multidrug resistance of a multidrug resistant cell comprising inhibiting activity of a protein comprising an amino acid shown in SEQ ID NO: 2 expressed by the multidrug resistant cell. Preferably, the multidrug resistant cell is a tumor cell. In preferred embodiments, the molecule which binds to a protein comprising an amino acid sequence shown in SEQ ID NO: 2 is a monoclonal antibody, bispecific antibody or tetrameric immunological complex of the invention. Multidrug resistance can be inhibited by interfering with the MRP activity of the protein to which the molecule binds. For example, the ability of an MRP protein to transport drugs may be impaired. Accordingly, any molecule which binds to a protein having MRP activity and whose binding inhibits the MRP activity of the protein are encompassed by invention. Isolated proteins of the invention, comprising the amino acid sequence shown in SEQ ID NO: 2, can be used to identify molecules, including and in addition to the antibodies of the invention, which can bind to a protein having MRP activity in a standard binding assay. A multidrug resistant cell in which multidrug resistance is inhibited, by inhibiting the activity of an MRP protein, can further be treated with a therapeutic agent to which the cell is no longer resistant or less resistant due to inhibition of MRP activity in order to kill the cell.

Molecules which bind to a protein comprising an amino acid sequence shown in SEQ ID NO: 2 can also be used in a method for killing a multidrug resistant cell which expresses the protein. Preferably, the multidrug resistant cell is a tumor cell. Destruction of a multidrug resistant cells can be accomplished by labelling the molecule with a substance having toxic or therapeutic activity. The term "substance having toxic or therapeutic activity" as used herein is intended to include molecules whose action can destroy a cell, such as a radioactive isotope, a toxin (e.g. diptheria toxin or ricin), or a chemotherapeutic drug, as well as cells whose action can destroy a cell, such as a cytotoxic cell. The molecule binding to multidrug resistant cells can be directly coupled to a substance having toxic or therapeutic activity (e.g. a ricin-linked monoclonal antibody), or may be indirectly linked to the substance. For example, a bispecific antibody which is capable of crosslinking a tumor cell and a cytotoxic cell can be used, thereby facilitating lysis of the tumor cell. A bispecific antibody can crosslink a tumor cell and the cytotoxic cell by binding to the Fc receptors of cytotoxic cells.

The compositions and methods of the invention can be used to treat patients with tumors displaying multidrug resistance particularly those displaying resistance to anthracyclines, epipodophyllotoxins, vinca alkaloids, and hydrophobic drugs. The methods of the invention for inhibiting the multidrug resistance of a tumor cell and for killing a multidrug resistant tumor cell can be applied to patients having a multidrug resistant tumor. The compositions and methods can be particularly useful in treating breast cancer, leukemias, fibrosarcomas, cervical cancer, gliomas, thymomas, neuroblastomas and lung cancer, in particular small cell lung cancers and non small cell lung cancers.

The invention also provides a diagnostic kit for identifying multidrug resistant tumor cells comprising a molecule which binds to a protein comprising an amino acid sequence shown in SEQ ID NO: 2 for incubation with a sample of tumor cells; means for detecting the molecule bound to the protein, unreacted protein or unbound molecule; means for determining the amount of protein in the sample; and means for comparing the amount of protein in the sample with a standard. Preferably, the molecule is a monoclonal antibody. Other molecules which can bind a protein having MRP activity can be used, including the bispecific antibodies and tetrameric antibody complexes of the invention. The diagnostic kit can also contain an instruction manual for use of the kit.

The invention further provides a diagnostic kit for identifying multidrug resistant tumor cells comprising a nucleotide probe complementary to the sequence, or an oligonucleotide fragment thereof, shown in SEQ ID NO: 1 for hybridization with mRNA from a sample of tumor cells; means for detecting the nucleotide probe bound to mRNA; means for determining the amount of mRNA in the sample; and means for comparing the amount of mRNA in the sample with a standard. The diagnostic kit can also contain an instruction manual for use of the kit.

The invention is further illustrated by the following examples. However, the examples are merely intended to illustrate embodiments of the invention and are not to be construed to limit the scope of the invention. The contents of all references and published patents and patent applications cited throughout this application are hereby incorporated by reference.

EXAMPLE 1

ISOLATION OF cDNA SEQUENCES DERIVED FROM mRNAS OVEREXPRESSED IN H69AR CELLS

Figure 1A:
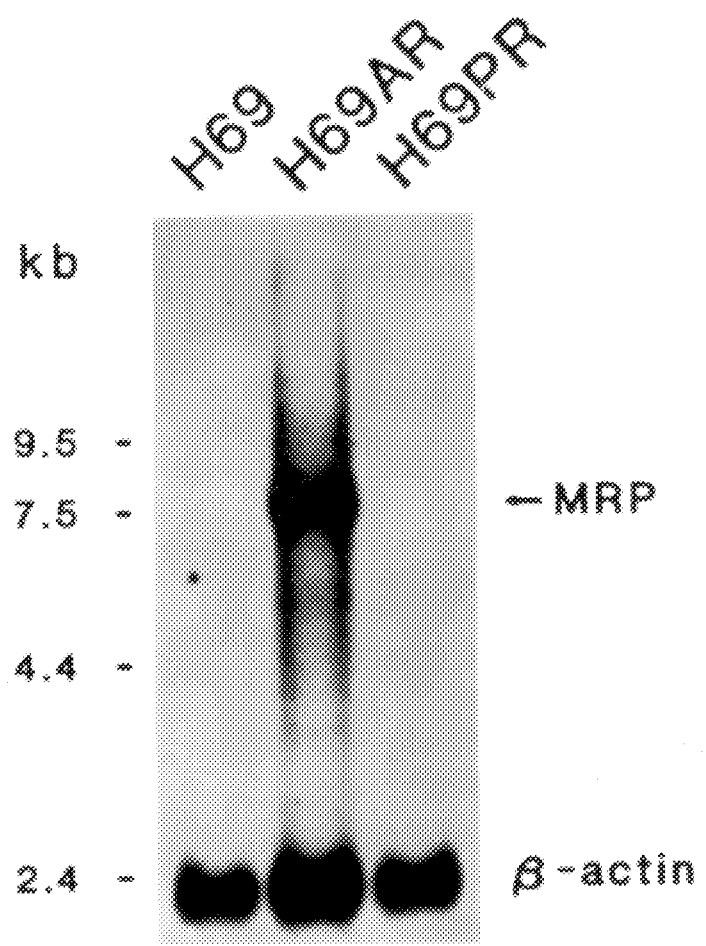
FIG. 1A is a Northern blot of poly(A$^+$)RNA from H69, H69AR and H69PR cells hybridized with a 1.8 kb EcoR1 cDNA fragment of the multidrug resistance protein of the invention.
Figure 1B:
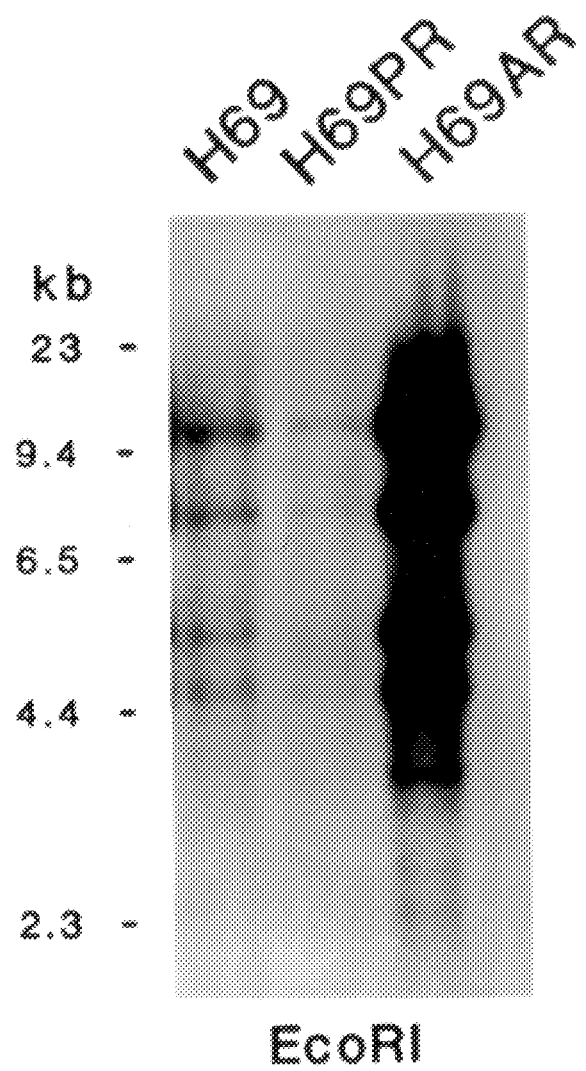
FIG. 1B is a Southern blot analysis of EcoRI—digested genomic DNA from H69, H69AR and H69PR cells hybridized with a 1.8 kb EcoR1 cDNA fragment of the multidrug resistance protein of the invention.

As part of a search of proteins responsible for the multidrug resistance displayed by H69AR cells, a randomly primed cDNA library constructed from H69AR mRNA was screened using differential hybridization with total cDNA prepared from H69 and H69AR mRNA. One of the clones isolated contained a 2.8 kb cDNA insert and gave a particularly strong differential signal when analyzed on northern blots (FIG. 1A). The analysis of 1 $\mu$g of poly(A$^+$)RNA from each cell line was carried out using standard procedures. Poly(A$^+$)RNA was obtained using a Fast Track™ mRNA isolation kit (Invitrogen) and 1 $\mu$g was electrophoresed on a denaturing formaldehyde agarose gel. The RNA was transferred to nitrocellulose membrane and prehybridized in 50% formamide, 5×SSPE(1×=150 mM NaCl, 10 mM NaH$_2$PO$_4$, 1 mM EDTA, pH 7.4), 2.5×Denhardt's solution (50×=1% bovine serum albumin, 1% polyvinylpyrrolidone, 1% ficoll) and sheared, denatured herring testes DNA (100 $\mu$g/ml) for 4–16 hours at 42° C. The blot was probed with a 1.8 kb EcoRI fragment of MRP, labelled to a specific activity of >5×10$^8$ cmp/$\mu$g DNA with $\alpha$-[$^{32}$P]-dCTP (3000 Ci/mmol; Dupont/NEN) by the random priming method [A. P. Feinberg, B. Vogelstein, Analyt. Biochem. 132, 6 (1983)]. Hybridization was carried out for 16–20 hours at 42° C. Blots were washed three times in 0.1% SDS and 0.1×SSC (pH 7.0) for 30 minutes each at 52° C. and then exposed to film. To estimate variation in RNA loading of the gel, the blot was reprobed with a $^{32}$P-labelled $\beta$-actin cDNA (201pBv2.2)[H. Ueyama, H. Hamada, N. Battula, T. Kakunaga, Mol. Cell. Biol. 4, 1073 (1984)]. The autoradiograph shown in FIG. 1A is a 5 hour exposure with intensifying screens at −70° C. The size of the overexpressed mRNA in H69AR cells was estimated to be approximately 7 kb. Prolonged exposure of the film revealed low levels of this mRNA in H69 and H69PR cells. The concentration of this mRNA was increased 100 fold in H69AR cells relative to H69 cells. The level of this mRNA in H69PR, a drug sensitive revertant of H69AR, had decreased approximately 20-fold relative to that found in H69AR, further substantiating the correlation of overexpression of this particular mRNA with a multidrug resistance phenotype. Southern blot analyses of H69, H69AR and H69PR DNA indicated that the major mechanism underlying overexpression was gene amplification. Ten $\mu$g of each DNA was digested with EcoRI, electrophoresed through a 0.7% agarose gel and blotted onto a nitrocellulose membrane. The DNA was hybridized with a 1.8 kb EcoRI cDNA fragment of MRP, labelled by random priming with $\alpha$-[$^{32}$P]-dCTP. The autoradiograph shown in FIG. 1B is a 6 hour exposure at $-70°$ C. Based on the examination of several restriction digests and normalization of the amounts of DNA loaded, the MRP gene was amplified 40–50 fold in resistant H69AR cells and no differences in the copy number of the gene in H69 and H69PR cells were detected.

Figure 1C:
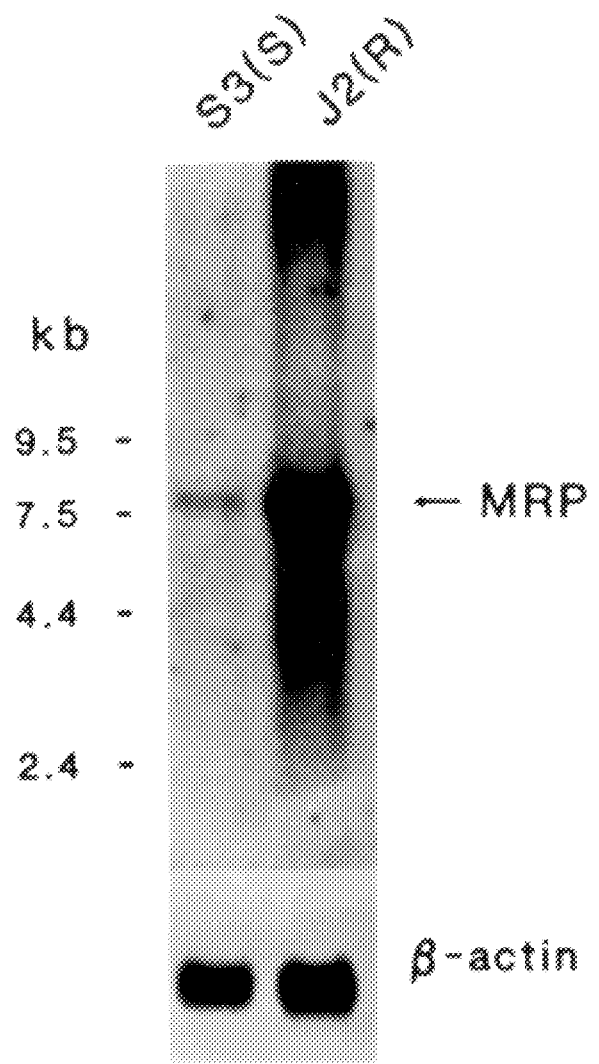
FIG. 1C is a Northern blot of sensitive and resistant HeLa cell poly (A$^+$)RNA hybridized with a 1.8 kb EcoRI cDNA fragment of the multidrug resistance protein of the invention.

The mRNA was also overexpressed 10–15 fold in a doxorubicin-selected multidrug resistant HeLa cell line that does not overexpress P-glycoprotein (FIG. 1C). S3 and J2c are drug sensitive and resistant HeLa cell lines obtained from the laboratory of Dr. R. M. Baker (Roswell Park Memorial Institute). Two $\mu$g of poly(A$^+$)RNA from each cell line was electrophoresed, blotted and probed with MRP cDNA as described for FIG. 1A. The MRP and $\beta$-actin autoradiographs shown in FIG. 1C are 18 hour and 1 hour exposures, respectively, at $-70°$ C. Southern blotting of DNA from S3 and J2c cells indicated that the MRP gene was amplified 10–15 fold in the resistant cell line. These findings provide further evidence of the association of elevated levels of this mRNA with multidrug resistance.

The initial 2.8 kb cDNA clone was sequenced, allowing the isolation of overlapping clones by rescreening the H69AR cDNA library with synthetic oligonucleotides. A single, extended open reading frame of 1531 amino acids was defined encoding a protein designated as multidrug resistance associated protein (MRP). The translated GenBank and SwissProt databases were searched for similarities to MRP using the FASTA program. The search revealed that MRP is a novel member of the ATP-binding cassette (ABC) superfamily of transport systems. Members of this superfamily are involved in the energy dependent transport of a wide variety of molecules across cell membranes in both eukaryotes and prokaryotes. Included in this superfamily are the human multidrug transporter P-glycoprotein (MDR1) and the cystic fibrosis transmembrane conductance regulator (CFTR).

EXAMPLE 2

RELATIONSHIP OF MRP TO OTHER MEMBERS OF THE ABC TRANSPORTER SUPERFAMILY

Figure 2:
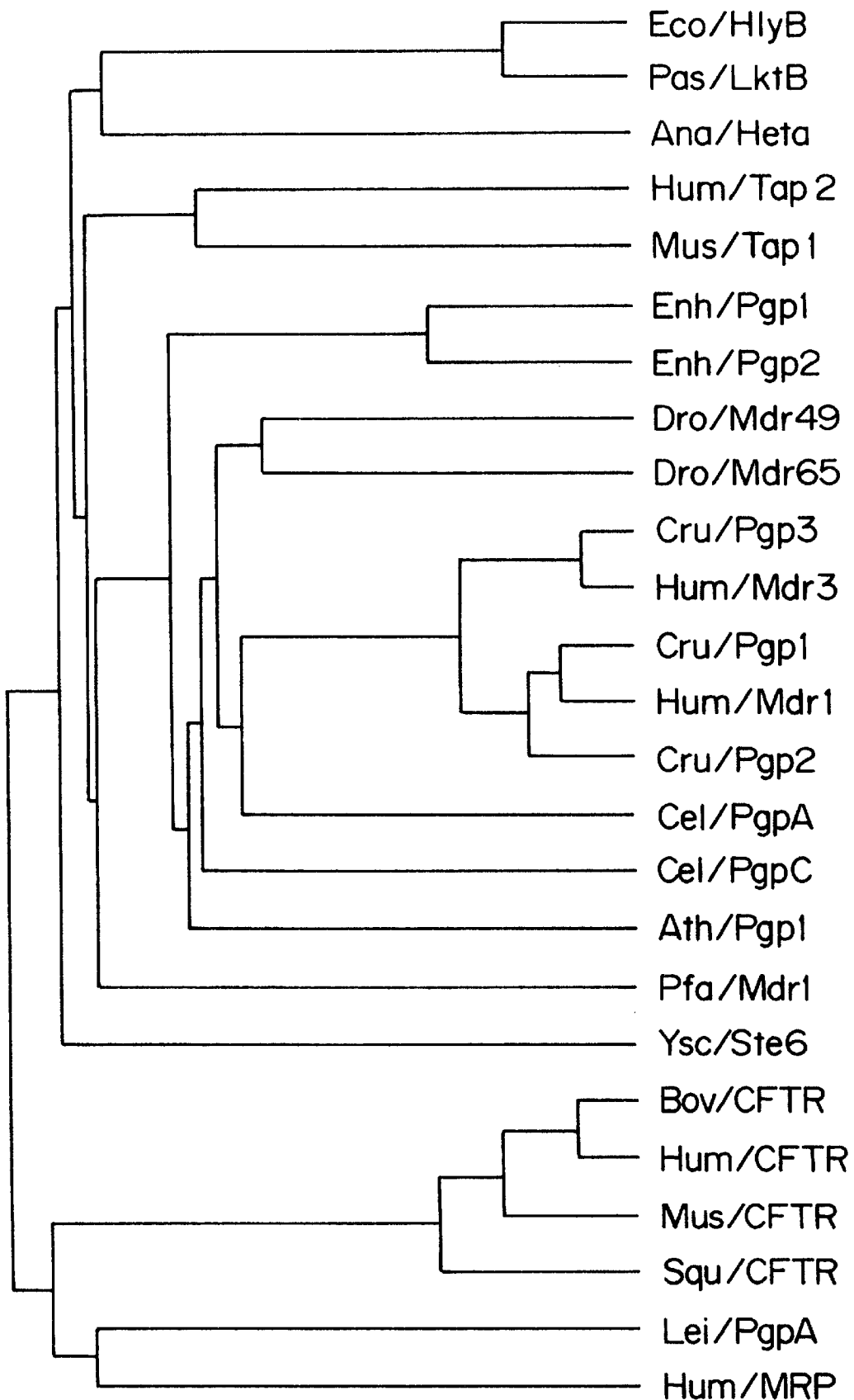
FIG. 2 is a cluster analysis of the relative similarity of the multidrug resistance protein of the invention to selected members of the ATP-binding cassette transporter superfamily that contain hydrophobic transmembrane regions followed by nucleotide binding folds.

The relationship of MRP to the various members of the ABC transporter superfamily was examined using the PILEUP program from the Genetics Computer Group package (version 7) using a modified version of the progressive alignment method of Feng and Doolittle [J. Mol. Evol. 25, 351 (1987)]. A representative selection of a phylogenetically broad range of ABC proteins that are comprised of hydrophobic transmembrane regions followed by nucleotide binding regions, and whose sequences could be retrieved from GenBank and SwissProt databases, were included in this analysis. The analysis divides this family of proteins into two major subgroups (FIG. 2). One of the major subgroups consists of the cluster containing MRP (Hum/MRP), the leishmania P-glycoprotein-related molecule (Lei/PgpA) and the CFTRs (Hum/CFTR, Bov/CFTR, Mus/CFTR and Squ/CFTR). The other subgroup consists of the P-glycoproteins, the MHC class II-linked peptide transporters (Hum/Tap2, Mus/Tap1), the bacterial exporters (Eco/HlyB, Pas/LktB), the heterocyst differentiation protein (Ana/HetA), the malarial parasite transporter (Pfa/Mdr1) and the yeast mating factor exporter (Ysc/Ste6).

The dendrogram in FIG. 2 indicates that MRP is only distantly related to previously identified members of the ABC transporter superfamily. Although the analysis suggests that it is most closely related to Lei/PgpA, the similarity between MRP and Lei/PgpA resides predominantly in two regions, both containing signatures of nucleotide binding folds (NBFs) (FIG. 3A). The alignment was generated using PILEUP as described in FIG. 2. The MRP sequence shown was compiled from four overlapping lambda gt11 cDNA clones. The alignment begins at a methionine residue in MRP that aligns with the initiator methionine of Lei/PgpA. The predicted initiator methionine of MRP itself is located 66 amino acids upstream. Identical and conserved amino acids are identified in FIG. 3A by double and single dots, respectively. The Walker A and B motifs and the 'active transport' family signature that are characteristic of nucleotide binding folds (NBFs) of ABC transporters are indicated by single lines and denoted A, B, and C, respectively. The predicted transmembrane regions of each protein are indicated by double lines. The region in Lei/PgpA indicated by a dashed line has a mean hydrophobicity value approaching that of a transmembrane region.

Figure 3B:
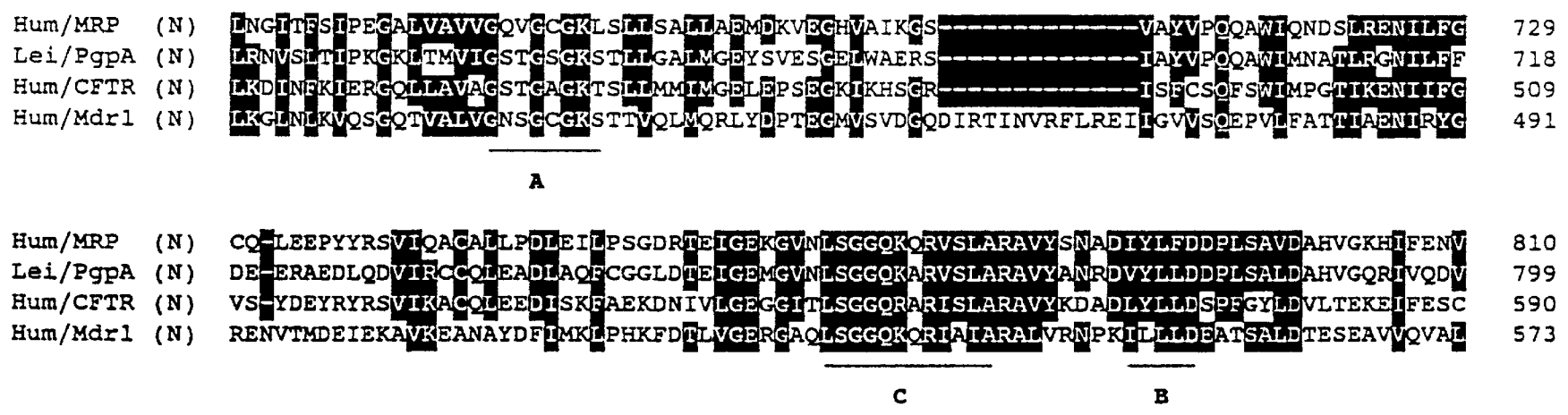
Figure 3B-1:
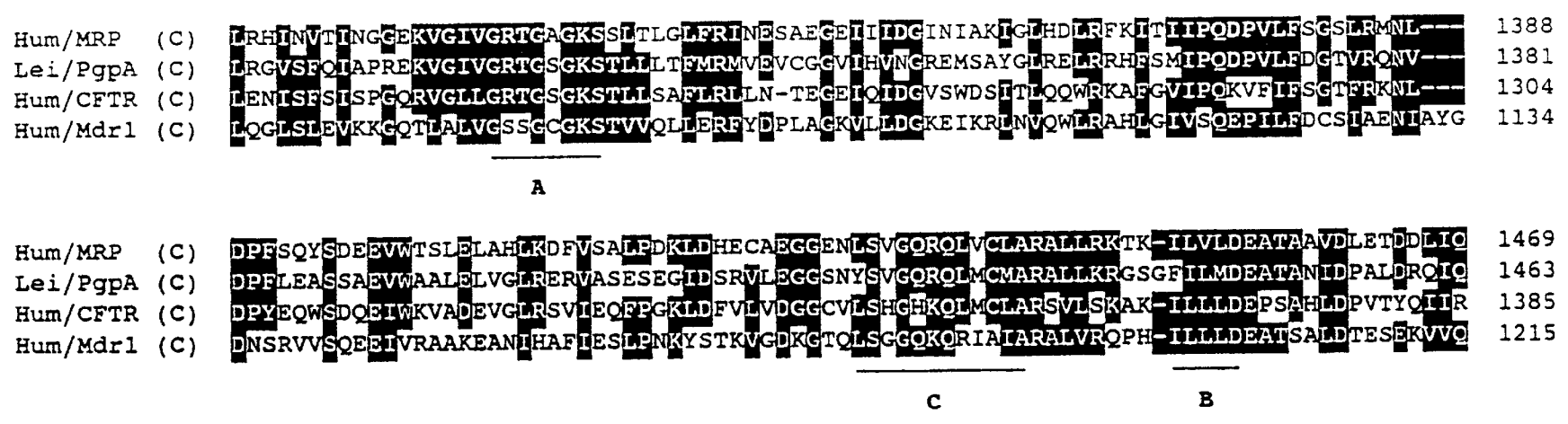

It has been proposed that the bipartite structure of P-glycoproteins reflects duplication of an ancestral gene that occurred prior to the evolutionary separation of animals and plants. However, comparison of the NH$_2$- and COOH-terminal NBFs of MRP and Lei/PgpA revealed less similarity than typically found between the two corresponding regions of P-glycoproteins. To determine whether this was a common structural feature of MRP, Lei/PgpA and Hum/CFTR, their NH$_2$- and COOH-terminal NBFs were aligned with each other and those of several P-glycoproteins. One such comparison using human P-glycoprotein (Hum/Mdr1) as an example is shown in FIG. 3B. Shown in FIG. 3B are the NH$_2$-terminal (N) and COOH-terminal (C) halves of the deduced amino acid sequence of MRP corresponding to ltpgpA (Lei/PgpA) (amino acids 650–799 and 1303–1463), human CFTR (Hum/CFTR) (amino acids 441–590 and 1227–1385), and MDR1 (Hum/Mdr1)(amino acids 410–573 and 1053–1215). The sequences are presented as aligned by PILEUP. Reverse type indicates that 3 of 4 amino acids at that position are identical or conserved. The conserved motifs A, B, and C described in FIG. 3A are underscored by a single line. The NH$_2$-terminal NBFs of MRP, Hum/CFTR and Lei/PgpA share structural features that clearly distinguish them from the NH$_2$-terminal NBF of Hum/Mdr1, particularly in the spacing of conserved motifs. This difference in spacing also contributes to the relatively low similarity between NH$_2$- and COOH-terminal NBFs in each of the three proteins. In addition, the COOH-terminal NBFs of MRP, Lei/PgpA and Hum/CFTR are more similar to each other than to either the COOH or NH$_2$-terminal NBFs of Hum/Mdr1. Similarity scores for the NH$_2$-terminal NBFs relative to MRP are: Lei/PgpA (0.93), Hum/CFTR (0.85) and Hum/Mdr1 (0.60). Comparable COOH-terminal scores are Lei/PgpA (0.87), Hum/CFTR (0.84) and Hum/Mdr1 (0.73). Similarity scores for NH$_2$- and COOH-terminal NBFs within the same protein are: MRP (0.61), Lei/PgpA (0.60), Hum/CFTR (0.62) and Hum/Mdr1 (1.10). These observations, combined with the overall analysis shown in FIG. 2, suggest that MRP, Lei/PgpA and CFTR evolved from a common ancestor containing both $NH_2$- and COOH-terminal NBFs, which was distinct, or diverged from the ancestral gene of the P-glycoproteins prior to the animal/plant separation.

EXAMPLE 3

EXPRESSION OF MRP IN NORMAL TISSUES

Figure 4:
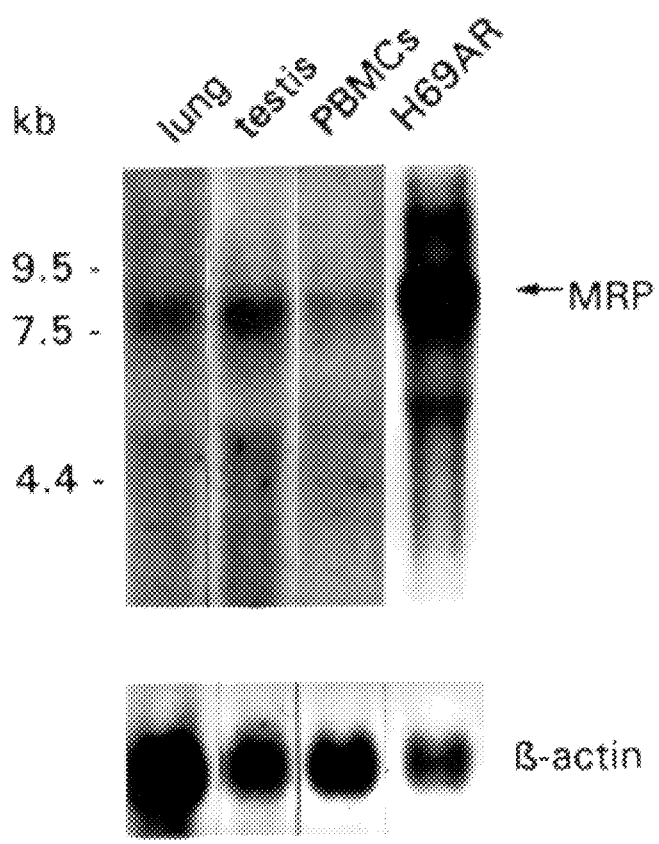
FIG. 4 is a Northern blot of total RNA from normal tissues hybridized with a 0.9 kb EcoRI cDNA fragment of the multidrug resistance protein of the invention.

Despite knowledge of its structure and its ability to act as a drug efflux pump, the normal physiological role(s) of P-glycoprotein has not been elucidated. Some possible clues to its function have been provided by its distribution in normal tissues. P-glycoprotein is highly expressed in secretory organs and tissues, such as the adrenals, kidneys, lumenal epithelium of the colon and the murine gravid uterus. It has also been detected in the lung although this finding is variable. Based on the cell types in which it is expressed, it has been postulated that P-glycoprotein may be involved in steroid transport and/or protection against xenobiotics. Northern blot analyses of total RNA preparations from a range of human tissues shown that MRP is expressed at relatively high levels in lung, testis and peripheral blood mononuclear cells (PBMCs)(FIG. 4). Lung and testis RNAs were obtained from Clontech Laboratories (Palo Alto, Calif.). PBMC RNA was prepared from cells isolated by centrifugation over Ficoll-Isopaque (specific gravity 1.078 g/ml; Pharmacia) of peripheral blood from healthy volunteers. Total RNAs from lung, testis and PBMCs (30 μg) and H69AR cells (10 μg) were analyzed as for FIG. 1A. The autoradiograph shown in FIG. 4 is from a blot probed with a 0.9 kb EcoRI cDNA fragment of MRP and exposed for 38 hours for the normal tissue RNAs and for 24 hours for the H69AR RNA. The blot was stripped and reprobed with $^{32}$P-labelled β-actin cDNA. The actin autoradiograph is a 24 hour exposure. MRP transcripts were below the level of detection in placenta, brain, kidney, salivary gland, uterus, liver and spleen.

EXAMPLE 4

MAPPING OF THE HUMAN MRP GENE

Figure 5:
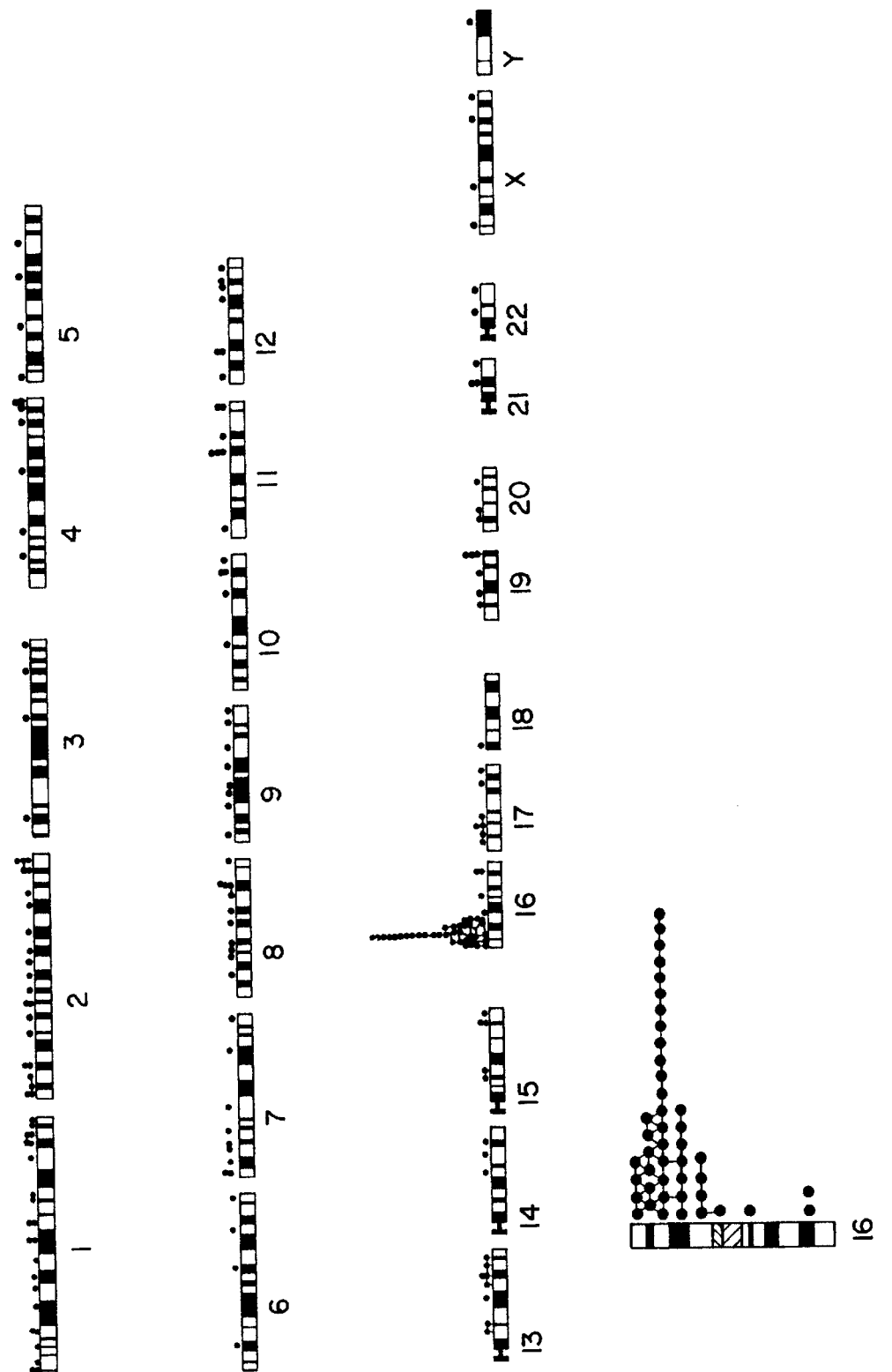
FIG. 5 is an ISCN-derived idiogram of the human karyotype showing silver grain distribution following in situ hybridization of a 1.8 kb EcoRI cDNA fragment of the multidrug resistance protein of the invention to metaphase chromosomes.

The human CFTR and MDR1 genes have been mapped to chromosome 7 at bands q31 and q21, respectively. The possible evolutionary relationship of MRP to these proteins prompted examination of the possibility that the MRP gene may be linked to one of these previously identified loci. In situ hybridization of a 1.8 kb EcoRI fragment of MRP cDNA was performed using the method of Harper and Saunders [Chromosoma 8, 431 (1981)]. Metaphase chromosomes on slides were denatured for 2 minutes at 70° C. in 70% deionized formamide, 2×SSC and then dehydrated with ethanol. The hybridization mixture consisted of 50% deionized formamide, 10% dextran sulfate, 2×SSC (pH 6), 20 μg/ml sonicated salmon sperm DNA and 0.2 μg/ml $^3$H-labelled MRP cDNA. The cDNA probe was labelled to a specific activity of 8.5×10$^8$ cpm/μg DNA with [$^3$H]-dTTP and [$^3$H]-dATP (New England Nuclear) using a Multiprime DNA Labelling System (Amersham) and denatured in the hybridization solution at 70° C. for 5 minutes. Fifty μl of the probe solution was placed on each slide and incubated at 37° C. overnight. After hybridization, the slides were washed in 50% deionized formamide, 2×SSC followed by 2×SSC (pH 7) and then dehydrated sequentially in ethanol. The slides were coated with Kodak NTB/2 emulsion and developed after exposure for 5 weeks at 4° C. Chromosomes were stained with a modified fluorescence, 0.25% Wright's stain procedure [C. C. Lin, P. N. Daper, M. Braekeleer, Cytogenet. Cell Genet. 39, 269 (1985)]. The positions of 200 silver grains directly over or touching well-banded metaphase chromosomes were recorded on the ISCN-derived idiogram of the human karyotype. A significant clustering of grains (40) was observed in the 16p region (p<0.0001) and the peak of the distribution was at 16p13.1, confirming that MRP was not linked to either CFTR or MDR genes. Approximately 160 metaphases were examined. These results are summarized in FIG. 5.

EXAMPLE 5

EXPRESSION OF MRP IN A DRUG SENSITIVE CELL CONFERS DOXORUBICIN RESISTANCE ON THE CELL

While increased concentrations of MRP and mRNA have been detected in multidrug resistant cell lines derived from a variety of tissues and several of these cell lines have also been shown to contain multiple copies of the MRP gene as a result of amplification and translocation of a region of chromosome 16 spanning the MRP gene at band p13.1, it remained possible, in view of the multistep selection procedures used to derive the cell lines, that overexpression of the MRP gene is only one component of a set of alterations required to confer multidrug resistance. The ability of MRP alone to confer drug resistance on a drug sensitive cell line was determined by constructing an MRP expression vector, transfecting the expression vector into drug sensitive cells and assessing the relative drug resistance of the transfected cell populations.

A DNA fragment corresponding to the complete coding region of MRP mRNA plus 86 nucleotides of 5' and 32 nucleotides of 3' untranslated sequence was assembled and transferred into the expression vector pRc/CMV under the control of the human cytomegalovirus promoter. A DNA fragment containing the complete coding region of MRP mRNA was assembled in the vector, pBluescript 11 KS$^+$ (Stratagene), using overlapping cDNA clones or PCR products generated from these clones. The fidelity of the MRP sequence was confirmed by DNA sequence analysis before moving the intact MRP fragment to the eukaryotic expression vector, pRc/CMV (Invitrogen). The integrity of the MRP fragment in the expression vector was assessed by detailed restriction mapping and DNA sequence analysis of the cloning sites. In the pRc/CMV vector, MRP expression is under the control of the enhancer/promoter sequence from the immediate early gene of human cytomegalovirus. The MRP transcript also contains part of the 3' untranslated region and the polyadenylation signal from bovine growth hormone mRNA which is provided by the vector. Thus, the pRc/CMV-MRP construct generates a transcript of 5.2 to 5.3 kb that includes the entire coding sequence (86 nucleotides of which are derived from MRP mRNA sequence), and approximately 250 nucleotides of 3' untranslated sequence (32 nucleotides of which are derived from MRP mRNA sequence). This vector also contains the bacterial aminoglycoside 3' phosphotransferase gene which confers resistance to geneticin (G418).

HeLa cells were transfected with either the parental vector, or the vector containing the MRP coding region, using supercoiled DNA and a standard calcium phosphate transfection procedure. HeLa cells were transfected with the pRc/CMV vector or the vector containing the MRP coding sequence using a standard calcium phosphate transfection procedure [J. Sambrook, E. F. Firtsch, T. Maniatis, *Molecular Cloning: A Laboratory Manual*, Cold Spring Harbor Laboratory Press, Cold Spring Harbor, N.Y. (1989)]. Approximately, 50,000 cells in each well of a 6-well tissue culture plate were exposed for 16 hours to 10 μg of supercoiled DNA in a calcium phosphate precipitate. After forty-eight hours, the growth medium was changed to include G418 at 200 μg/ml which selected for cells that expressed the neomycin resistance gene encoded by the pRc/CMV vector. Three weeks later, six independently transfected populations of cells were tested for resistance to doxorubicin using a tetrazolium salt microtiter plate assay (S. P. C. Cole, *Cancer Chemother. Pharmacol.* 26, 250 (1990)). Those populations demonstrating increased relative resistance to the drug were expanded for testing for cross-resistance to other cytotoxic drugs, and analysis of MRP mRNA and protein levels.

Poly(A)$^+$ RNA was isolated using the Micro-FastTrack RNA isolation kit (Invitrogen). The RNA was subjected to electrophoresis on a formaldehyde agarose gel and transferred to Zetaprobe membrane (Bio-Rad). The blots were hybridized with $^{32}$P-labeled cDNA fragment probes complementary to the mRNAs for MRP, MDR1 [A. M. Van der Bliek, F. Baas, T. Ten Houte de Lange, P. M. Kooiman, T. Van der Velde Koerts, P. Borst, EMBO J. 6, 3325 (1987)], topoisomerase 11 α [T. D. Y. Chung, F. H. Drake, K. B. Tan, S. R. Per, S. T. Crooke, C. K. Mirabelli, *Proc. Natl. Acad. Sci. U.S.A.* 86 9431 (1989)], topoisomerase 11 β [ibid.], annexin 11 (S. P. C. Cole, M. J. Pinkoski, G. Bhardwaj, R. G. Deeley, *Br. J. Cancer* 65, 498 (1992)), and a region of the pRc/CMV vector encoding part of the 3' untranslated region and polyadenylation signal from the bovine growth hormone gene. Hybridization of the probes was quantified by densitometry of the autoradiographs on a Molecular Dynamics Computing Densitometer. Care was taken to compare autoradiographic exposures that were within the linear range of the film. In addition, variations in loading of RNA on the gels were estimated by probing blots with a $^{32}$P-labeled glyceraldehyde-3-phosphate dehydrogenase (GAPDH) cDNA fragment (ATCC/NIH #57090), and by densitometric scanning of the ethidium bromide-stained ribosomal RNA bands on photographic negatives of the RNA gels.

The relative amounts of MRP protein were assessed by immunoblot analysis of total cell extracts and membrane-enriched fractions. Cell pellets were resuspended at 5×10$^7$ cells/ml in buffer containing 10 mM Tris-HCl, pH 7.4, 10 mM KCl, 1.5 mM MgCl$_2$, and protease inhibitors (2 mM phenylmethylsulfonyfluoride, 50 μg/ml antipain, 2 μg/ml aprotinin, 200 μg/ml EDTA, 200 μg/ml benzamidine, 1 μg/ml pepstatin). After 10 min on ice, cells were homogenized with approximately 80 strokes of a Tenbroeck homogenizer. The homogenate was adjusted to 250 mM in sucrose before remaining intact cells and nuclei were removed by centrifugation at 800×g at 4° C. for 20 min. To prepare a membrane-enriched fraction, the supernatant was centrifuged at 100,000×g at 4° C. for 20 min in a Beckman TL-100 ultracentrifuge and the pellet resuspended in 10 mM Tris-HCl, pH 7.4, 125 mM sucrose, and the protease inhibitors listed above. For sodium dodecyl sulphate (SDS) polyacrylamide gel electrophoresis and immunoblotting, appropriate amounts of protein were mixed 1:1 with solubilizing buffer (final concentration 4M urea, 0.5% SDS, 50 mM dithiothreitol). Samples were loaded without heating onto a 7% resolving gel with a 4% stacking gel. Proteins were transferred to Immobilon-P PVDF membranes (Millipore) using 50 mM 3-(cyclohexylamino)-1-propanesulfonate, pH 11.0. For detection of MRP, blots were incubated with an affinity-purified, rabbit polyclonal antibody raised against a synthetic peptide, the sequence of which was predicted from that of the cloned MRP cDNA and which is not found in any other known protein. Antibody binding was visualized with horseradish peroxidase-conjugated goat anti-rabbit IgG and enhanced chemiluminescence detection (Amersham). The affinity-purified anti-MRP antibody recognizes a glycosylated, integral membrane protein with an apparent molecular weight of 190 kilodaltons. In its deglycosylated form, the molecular weight of the protein decreases to 165- to 170 kilodaltons which is in agreement with the molecular weight of 171 kilodaltons predicted from the primary amino acid sequence of MRP.

At this time, the level of G418 in the growth medium was increased to 400 or 800 μg/ml without any noticeable effect on the growth rate of cells transfected with either the parental vector or the vector containing the MRP coding sequence. Transfected populations have been grown continuously for up to four months in G418-containing medium without any change in the level of resistance to doxorubicin. Integration of these vectors into genomic DNA has the potential to alter the expression of endogenous genes that might adventitiously increase drug resistance. Consequently, chemotherapeutic drugs were not used as selecting agents. Populations of transfected cells were selected solely by their ability to grow in the presence of G418. Since cells overexpressing MRP do not display increased resistance to this antibiotic, variable levels of expression of MRP are to be expected in the transfected cell populations.

Figure 6:
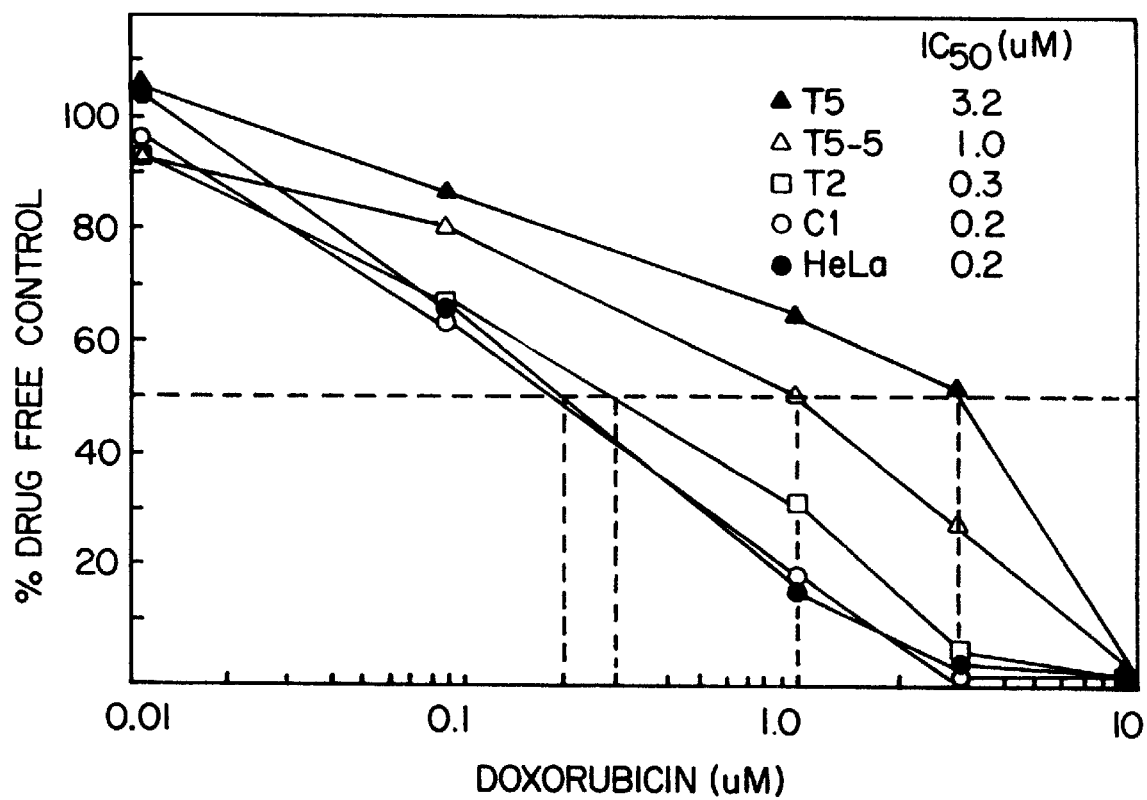
FIG. 6 is a graph depicting the relative cytotoxicity of doxorubicin on MRP-transfected HeLa cell populations (T2, T5), a clone of the T5 population (T5-5), untransfected HeLa cells and HeLa cells transfected with the parental expression vector (C1).

The relative resistances to doxorubicin are shown for two examples of G418 resistant cell populations transfected with the MRP expression vector (T2 and T5), as well as untransfected HeLa cells and a population transfected with the parental vector (C1) (FIG. 6). Key: HeLa cells (●); HeLa cells transfected with the expression vector pRc/CMV (C1, ○); HeLa cells transfected with the vector containing the MRP coding sequence (T2, ¤; T5, Δ); and a clone isolated from the doxorubicin-resistant transfected T5 cells shown (Δ, T5-5). Each point represents the mean of triplicate determinations in a single experiment and standard deviations were <5%. Similar results were obtained in three additional experiments. The IC$_{50}$ is indicated on the figure and is defined as the concentration of doxorubicin required to decrease by 50% the values obtained with untreated cells. In the examples shown, one of the populations transfected with the MRP expression vector (T2) displayed little change in doxorubicin resistance while resistance of the other (T5) was increased 15-fold. In addition, several clones from the resistant population were grown in the presence of G418 and their degree of doxorubicin resistance determined. Dose response curves for two of the transfectants (T2, T5) and for one of the clones (T5-5) were then compared to determine whether their resistance to doxorubicin correlated with the concentrations of MRP mRNA.

Figure 7A:
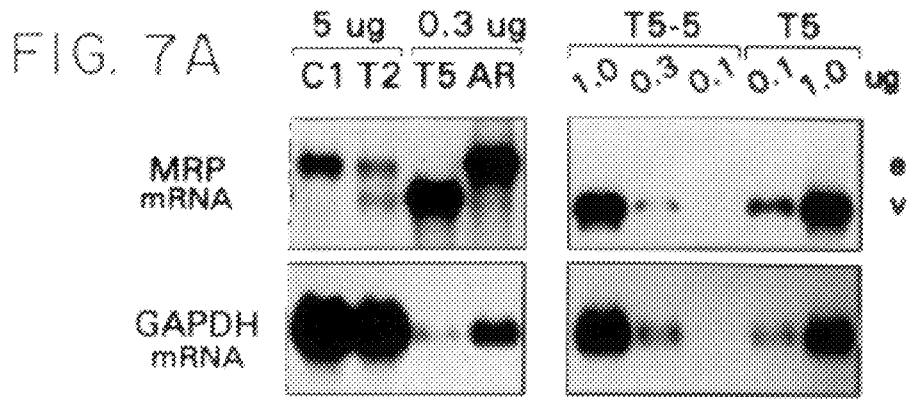
FIG. 7A is a Northern blot of poly(A)+ RNA from transfected and control HeLa cells hybridized with a 4 kb MRP cDNA fragment which hybridizes with endogenous MRP mRNA (e) and expression vector-derived MRP mRNA (v). Hybridization with a GAPDH cDNA demonstrates the relative amounts of poly(A)+ RNA in each lane.
Figure 7B:
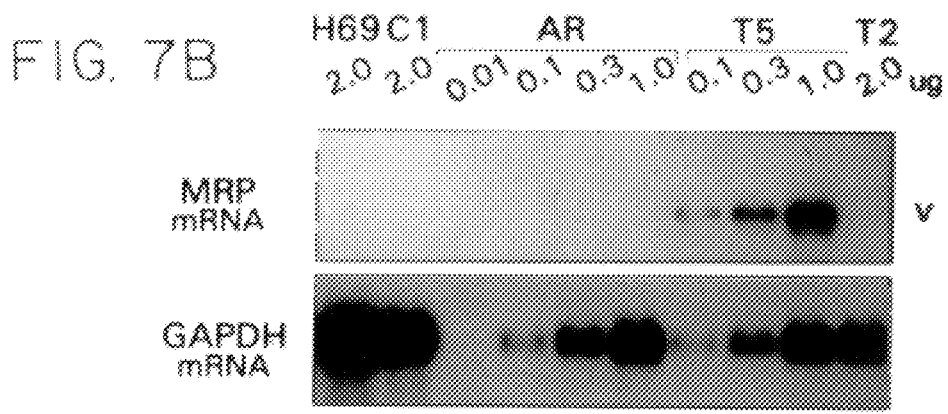
FIG. 7B is a Northern blot of poly(A)+ RNA from transfected HeLa cells and control cells hybridized with a DNA fragment from the pRc/CMV vector which hybridizes only to expression vector-derived MRP mRNA (v). Hybridization with a GAPDH cDNA demonstrates the relative amounts of poly(A)+ RNA in each lane.

The MRP mRNA produced from the expression vector has a predicted length of 5.2 to 5.3 kb including a poly(A) tail, thus allowing it to be distinguished from the longer, endogenous MRP mRNA by Northern analysis. A blot of poly(A)$^+$ RNA from the cell populations shown in FIG. 6 that was hybridized with a cloned cDNA probe corresponding to part of the MRP coding sequence, revealed a relatively abundant mRNA of approximately 5.3 Kb in the resistant transfectants and low levels of the endogenous MRP mRNA (FIG. 7A). The relative concentration of the 5.3 kb mRNA is 70- to 80-fold and 20- to 30-fold higher in the resistant cell population (T5) and clone (T5-5), respectively, than that of endogenous RP mRNA present in the control population (C1). Relative levels of mRNAs were determined by densitometry and normalization to the levels of GAPDH mRNA. Expression of the 5.3 kb MRP mRNA in the transfected cell population which showed little change in resistance (T2) was only approximately half that of endogenous MRP mRNA. Similar RNA blots were also probed with a DNA fragment from the pRc/CMV plasmid that forms part of the 3' untranslated region of the vector encoded MRP mRNA. This probe hybridized only with the 5.3 kb MRP mRNA, confirming that it was transcribed from the vector and did not result from the increased expression of an endogenous MRP-related gene (FIG. 7B). Thus in cells transfected with the MRP expression vector the relative level of drug resistance increases with the concentration of MRP mRNA.

Figure 7C:
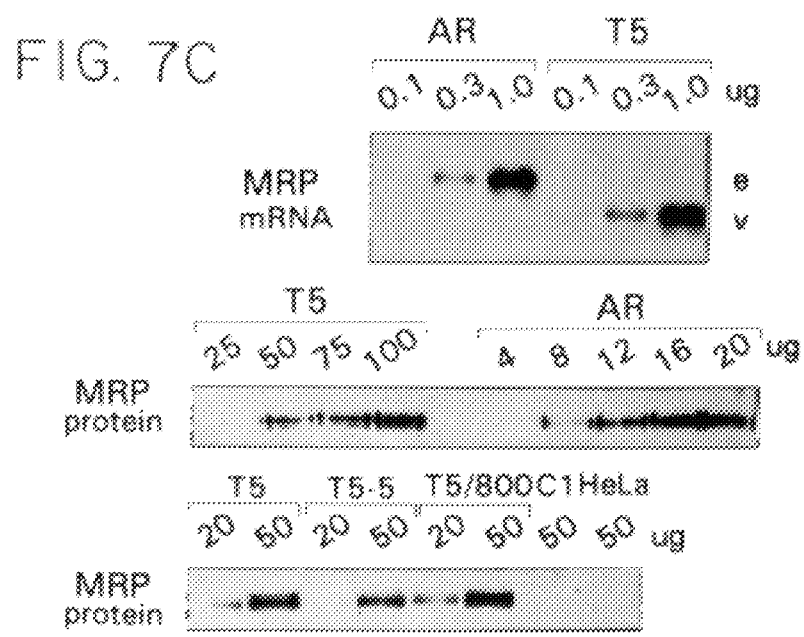
FIG. 7C is a Northern blot (MRP mRNA) and immunoblots (MRP protein) depicting the relative levels of expression vector-derived MRP mRNA and protein in transfected HeLa cells and endogenous MRP mRNA and protein in the H69AR cell line.

The concentration of endogenous MRP mRNA in the multidrug resistant H69AR cells (labeled AR in the figures) is approximately 100-fold higher than in the H69 parental cells (labeled H69 in the figures) and the relative resistances of the two cell lines to doxorubicin also differ by 50- to 100-fold. Vector encoded MRP mRNA levels in the T5 HeLa cell population are 70- to 80-fold higher than endogenous MRP mRNA levels in the parental cells. However, drug resistance is increased only 15-fold. To investigate why the relative increase in drug resistance was lower in the transfectants than in H69AR cells, we compared the levels of MRP mRNA and protein in the two different cell types. Northern analysis revealed that the levels of endogenous MRP mRNA in H69 cells and HeLa cells transfected with the pRc/CMV parental vector were similar. The relative abundance of vector encoded MRP mRNA in the drug resistant transfectant cell population (T5) was also comparable to that of endogenous MRP mRNA in H69AR cells (FIG. 7C). However, a protein blot with affinity purified anti-MRP antibody indicated that the level of protein in the T5 HeLa cell transfectants was 5- to 8-fold lower than in H69AR cells (FIG. 7C). These findings are consistent with the 15-fold increase in resistance observed in the transfected T5 cells compared to the 50- to 100-fold increase in H69AR cells. The lower level of protein in the transfected cells in most likely attributable to a difference in translational efficiency between the vector encoded and endogenous MRP mRNAs, although a difference in rates of degradation of the protein between the two cell types cannot excluded.

Figure 8A:
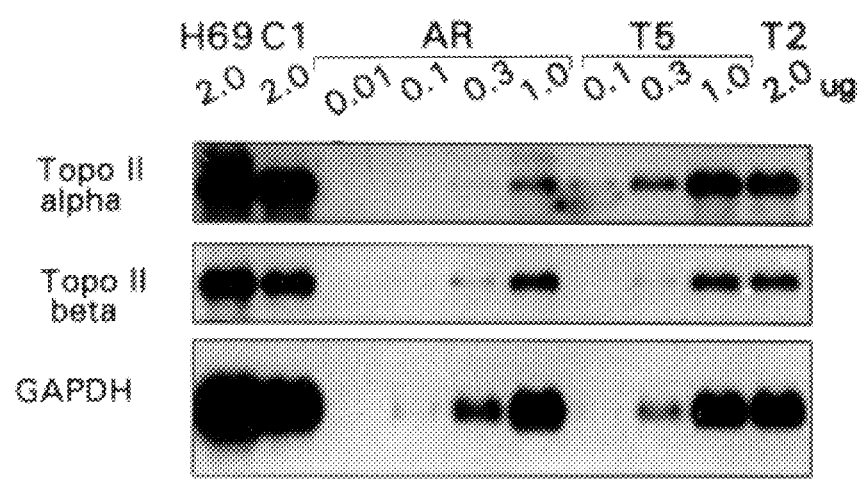
FIG. 8A is a Northern blot of poly(A)+ RNA from transfected HeLa cells and control cells hybridized with cDNA probes for topoisomerase II (Topo II) alpha and beta mRNAs. Hybridization with a GAPDH cDNA demonstrates the relative amounts of poly(A)+ RNA in each lane.
Figure 8B:
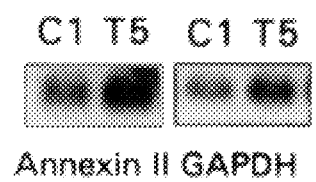
FIG. 8B is a Northern blot of poly(A)+ RNA from transfected HeLa cells and control cells hybridized with a cDNA probe for annexin II mRNA. Hybridization with a GAPDH cDNA demonstrates the relative amounts of poly (A)+ RNA in each lane.

Since H69AR cells were obtained by multistep selection, it is possible that additional alterations have occurred which may, either independently or in concert with MRP, influence their degree of resistance to some drugs. H69AR cells have been shown to have decreased levels of topoisomerase 11 α and β mRNA and protein which could enhance their resistance to anthracyclines and epipodophyllotoxins. They have also been shown to overexpress annexin 11 which may affect the trafficking of membrane proteins. Annexin 11 has been shown to be involved in formation of fusogenic vesicles and in exocytosis. S. P. C. Cole, M. J. Pinkoski, G. Bhardwaj, R. G. Deeley, Br. J. Cancer 65, 498 (1992). It is unknown to what extent these additional changes influence the degree of resistance of H69AR cells or whether they are linked in any way to overexpression of MRP. However, overexpression of MRP in the transfected cells does not alter the levels of mRNAs specifying either topoisomerase 11 isoform (FIG. 8A) or annexin 11 (FIG. 8B), nor do the transfected HeLa cells display any alterations in the level of Mdr1 mRNA. These observations strongly support the conclusion that increased resistance to doxorubicin in the transfected cells is directly attributable to overexpression of MRP.

EXAMPLE 6

EXPRESSION OF MRP IN A DRUG SENSITIVE CELL CONFERS MULTIDRUG RESISTANCE ON THE CELL

To determine whether the increased doxorubicin resistance of transfected cells was accompanied by increased resistance to other classes of chemotherapeutic drugs, the cells were tested for cross-resistance to vincristine (a Vinca alkaloid), VP-16 (an epipodophyllotoxin) and cisplatin (FIG. 9). Cytotoxicity assays were performed on untransfected HeLa cells (●), HeLa cells transfected with the expression vector pRc/CMV (C1, °), HeLa cells transfected with the expression vector pRc/CMV-MRP and maintained in G418 at 400 μg/ml for 4 months (T5, Δ), and T5 cells maintained at 800 μg/ml G418 for 1 month (T5-800/1, Δ) and 3 months (T5-800/3, ⋈). Each point represents the mean of triplicate determinations in a single experiment and standard deviations were <5%. Similar results with vincristine and VP-16 were obtained in two to three additional experiments. The $IC_{50}$'s of the various cell lines are indicated on the figure. Dose response curves for several independently propagated cultures of MRP transfectants indicate that they are approximately 25-fold and 5- to 10-fold resistant to vincristine and VP-16, respectively, relative to untransfected HeLa cells or cells transfected with parental vector (C1). The transfectants showed no increase in cisplatin resistance which is consistent with the pharmacological phenotype of H69AR cells and which is also characteristic of cells that overexpress P-glycoprotein. These results demonstrate for the first time that this phenotype can be conferred by a member of the ABC superfamily of transporters that is structurally very different from the P-glycoproteins.

EXAMPLE 7

PREPARATION OF ANTI-MRP ANTIBODIES USING MRP PEPTIDES AS THE IMMUNOGEN

MRP is encoded by a mRNA of approximately 6.5 kb with an extended open reading frame of 1531 amino acids. The protein is predicted to contain two nucleotide binding folds (NBFs) and 12 transmembrane regions, divided 8 and 4 between the NH2- and COOH-proximal halves of the molecule, respectively. To confirm that a protein of the predicted size and sequence is overexpressed in resistant H69AR cells, polyclonal antibodies were prepared against synthetic peptides based on the deduced amino acid sequence of MRP and used in immunoanalyses.

One peptide of sequence AELQKAEAKKEE was selected from the highly divergent cytoplasmic linker domain of MRP (MRP-L, position 932–943) while the second peptide (GENLSVGQRQLVCLA) was chosen from the second nucleotide binding domain of MRP (MRP-2, position 1427–1441). Both peptides were synthesized on Ultrasyn D resin for direct immunization by the Biotechnology Service Centre at the Hospital for Sick Children (Toronto, Ont.). Approximately 400 μg of bound peptide was resuspended in distilled water and sonicated. The resulting suspension was emulsified in an equal volume of complete Freund's adjuvant (Difco) and injected s.c. at four sites in 3-month old female New Zealand White rabbits. At 2- to 3-week intervals, the same amount of immunogen emulsified in incomplete Freund's adjuvant was injected s.c. Rabbits were bled by arterial puncture beginning 2 weeks following the third immunization and their sera were tested for the presence of antibodies by an enzyme-linked immunosorbent assay (ELISA) and by immunoblotting.

Rabbit antisera obtained after immunization with peptide MRP-L that were positive by ELISA or western blotting were concentrated by ammonium sulfate precipitation and purified by affinity chromatography. Affinity columns were constructed by coupling the MRP-L peptide to CNBr-activated Sepharose (5 μmole peptide/ml gel) according to the instructions of the supplier (Pharmacia LKB Biotechnology Inc.) followed by extensive washing with 10 mM Tris, pH 7.5. The ammonium sulfate precipitate was dissolved in phosphate-buffered saline, dialyzed extensively against the same buffer and then applied to the prewashed affinity column. The loaded column was washed first with 10 mM Tris pH 7.5 followed by 10 mM Tris, pH 7.5, 0.5M NaCl before eluting the antibody with 0.1M glycine, pH 2.5. Fractions were neutralized in collection tubes containing 1M Tris, pH 8.0. The desired fractions were pooled, dialyzed extensively against phosphate-buffered saline and concentrated by Amicon concentrators/filtration. The final protein concentration of the purified antibody was adjusted to 0.7–1.5 mg/ml. Rabbit antisera obtained after immunization with peptide MRP-2 were used without further purification.

ELISA positive antisera from these rabbits were used in immunoblot analyses. Polyacrylamide gel electrophoresis was carried out by the method of Laemmli with a 5% or 7% separating gel and a 4% stacking gel. Samples were diluted 1:1 in solubilizing buffer to a final concentration of 4M urea, 0.5% SDS, 50 mM DTT and loaded on the gels without heating. For immunoblotting, proteins were transferred after gel electrophoresis to Immobilon-P PVDF membranes (Millipore, Mississauga. Ont.) using 50 mM CAPS, pH 11.0. Blots were incubated for 1 h in blocking solution (5% normal goat serum/5% HyClone serum/1% BSA) in TBS-T (10 mM Tris, pH 7.5, 0.05% Tween 20, 150 mM NaCl). Anti-MRP antibodies were added directly to the blocking solution and incubated for 2 h. The blot was washed 3×5 min in TBS-T and goat anti-rabbit IgG horseradish peroxidase-conjugate [affinity purified F(ab')2 fragment (Jackson ImmunoResearch) or whole molecule (ICN Biomedicals)] diluted in blocking buffer added. After a 1 h incubation, the blot was washed 5×5 min in TBS-T, and antibody binding detected by ECL (Amersham, UK) and exposure on Kodak XOMAT film. The antisera detected a 190 kD protein in resistant H69AR cells which was not detectable in sensitive H69 and revertant H69PR cells.

The antisera were also used in immunoprecipitation experiments using cell membrane preparations of cells metabolically labelled with $^{35}$S-methionine. Cells were cultured in 50 μCi/ml $^{35}$S-methionine (Tran $^{35}$S-label; cell labelling grade; specific activity, 710 Ci/mmol) (Dupont NEN) overnight in methionine-deficient RPMMI 1640 medium (Sigma) or with 500 μCi/ml $^{32}$P-orthophosphoric acid (Carrier free, 500 mCi/ml) (Dupont NEN) in phosphate-deficient RPMI 1640 medium (ICN) for 4 h. Crude radiolabelled 100,000×g membrane-enriched fractions were prepared and immunoprecipitated as follows. Frozen or fresh cells (50×10$^6$/ml) were suspended in 10 mM Tris-HCl, pH 7.4 containing 10 mM KCl, 1.5 mM MgCl$_2$ with protease inhibitors (2 mM phenylmethylsulfonylfluoride, 50 μg/ml antipain, 2 μg/ml aprotinin, 200 μg/ml EDTA, 200 μg/ml benzamidine, 0.5 μg/ml leupeptin, 1 μg/ml pepstatin) and 0.025 mg/ml RNase A and 0.05 mg/ml DNase 1. After 10 min., the suspension was homogenized in a chilled Tenbroeck homogenizer with 80 strokes of the pestle. The homogenate was then centrifuged at 800×g at 4° C. for 15 min. to remove nuclei and remaining intact cells. A membrane-enriched fraction was prepared by ultracentrifugation of the supernatant at 100,000×g at 4° C. for 20 min. The pellets were resuspended in 10 mM Tris HCl, pH 7.6 with 125 mM sucrose and protease inhibitors as above. Protein concentrations were determined by the Peterson modification of the Lowry assay and aliquots were stored at −80° C.

Proteins were solubilized in 1% CHAPS, 100 mM KCl, 50 mM Tris-HCl, pH 7.5, at a detergent to protein ratio of 20:1 for 1 h at 4° C. with frequent vortexing followed by centrifugation at 100,000×g for 20 min using a T100.3 rotor in a Beckman Ultracentrifuge. The supernatant (whatever percentage of protein is solubilized from an initial 40 μg of membrane protein) was incubated with affinity purified MRP-L antisera (25 μg solubilized in 1% CHAPS, 100 mM KCl, 50 mM Tris-HCl, pH 7.5) overnight at 4° C. The samples were made up 700 μl with 1% CHAPS buffer then incubated with 50 μl (10% w/v) Protein A Sepharose C1-4B (Pharmacia) for 3 h at 4° C. with gentle rocking. The samples were centrifuged for 10 sec at 14,000×g and sequentially washed for 5 min with 1 ml each of Buffer 1 (10 mM Tris-HCl, pH 8.0, 0.5 mM NaCl, 0.5% Nonidet P-40, 0.05% SDS), Buffer 2 (10 mM Tris-HCl, pH 8.0, 0.15M NaCl, 0.5% Nonidet P-40, 0.05% SDS, 0.5% deoxycholate) and Buffer 3 (10 mM Tris-HCl, pH 8.0, 0.05% SDS). The washed beads were incubated with 100 μl of 4M urea, 0.5% SDS, 50 mM DTT for 1 h at room temperature with frequent vortexing. The samples were centrifuged and the supernatants analyzed on 7% polyacrylamide gels. The gels were fixed in isopropanol:water:acetic acid (25:65:10) for 30 min followed by-the addition of the fluorographic reagent Amplify (Amersham). The gels were dried and then exposed to film overnight at −80° C. A 190 kD protein was detectable by immunoprecipitation of membrane-associated proteins from $^{35}$S-methionine labelled H69AR cells with the immunoreactive antisera.

The apparent molecular weight of the immunodetectable 190 kD protein in the H69AR cell membranes is approximately 20 kD greater than the predicted 171 kD molecular weight of MRP based upon the deduced primary amino acid sequence. However, analysis of the MRP sequence indicates the presence of three potential N-glycosylation sites in regions predicted to be asymmetrically distributed about a membrane bilayer. To determine whether or not the 190 kD protein was N-glycosylated, two sets of experiments were carried out. First, resistant H69AR cells were grown in the presence of tunicamycin, a potent inhibitor of N-linked glycosylation. N-linked glycosylation was inhibited in H69AR cells by culturing in 15 μg/ml tunicamycin (Sigma) for 24 h. Treated cells were washed twice with phosphate-buffered saline and then whole cell lysates were prepared by homogenization in lysis buffer (20 mM Tris HCl, pH 7.5, 20 mM KCl, 3 mM MgCl2. 0.5 mg/ml DNase 1, 0.25 mg/ml RNase A) with protease inhibitors as described above. Polyacrylamide gel electrophoresis and immunoblotting of the whole cell lysates were carried out as before. In the second approach, H69AR 100,000×g membranes were incubated with the deglycosylase PNGase F. Membrane-enriched fractions (200 μg protein) were diluted to a final concentration of 1 μg/μl in 50 mM Na phosphate buffer, pH 7.5, containing 25,000 NEB units PNGase F (New England Biolabs). After 8 h at 37° C., an additional 25,000 NEB units PNGase F was added followed by incubation overnight at 37° C. Sample buffer was added directly and SDS-PAGE and immunoblotting carried out as before. In both cases, a 170 kD protein was detected by immunoblot analyses which correlates well with the 171 kD predicted molecular weight of MRP. Similar results were observed with cells transfected with a full-length MRP cDNA (T5 cells) (see Almquist, et al. *Cancer Research* 55:102–110 (1995).

To confirm that MRP is an ATP-binding protein, as suggested by the presence of ATP-binding signature motifs, membranes from resistant H69AR and sensitive H69 cells were photolabelled with $^{32}$P-8-azido ATP. Crude membrane-enriched fractions were resuspended at 1 μg/μl protein in 10 mM Tris-HCl, pH 7.6, buffer containing 1 mM $MgCl_2$ and protease inhibitors as described above. After the addition of 3–4 μCi $^{32}$P-8-azido-ATP (specific activity 2–10 Ci/mmol; ICN Biomedical, Mississauga, Ont.), incubation on ice was continued for 1–5 min. The azido-ATP was cross-linked to the protein on ice by irradiation at 366 nm about 10 cm from the light source for 8 min. using a Stratalinker set at 1100 μW. The labelled proteins were stored at −80° C. until polyacrylamide gel electrophoresis or immunoprecipitations were carried out. Specificity of the labelling was confirmed by competition with cold excess ATP (Boehringer Mannheim, Laval, Que.) which was added to the membrane preparations prior to the addition of $^{32}$P-8-azido-ATP. These studies revealed strong, specific labelling of a 190 kD protein in membranes from the H69AR cells that was not detected in drug sensitive H69 cells. Our results indicate that in H69AR cells, the MRP gene encodes an N-glycosylated ATP-binding protein of 190 kD.

EXAMPLE 8

PREPARATION OF ANTI-MRP MONOCLONAL ANTIBODIES

In this Example, monoclonal antibodies reactive against MRP were prepared by immunizing mice with a multidrug resistant cell (H69AR) that expresses MRP followed by isolation of antibody-producing cells, fusion with immortalized cells and selection of specific monoclonal antibodies. The following methodologies were used:

Cell Culture

The parental H69, doxorubicin-selected multidrug resistant H69AR, and revertant H69PR small cell lung cancer cell lines were maintained as described in Mirski, S. E. L. et al. (1987) Cancer Res. 47:2594–2598; Cole, S. P. C. et al. (1992) Br. J. Cancer 65:498–502. T5 cells (HeLa cells that have been made multidrug resistant by transfection with a fall length MRP cDNA expression vector, pRc/CMVMRP1) and C1 cells (HeLa cells that have been transfected with pRc/CMV vector alone). were maintained in the same medium as the lung cancer cells, supplemented with 400 μglml G-418 (Sigma Chemical Co., St. Louis, Mo.). SP2/0Ag14 myeloma cells (ATCC# CRL 1581) were maintained in DMEM (Hybri-Max, Sigma) supplemented with 4 mM L-glutamine and 5% heat inactivated bovine calf serum. Approximately one week prior to fusion, Sp2/0 cells were challenged with 0.132 mM 8-azaguanine (Sigma) for one passage.

Generation of Hybridomas

Membrane-enriched cell fractions were prepared and resuspended in Tris-sucrose buffer (10 mM Tris HCI, pH 7.5, 0.25M sucrose) containing protease inhibitors. Female BALB/c mice (6–8 weeks old) received three i.p. injections of 150 μg H69AR membrane protein (without detergent) in PBS and mixed 1:1 with an emulsion of monophosphoryl lipid A (MPL), synthetic trehalose dicorynomycolate (TDM) and cell wall skeleton (CWS) (obtained commercially from RIBI ImmunoChem Research, Inc., Hamilton, Mont.) at approximately three week intervals. Three days before fusion, 100 μg H69AR membrane protein was injected i.v. into a tail vein. Spleen cells were fused with SP2/0 myeloma cells with polyethylene glycol 4000 (Sigma Chemical Co., St. Louis, Mo.) according to standard methods (see e.g., Kennett, R. H. (1979) Meth. Enzymol. 58:345–359; Mirski, S. E. L. et al. (1989) Cancer Res. 49:5719–5724). Cultures were fed with DMEM medium containing 100 μM hypoxanthine, 0.4 μM aminopterin, 16 μM thymidine, 20% heat-inactivated fetal bovine serum and gentamycin (25 μg/ml) (ICN Biomedicals, St. Laurent, Quebec, Canada). After initial screening, aminopterin was omitted from the growth medium.

Screening, Cloning, Isotyping and Ascites Production

After 11 days of growth in selective medium, 459 hybridoma supernatants were tested for the presence of MRP-specific antibody by immunodot blot analysis. H69, H69AR, and H69PR membrane proteins in TBS were blotted (4 μg protein/dot) onto Immobilon-P PVDF membrane (Millipore, Mississauga, Ontario, Canada) using a 96-well vacuum manifold and blots were kept wet at all times. The blots were cut into strips such that each strip had spots of membrane proteins from each of the three cell lines. After transfer to 24-slot incubation trays, strips were blocked for 1 h in blocking solution (5% bovine calf serum/5% normal goat serum/1% BSA in TBS-T). Hybridoma supernatants were added directly to the blocking solution at a final dilution of 1:9. After 90 min, the strips were washed 3×5 min in TBS-T, and secondary antibody (horseradish peroxidase-conjugated goat anti-mouse IgG+IgM (H+L), F(ab')2 fragment) (Pierce, Edmonton, Alberta) was added (diluted 1:10,000 in blocking buffer). After 1 h, the strips were washed 5×5 min in TBS-T, and antibody binding was determined by enhanced chemiluminescence detection (Amersham, Oakville, Ontario, Canada) and exposure on Kodak X-OMAT film.

Hybridomas which showed preferential reactivity with H69AR membrane dots were subjected to a second immunodot blot, using strips with C1 and T5 membrane protein dots in addition to the H69, H69AR, and H69PR dots. Hybridomas which reacted preferentially with H69AR and T5 membrane dots compared to H69, H69PR, and C1 dots were cloned twice by limiting dilution and then expanded. Immunoglobulin subtypes of the MAbs produced by the five stable hybridoma clones obtained were determined using an isotyping reagent kit (Sigma). To produce ascites, 5×10$^6$ hybridoma cells resuspended in PBS were injected i.p. into pristane-pretreated BALB/c (nu/nu) mice. Ascites fluid was collected over the next 1–2 weeks and MAbs were purified by passage over Econo-Pac DEAE Blue cartridges (BioRad, Mississauga, Ontario, Canada) according to manufacturer's instructions.

Immunoblotting and Immunoprecipitation of MRP

Membrane protein was solubilized in Laemmli buffer (Laemmli, U. K. (1970) Nature 227:680–685), and subjected to SDS-PAGE and electroblotting by standard methods. Immunoblotting was performed as described above for dot blot strips. For H69, H69AR and H69PR membrane proteins, 2.5 μg/dot were used. For C1 and T5 membrane proteins, 5 μg/dot were used. The blots were incubated with hybridoma supernatants or with an anti-P glycoprotein mAb, C219 (Centocor, Malvern, Pa.; used at 1 μg/ml). In some experiments, a polyclonal antiserum (MRP-2) that was raised against a peptide corresponding to amino acids 1418 to 1432 of MRP, and which is known to cross-react with P-gp, was used as a positive control for MRP detection.

Immunoprecipitations were carried out as follows. Cells were incubated for 24 h in L-methionine-deficient RPMI 1640 medium (Sigma) supplemented with 10% dialyzed bovine calf serum and 50 μCi/ml [$^{35}$S]methionine (1110 Ci/mmol, cell labelling grade) (Dupont NEN, Markham, Ontario, Canada). Cells were washed twice with PBS and resuspended at approximately 6×10$^7$ cells/ml in solubilizing buffer (1% CHAPS, 100 mM KCl, 50 mM Tris-HCl, pH 7.5) containing protease inhibitors. After 1 h on ice, insoluble matter was removed by ultracentrifugation. Aliquots of the supernatant were brought up to 250 μl with solubilizing buffer, and incubated for at least 2 h at 4° C. with hybridoma supernatant diluted 1:6. Antibody-MRP complexes were recovered by incubation with 25% w/v GammaBind Plus Protein G Sepharose (30 μl) or 10% w/v Protein A Sepharose CL-4B (25 μl) (Pharmacia, Baie D'Urfe, Quebec, Canada) in solubilization buffer for at least 2 h at 4° C. The samples were sequentially washed and precipitated proteins were eluted from the beads with Laemmli buffer and analyzed by SDS-PAGE and fluorography.

Indirect Immunofluorescence and Flow Cytometry

Cells were washed twice with cold PBS and fixed with either 0.5% paraformaldehyde (Sigma) in PBS for 30 min at 4° C. or with 70% methanol at −20° C. for 10 min. All subsequent procedures were done at 4° C. Cells were washed once with blocking solution (1% BSA/5% normal goat serum/PBS). For MAbs QCRL-2 and QCRL-3, the cells were incubated in blocking solution with 0.1% Triton X-100 for 30 min, followed by direct addition of hybridoma supernatant or ascites diluted as required. After incubation for 1 h, the cells were washed once in blocking solution with 0.1% Triton X-100 followed by a wash in blocking solution alone. The washed cells were incubated with fluorescein-conjugated goat anti-mouse IgG (H+L) F(ab')2 fragment (Pierce) diluted 1:50 in blocking solution for 30 min, and then washed twice in blocking solution with 0.1% Triton X-100. For MAb QCRL-1, cells were treated similarly except Tween-20 was used at 0.1% instead of Triton X-100, and was included in all washes and incubations. Finally, cells were resuspended in 1% paraformaldehyde in PBS and either analysed on a Coulter Epic flow cytometer or cytospins were prepared for examination by fluorescence microscopy.

RESULTS

Using spleens from mice immunized with MRP-enriched membranes, murine hybridomas were generated and screened for their ability to detect MRP in non-denatured membranes. Five stable cloned hybridoma cell lines, designated QCRL-1, QCRL-2, QCRL-3, QCRL-4, and QCRL-6, were obtained.

Figure 10:
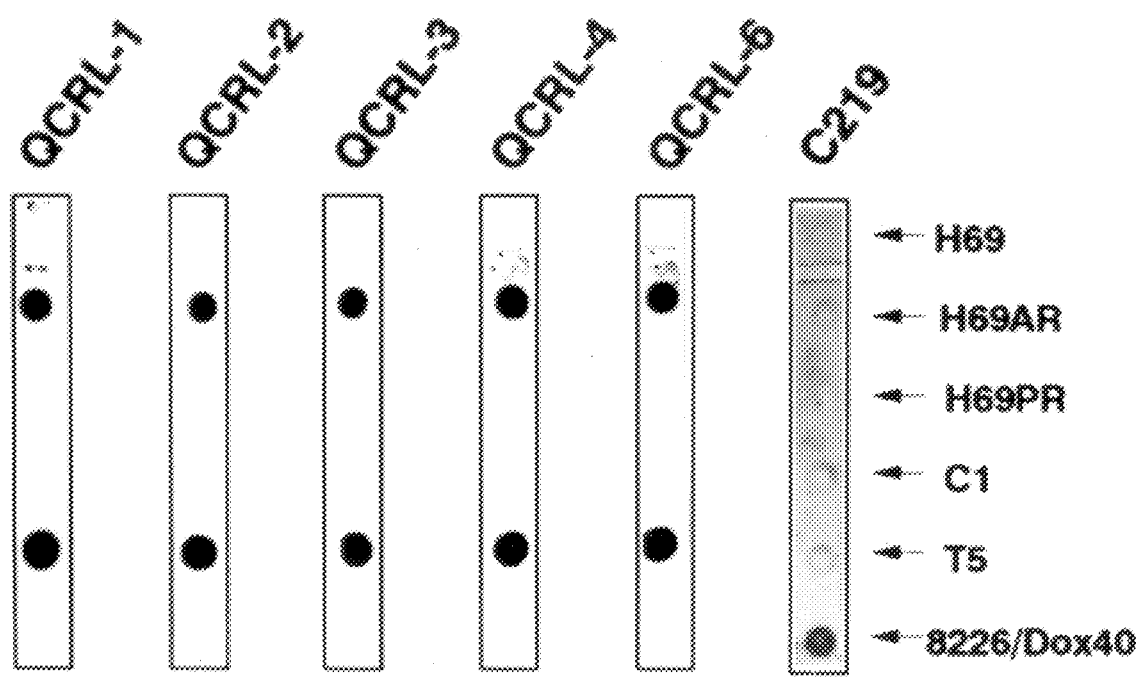
FIG. 10 is a photograph of immunodot blots of MRP-overexpressing cells (H69AR and T5), P-glycoprotein-overexpressing cells (8226/Dox40) or control cells (H69, H69PR and C1) screened with anti-MRP mAbs (QCRL-1, -2, -3, -4 or -6) or an anti-Pgp mAb (C219).

MAbs QCRL-1, QCRL-4, and QCRL-6 were determined to be of the IgG, subclass, MAb QCRL-2 was an IgG2b, and MAb QCRL-3 was an IgG2a. The MAbs reacted strongly with MRP-rich membrane fractions from both drug-selected H69AR cells and MRP-transfected T5 cells and weakly or not at all with parental H69, revertant H69PR and control C1 cell membranes (see the immunoblot analysis shown in FIG. 10). None of the MAbs cross-react with P-gp, since they showed no reactivity with membrane fractions from 8226/Dox40 cells which are known to overexpress this 170 kDa protein and which reacted with the P-gp-specific MAb C219.

To confirm the MRP-specificity of these MAbs, immunoprecipitation and immunoblot analyses were carried out. MAb QCRL-3 immunoprecipitated a single 190 kDa protein from [35S]methionine-labelled H69AR cells when protein A was used to bind immune complexes (see FIG. 11A). MAb QCRL-2 also precipitated this 190 kDa protein. This precipitated protein had the same electrophoretic mobility as the protein precipitated by the polyclonal antiserum MRP-2 which was raised against an MRP-derived peptide. To immunoprecipitate MRP with MAb QCRL-1, protein G was required to bring down immune complexes (see FIG. 11B). Protein G was also effective in precipitating MRP with MAbs QCRL-2 and QCRL-3. A 190 kDa protein was precipitated with all three MAbs from the MRP-transfected T5 cells but not from C1 control cells. Taken together, these data provide confirmation of the WRP-specificity of MAbs QCRL-1, -2 and -3.

Immunoblot analyses (Western blots) with the MAbs were carried out under both reducing and non-reducing conditions. The results for reducing conditions are shown in FIG. 12A–C. In panels A and C, 5 μg of H69, H69AR or H69PR protein were used, 10 μg T5 or C1 protein were used, and 25 μg 8226/Dox4O protein were used. In panel B, 15 μg T5 protein were used and 75 μg of H69PR protein were used.

As shown in FIGS. 12A and B, MAb QCRL-1 detected a protein of 190 kDa. This protein is easily detectable at high levels in membranes from H69AR and T5 cells using QCRL-1 hybridoma supernatant and the relative levels in the two cell types are approximately the same as those observed using MRP-specific polyclonal antisera. The very low levels of the 190 kDa protein found in the drug-sensitive revertant H69PR cells could also be detected with a very high degree of specificity using MAb QCRL-1 ascites (see FIG. 12B). The 170 kDa P-gp, detectable in 8226/Dox40 cells with MAb C219 (see FIG. 12C), was not detected in immunoblots with MAb QCRL-1, consistent with the immunodot blot analyses.

Figure 13:
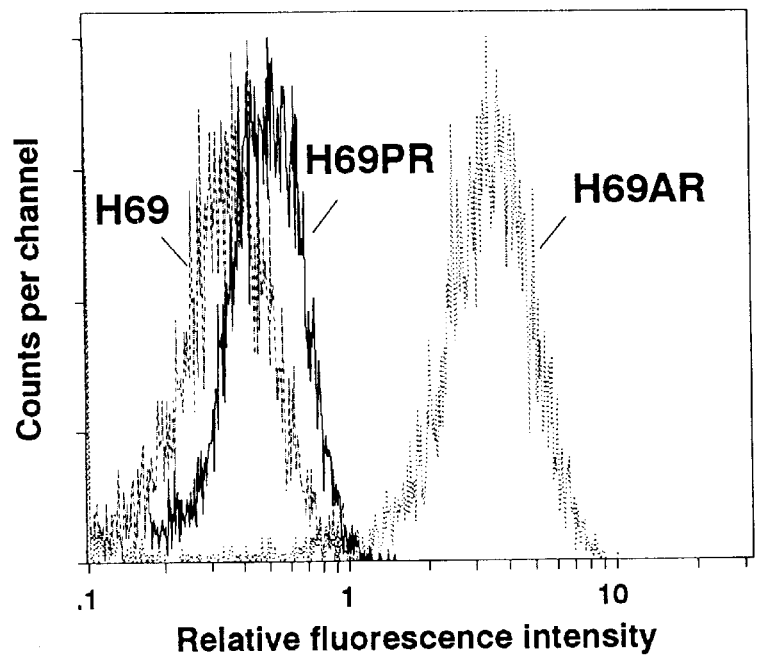
Figure 13:
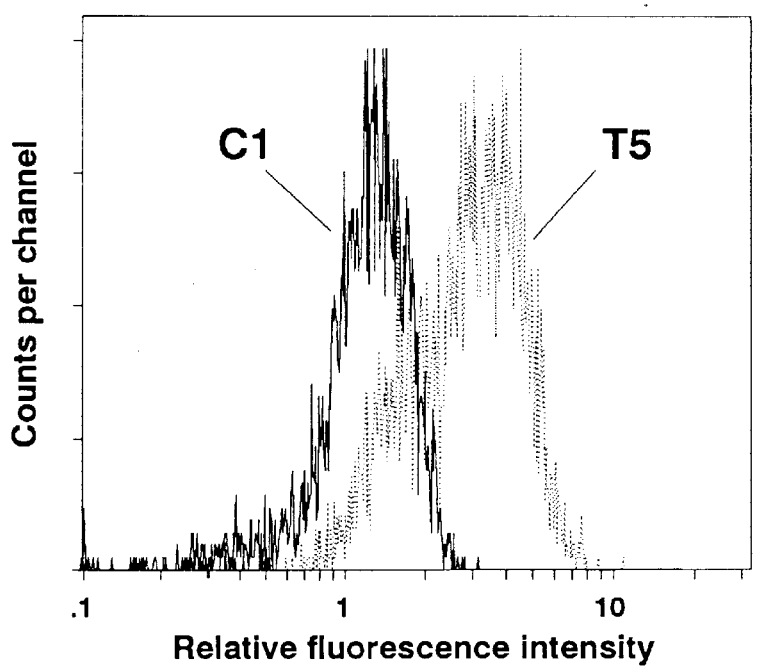

To demonstrate that MRP-specific MAbs are able to recognize MRP epitopes in fixed cells and tissues, labelling of H69, H69AR, H69PR, C1, and T5 cells with MAbs QCRL-1, QCRL-2 and QCRL-3 was examined by flow cytometry and indirect immunofluorescence microscopy. None of the MAbs reacted with unfixed cells, suggesting that the MRP epitopes detected by these MAbs are not exposed on the cell surface. However, the epitopes recognized by these three MAbs remained intact after fixation of cells with either 0.5% paraformaldehyde or 70% methanol. MRP reactivity with MAbs QCRL-1 and QCRL-3 also remains intact after fixation with 10% formalin. Representative flow cytometry histograms obtained with MAb QCRL-3 and cells fixed with 0.5% paraformaldehyde are shown in FIGS. 13, panels A and B. MAb QCRL-3 clearly discriminated between H69AR cells, in which high levels of MRP are detected in essentially all cells, and parental H69 cells, in which the 190 kDa protein is not detected. A small difference in immunofluorescent labelling was also observed between the parental H69 cells and revertant H69PR cells, which express slightly higher levels of MRP than H69 cells. When MRP-transfected T5 cells were labelled with MAb QCRL-3, an asymmetric distribution of relative fluorescence intensity was observed. Since T5 cells are an uncloned population, individual cells within this population are likely to express different levels of MRP. Similar histograms were obtained with MAbs QCRL-1 and QCRL-2.

Using indirect immunofluorescence microscopy, all three MAbs were observed to react intensely with resistant T5 and H69AR cells but not with C1 and H69 cells. Labelling of H69AR cells was uniform while staining of T5 cells was somewhat heterogeneous, consistent with the flow cytometric analyses. Both MRP positive T5 cells and H69AR cells showed predominantly plasma membrane labelling. These data are consistent with subcellular fractionation studies which also indicate a predominantly plasma membrane localization of MRP in these cells. However, some granular cytoplasmic staining was also evident in the T5 and H69AR cells, suggesting that some MRP may be associated with intracellular membranes.

In an attempt to generate mAbs reactive against conformational epitopes of MRP, denaturing detergents were not used in the preparation of the membranes used for immunization and or in the immunodot blotting screening procedure. Only one of the five MAbs obtained, MAb QCRL-1, recognizes a linear epitope, as demonstrated by its reactivity with denatured protein in immunoblots. In contrast, the other four MAbs only detect MRP in non-denaturing immunodot blots or under relatively non-denaturing conditions in immunoprecipitations, and in fixed cells. These observations strongly suggest that these latter MAbs recognize conformation dependent epitopes. Because of its unique ability to detect MRP in immunoblots, it may be inferred that MAb QCRL-1 reacts with an MRP epitope distinct from those recognized by the other four MAbs. The ability of MAbs QCRL-2 and QCRL-3 to immunoprecipitate MRP, while MAbs QCRL-4 and QCRL-6 are unable to do so under the same conditions, suggests that these two pairs of MAbs also recognize at least two different epitopes.

EXAMPLE 9

ISOLATION OF A MOUSE MRP-ENCODING cDNA

In this Example, an MRP-encoding cDNA was isolated from a mouse cDNA library. The following methodologies were used:

Cloning and Sequence Analysis of Murine MRP

A mouse skeletal muscle 5'-stretch plus cDNA Library (Clontech Laboratories, Inc., Palo Alto, Calif.) was screened as described in Sambrook et al. (1989) *Molecular Cloning: A Laboratory Manual*, 2nd edition, Cold Spring Harbor Press, Cold Spring Harbor, N.Y., using a mouse qenomic DNA fragment which was isolated previously from a 129SV-CP mouse genomic library using a human MRP cDNA as a probe. The murine genomic fragment contained an exon corresponding to exon 2 of the human MRP gene. The muscle cDNA library was also screened with a 3' proximal cDNA fragment corresponding to nucleotides 4080 to 5011 of the human MRP mRNA. Approximately $5 \times 10^5$ plaques were screened and 4 positive cDNA clones were selected and plaque purified (clones 14B, 16, 37 and 41). The cDNA inserts of clones 14B (nucleotides 124 to 2111), 16 (nucleotides 1607 to 5888) and 41 (nucleotides 2796 to 5883) were subcloned into a pBluescript vector (Stratagene) and both strands were sequenced using the dideoxy chain termination method and Sequenase version 2.0 (U.S. Biochemicals)

Polymerase Chain Reaction (PCR) Methods

Standard PCR conditions were used to amplify regions of the isolated cDNAs for sequencing (clone 37 nucleotides 1 to 146) or for use as probes in Southern blot analysis. Reverse transcriptase (RT)-PCR using Poly A+ RNA isolated from the L138C3-109 murine mastocytoma cell line was used to confirm the sequence of some regions of the MRP mRNA.

Genomic DNA Preparation and Southern Blot Analysis

Genomic DNA was isolated from CD 1 mice, digested with EcoR1 and subjected to agarose gel electrophoresis. DNA was transferred to Zetaprobe membrane (Biorad, Mississauga, Ontario, Canada), and cross-linked using a W Stratalinker (Stratagene). The blot was prehybridized at 37° C. for 4–6 h in 50% formamide, 5×SSPE, 4×Denhardt's, 0.5% SDS and 100 µg/ml sheared and denatured herring testes DNA. It was then hybridized under the same conditions for 12–16 h with a [$\gamma$-$^{32}$P]dATP-labelled MRP cDNA fragment, and subsequently washed four times for 15 min in 2×SSC and 0.1% SDS at 42° C. In some experiments, higher stringency washes were also carried out in 2×SSC or 0.1× SSC and 0.1% SDS at 52° C.

RNA Isolation and Northern Blot Analysis

Total RNA was obtained using TRIzoL reagent (Gibco BRL, Toronto, Ontario, Canada), from various tissues dissected from sexually mature CD 1 mice as well as the murine mastocytoma L138C3-109 cells and Hela cells (T5) transfected with a human MRP expression vector. PolyA enriched RNA was subsequently isolated from the total RNA using either a PoLyATtract mRNA isolation system (Promega, Madison, Wis.) or a Micro-FastTrack RNA isolation kit (Invitrogen, San Diego, Calif.). RNA was separated by electrophoresis on formaldehyde-agarose denaturing gels (Fourney, R. M. et al. (1988) *Focus* 10:5–7), blotted, prehybridized at 42° C. for 4–6 h and hybridized at 42° C. for 12–16 hours with [$\gamma$-$^{32}$P]-cDNA fragments under standard conditions (NEN Products, Boston, Mass.). The blot was washed four times with 0.1×SSC and 0.1% SDS for 15 min at 52° C. and then exposed to film. Blots were subsequently hybridized without stripping with cDNAs corresponding to glyceraldehyde-3-phosphate dehydrogenase (GAPDH) and/or β-actin. Relative levels of MRP and β-actin were determined by densitometric analysis of the autoradiographs (Molecular Dynamics, Sunnyvale, Calif.).

In Situ Hybridization

Single stranded antisense RNA probes were produced by run-off in vitro transcription in the presence of digoxygenin-UTP (Boehringer-Mannheim). The template for the MRP probe was a 1593 bp EcoRI-SacI fragment of clone 14B which corresponds to nucleotides 119 to 1610 of the murine mRNA, subcloned in pBluescript II SK+ (Stratagene). As a control, tissue sections were hybridized with an antisense probe complementary to the coding region of rabbit β-globin. Cryosections (6–8 µm) were mounted onto poly-L-lysine coated glass microscope slides, fixed for 1 h in 4% paraformaldehyde, treated with proteinase K (1 µg/µl for 10–20 min), and post-fixed in 4% paraformaldehyde for 20 min, before being hybridized overnight in 50% formamide, 5×SSC, 0.5 mg/ml tRNA, 0.005% heparin, 0.1% Tween-20 and 250 µg/ml denatured herring testes DNA. The next day the slides were washed twice in 2×SSC for 30 min each, at room temperature and once for 30 min at 65° C., followed by a 30 min high stringency wash at 65° C. in 0.1×SSC/0.1% SDS.

Unhybridized probe still remaining was removed by 30 min digestion with 20 µg/ml RNase A (Pharmacia) at 37° C., followed by 15 min in 2×SSC/0.1% SDS at 65° C., and 30 min in 1×SSC/0.1% SDS at 65° C. Hybridized probe was detected with an alkaline phosphatase conjugated sheep anti-digoxigenin antibody (Boehringer-Mannheim) and the chromogenic substrates nitro blue tetrazolium and 5-bromo-4-chloro-3-indolyl-phosphate.

RESULTS

Molecular Cloning of a Mouse MRP cDNA

Preliminary Northern blotting analyses of RNA from a number of murine tissues was carried out to identify an appropriate source from which to clone the murine MRP homologue. Analyses using a human MRP cDNA probe revealed a single cross-hybridizing mRNA species of 6.0–6.4 kb that was present at relatively high levels in skeletal muscle. A mouse skeletal muscle cDNA library was then screened to isolate clones containing cDNA fragments corresponding to the cross-hybridizing murine mRNA. The first probe used for screening was a DNA fragment isolated from a 129SV-CP mouse genomic library that contained a putative exon which was 90% identical to nucleotides 48 to 226 of the coding region of human MRP mRNA. The second was a 3' proximal human cDNA fragment encompassing nucleotides 3881 to 4815 of the MRP mRNA. Sequencing of the 4 cDNA clones isolated revealed a potential open reading frame of 1528 amino acids which was 88% identical with the coding sequence of the human MRP mRNA. This open reading frame was interrupted in one clone by a stretch of 65 nucleotides bracketed by potential intron acceptor and donor sites. The region spanning the possible intron was amplified by RT-PCR using RNA from a mouse mastocytoma cell line which has been shown previously to express relatively high levels of MRP. Sequencing of the RT-PCR product confirmed that the additional sequence present in clone 14B was not present in the majority of the mRNA and most probably represents an unspliced intron. The most 5' proximal of the clones isolated, clone 37, contained a methionine codon at a position corresponding to the initiator methionine of human MRP plus 5 nucleotides of 5' untranslated sequence. In addition to an open reading frame of 1528 amino acids, the compiled sequence contained a 3' untranslated region of 1295 nucleotides. The nucleotide and encoded amino acid sequences of the isolated mouse MRP cDNA clone are shown in SEQ ID NOs: 5 and 6, respectively.

Comparison of Mouse and Human MRP Amino Acid Sequences

The deduced amino acid sequences of the murine protein and human MRP are 88% identical. The sequences of predicted Walker A and B motifs in both the NH2- and COOH-proximal nucleotide-binding folds (NBF) of the two proteins was completely conserved, as is the atypical spacing of these motifs in the $NH_2$-proximal domain. The highest variability in amino acid sequence between human MRP and the cloned murine mRNA was found to occur in the linker region which joins the two functional halves of the molecule. The most striking similarity found between murine and human MRP was the complete conservation of 114 amino acids between positions 1123 and 1236 of the murine MRP coding sequence and positions 1126 and 1139 of the human MRP coding sequence.

Analysis of the Tissue Distribution of Murine MRP mRNA

Using clone 16 as a probe, an mRNA of approximately 6–6.4 kb was detected at variable levels in all tissues examined. The highest levels of expression were in testes, lung, kidney, heart and skeletal muscle. The murine mRNA was detectable in liver only when the quantity of liver Poly A+ mRNA was increased 4-fold. This tissue profile of expression is similar to that of human MRP. The spatial pattern of expression of the cloned murine mRNA in testis and lung was also analyzed by in situ hybridization. In the testis, detection of the mRNA was restricted to germ cells. Examination of cross sections of the testis revealed that positive staining was confined to seminiferous tubules. It was also observed at low magnification that only a subset of the seminiferous tubules was stained and that staining intensity within this subset was highly variable. On the basis of their location within the seminiferous epithelium, the positively staining cells were identified as haploid spermatids. The pattern of mRNA localization observed herein indicates that expression is developmentally regulated in the testis, and that spermatogenic cells accumulate the mRNA in a stage specific fashion. The expression of the cloned murine MRP mRNA in spermatids suggests a role in the dramatic morphogenetic transformation that takes place during spermiogenesis.

In the lung high levels of the cloned murine MRP mRNA were detected in the epithelia lining both bronchi and bronchioles.

Identical results were obtained when hybridization was carried out with another of the isolated cDNAs as a probe, corresponding to a region of the transcript distinct from 14B. The specificity of the staining pattern was also assessed by hybridization with the rabbit β-globin probe. This resulted in only a low level of background staining, without any discernible pattern, in both testis and lung.

Genomic Southern Blot Analysis

To look for the existence of other genes closely related to the gene from which the murine mRNA was transcribed Southern blot analysis was performed with mouse genomic DNA. This was performed under low stringency conditions using a PCR product encompassing nucleotides 53 to 231 of the coding sequence of the murine mRNA as a probe. Since the probe did not contain any EcoR1 restriction sites and there are no EcoR1 restriction sites in the murine mRNA coding sequence, the genomic fragment(s) recognized by the probe would have been generated by cleavage within intron sequence. Conservation of restriction sites in intron sequence among closely related family members is unlikely, indicating that should a family of genes exist, the probe would have been expected to hybridize to more than one fragment under the conditions used. However, the probe hybridized to a single discrete fragment in an EcoR1 genomic digest suggesting that in contrast to the murine Pgps, the isolated murine mRNA does not belong to a multigene family.

Forming part of the present disclosure is the appended Sequence Listing for the multidrug resistance proteins of the present invention.

EQUIVALENTS

Those skilled in the art will recognize, or be able to ascertain using no more than routine experimentation, many equivalents of the specific embodiments of the invention described herein. Such equivalents are intended to be encompassed by the following claims.

We claim:

1. A method for identifying a multidrug resistant tumor cell comprising:

contacting the tumor cell with an antibody or antigen-binding fragment thereof which binds to a multidrug resistance protein expressed by the cell, wherein the antibody or antigen-binding fragment thereof is coupled to a detectable label; and detecting the detectable label bound to the tumor cell;

wherein the multidrug resistance protein is encoded by: (i) the nucleotide sequence of SEQ ID NO: 1 or (ii) a natural allelic variant of SEQ ID NO: 1;

wherein the protein confers multidrug resistance on a drug sensitive mammalian cell when the protein is expressed by the cell;

wherein the antibody or antigen-binding fragment thereof does not bind only to a nucleotide binding fold of the protein corresponding to amino acid residues from about 661 to about 810 of SEQ ID NO: 2 or only to a nucleotide binding fold of the protein corresponding to amino acid residues from about 1310 to about 1469 of SEQ ID NO: 2; and wherein the antibody or antigen-binding fragment thereof does not bind substantially to P-glycoprotein.

2. A diagnostic kit for identifying multidrug resistant tumor cells comprising:

an antibody or antigen-binding fragment thereof for incubation with a sample of tumor cells, wherein said antibody or antigen-binding fragment thereof binds to a multidrug resistance protein encoded by: (i) the nucleotide sequence of SEQ ID NO: 1 or (ii) a natural allelic variant of SEQ ID NO: 1; said antibody or antigen-binding fragment thereof does not bind only to a nucleotide binding fold of the protein corresponding to amino add residues from about 661 to about 810 of SEQ ID NO: 2 or only to a nucleotide binding fold of the protein corresponding to amino acid residues from about 1310 to about 1469 of SEQ ID NO: 2; and said antibody or antigen-binding fragment thereof does not bind substantially to P-glycoprotein;

means for detecting the antibody or antigen-binding fragment thereof bound to the protein, unbound protein or unbound antibody or antigen-binding fragment thereof;

means for determining the amount of protein in the sample, and means for comparing the amount of protein in the sample with a standard.

3. A method for identifying a multidrug resistant tumor cell comprising:

contacting the tumor cell with an antibody or antigen-binding fragment thereof which binds to a multidrug resistance protein expressed by the cell, wherein the antibody or antigen-binding fragment thereof is coupled to a detectable label; and detecting the detectable label bound to the tumor cell;

wherein the multidrug resistance protein is encoded by: (i) the nucleotide sequence of SEQ ID NO: 3 or (ii) a natural allelic variant of SEQ ID NO: 3;

wherein the protein confers multidrug resistance on a drug sensitive mammalian cell when the protein is expressed by the cell;

wherein the antibody or antigen-binding fragment thereof does not bind only to a nucleotide binding fold of the protein corresponding to amino acid residues from about 661 to about 810 of SEQ ID NO: 4 or only to a nucleotide binding fold of the protein corresponding to amino acid residues from about 1310 to about 1469 of SEQ ID NO: 4; and wherein the antibody or antigen-binding fragment thereof does not bind substantially to P-glycoprotein.

4. A method for identifying a multidrug resistant tumor cell comprising:

contacting the tumor cell with an antibody or antigen-binding fragment thereof which binds to a multidrug resistance protein expressed by the cell, wherein the antibody or antigen-binding fragment thereof is coupled to a detectable label; and detecting the detectable label bound to the tumor cell;

wherein the multidrug resistance protein is encoded by: (i) the nucleotide sequence of SEQ ID NO: 5 or (ii) a natural allelic variant of SEQ ID NO: 5;

wherein the protein confers multidrug resistance on a drug sensitive mammalian cell when the protein is expressed by the cell;

wherein the antibody or antigen-binding fragment thereof does not bind only to a nucleotide binding fold of the protein corresponding to amino acid residues from about 661 to about 810 of SEQ ID NO: 6 or only to a nucleotide binding fold of the protein corresponding to amino acid residues from about 1307 to about 1466 of SEQ ID NO: 6; and wherein the antibody or antigen-binding fragment thereof does not bind substantially to P-glycoprotein.

5. A diagnostic kit for identifying multidrug resistant tumor cells comprising:

an antibody or antigen-binding fragment thereof for incubation with a sample of tumor cells, wherein said antibody or antigen-binding fragment thereof binds to a multidrug resistance protein encoded by: (i) the nucleotide sequence of SEQ ID NO: 3 or (ii) a natural allelic variant of SEQ ID NO: 3; said antibody or antigen-binding fragment thereof does not bind only to a nucleotide binding fold of the protein corresponding to amino acid residues from about 661 to about 810 of SEQ ID NO: 4 or only to a nucleotide binding fold of the protein corresponding to amino acid residues from about 1310 to about 1469 of SEQ ID NO: 4; and said antibody or antigen-binding fragment thereof does not bind substantially to P-glycoprotein;

means for detecting the antibody or antigen-binding fragment thereof bound to the protein, unbound protein or unbound antibody or antigen-binding fragment thereof;

means for determining the amount of protein in the sample; and means for comparing the amount of protein in the sample with a standard.

6. A diagnostic kit for identifying multidrug resistant tumor cells comprising:

an antibody or antigen-binding fragment thereof for incubation with a sample of tumor cells, wherein said antibody or antigen-binding fragment thereof binds to a multidrug resistance protein encoded by: (i) the nucleotide sequence of SEQ ID NO: 5 or (ii) a natural allelic variant of SEQ ID NO: 5; said antibody or antigen-binding fragment thereof does not bind only to a nucleotide binding fold of the protein corresponding to amino acid residues from about 661 to about 810 of SEQ ID NO: 6 or only to a nucleotide binding fold of the protein corresponding to amino acid residues from about 1307 to about 1466 of SEQ ID NO: 6; and said antibody or antigen-binding fragment thereof does not bind substantially to P-glycoprotein;

means for detecting the antibody or antigen-binding fragment thereof bound to the protein, unbound protein or unbound antibody or antigen-binding fragment thereof;

means for determining the amount of protein in the sample; and means for comparing the amount of protein in the sample with a standard.

7. The method of claim 1, 3 or 4, wherein the antibody or antigen-binding fragment thereof is a monoclonal antibody or antigen-binding fragment thereof.

8. The method of claim 7, wherein the monoclonal antibody is produced by a hybridoma selected from the group consisting of QCRL-1 having ATCC accession number HB 11765 and QCRL-3 having ATCC accession number HB 11766.

9. The method of claim 1, 3 or 4, wherein the antibody or antigen-binding fragment thereof is a bispecific antibody.

10. The method of claim 1, 3 or 4, wherein the antibody or antigen-binding fragment thereof is a tetrameric antibody complex.

11. The method of claim 1, 3 or 4, wherein the detectable label is selected from the group consisting of a fluorescent label an enzyme and a radioactive label.

12. The diagnostic kit of claim 2, 5 or 6, wherein the antibody or antigen-binding fragment thereof is a monoclonal antibody or an antigen-binding fragment thereof.

13. The diagnostic kit of claim 12, wherein the monoclonal antibody is produced by a hybridoma selected from the group consisting of QCRL-1 having ATCC accession number HB 11765 and QCRL-3 having ATCC accession number HB 11766.

14. The diagnostic kit of claim 2, 5 or 6, wherein the detecting means comprises a detectable label.

15. The diagnostic kit of claim 14, wherein the detectable label is selected from the group consisting of a fluorescent label, an enzyme and a radioactive label.

16. The diagnostic kit of claim 2, 5 or 6, wherein the antibody or antigen-binding fragment thereof is a bispecific antibody.

17. The diagnostic kit of claim 2, 5 or 6, wherein the antibody or antigen-binding fragment thereof is a tetrameric antibody complex.

* * * * *

UNITED STATES PATENT AND TRADEMARK OFFICE
CERTIFICATE OF CORRECTION

PATENT NO. : 5,882,875  
DATED : March 16, 1999  
INVENTOR(S) : Roger G. Deeley and Susan P.C. Cole Page 1 of 2

Figure 9A:
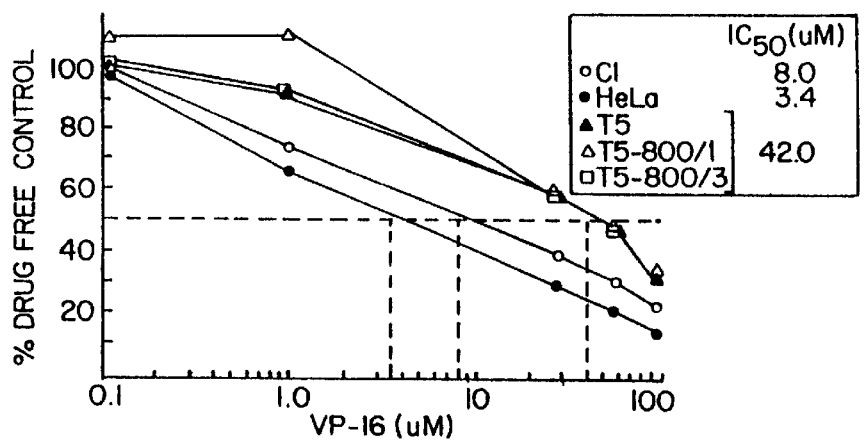
FIG. 9 is a graph depicting the relative cytotoxicity of VP-16, vincristine and cisplatin on MRP-transfected HeLa cell populations (T2, T5), a clone of the T5 population (T5-5), untransfected HeLa cells and HeLa cells transfected with the parental expression vector (C1).
Figure 9B:
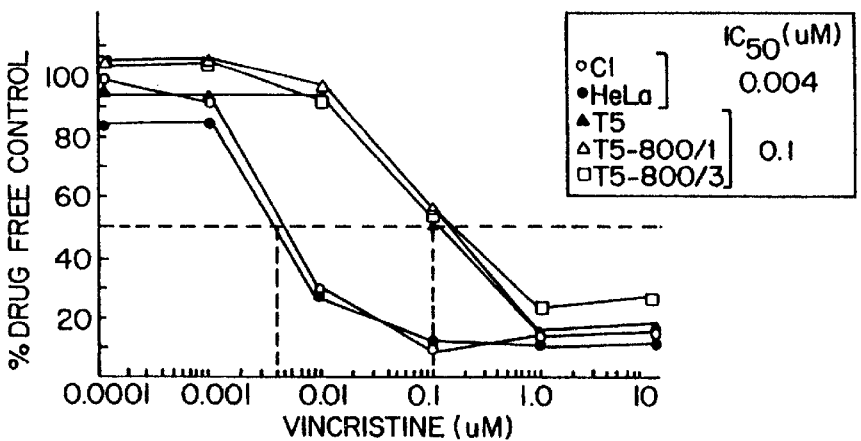
Figure 9C:
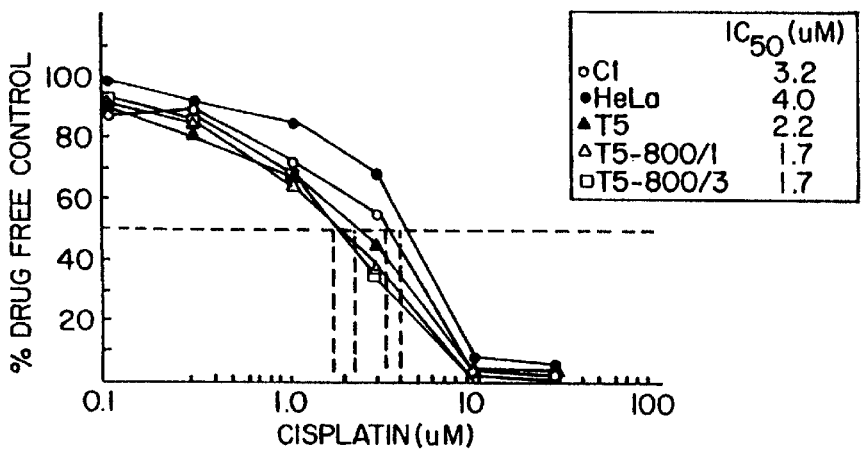

It is certified that error appears in the above-identified patent and that said Letters Patent is hereby corrected as shown below:

At column 4, line 56; replace "Figure 3A is" with --Figures 3A-1 to 3A-5 show--.
At column 4, line 59; replace "Figure 3B is" with --Figures 3B and 3B-1 show--.
At column 5, line 37; replace "Figure 9 is a graph depicting" with --Figures 9A to 9C show--.
At column 5, line 38; replace "cisplatin" with --cisplatin, respectively,--.
At column 5, line 38; replace "(T2, T5)" with --(T5-800/1, T5-800/3)--.
At column 5, line 39; replace "(T5-5)" with --(T5)--.
At column 34, line 17; replace "(Figure 3A)" with --(Figures 3A-1 to 3A-5)--.
At column 34, line 24; replace "Figure 3A" with --Figures 3A-1 to 3A-5--.

UNITED STATES PATENT AND TRADEMARK OFFICE
CERTIFICATE OF CORRECTION

PATENT NO. : 5,882,875

DATED : March 16, 1999

INVENTOR(S) : Roger G. Deeley and Susan P.C. Cole

It is certified that error appears in the above-identified patent and that said Letters Patent is hereby corrected as shown below:

At column 34, line 44; replace "Figure 3B" with --Figures 3B and 3B-1-- (both occurrences).
At column 34, line 53; replace "Figure 3A" with --Figures 3A-1 to 3A-5--.
At column 40, line 9; after "cross-resistance to" insert --VP-16 (an epipodophyllotoxin),--.
At column 40, line 10; delete "VP-16 (an epipodophyllotoxin)".
At column 40, line 11; replace "(Fig. 9)" with --(Figs. 9A to 9C)--.
At column 40, line 15; replace "Δ" with --▲--.

Signed and Sealed this

Twenty-first Day of September, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 5011 base pairs
        ( B ) TYPE: nucleic acid

```
              ( C ) STRANDEDNESS: double
              ( D ) TOPOLOGY: linear ( i i ) MOLECULE TYPE: cDNA ( i x ) FEATURE:
              ( A ) NAME/KEY: CDS
              ( B ) LOCATION: 196..4788

( x i ) SEQUENCE DESCRIPTION: SEQ ID NO:1:
```

| | | | | | |
|---|---|---|---|---|---|
| CAGGCGGCGT | TGCGGCCCCG | GCCCCGGCTC | CCTGCGCCGC | CGCCGCCGCC | GCCGCCGCCG | 60 |
| CCGCCGCCGC | CGCCGCCAGC | GCTAGCGCCA | GCAGCCGGGC | CCGATCACCC | GCCGCCCGGT | 120 |
| GCCCGCCGCC | GCCCGCGCCA | GCAACCGGGC | CCGATCACCC | GCCGCCCGGT | GCCCGCCGCC | 180 |

```
GCCCGCGCCA  CCGGC  ATG  GCG  CTC  CGG  GGC  TTC  TGC  AGC  GCC  GAT  GGC  TCC                231
                   Met  Ala  Leu  Arg  Gly  Phe  Cys  Ser  Ala  Asp  Gly  Ser
                    1                  5                              10

GAC  CCG  CTC  TGG  GAC  TGG  AAT  GTC  ACG  TGG  AAT  ACC  AGC  AAC  CCC  GAC              279
Asp  Pro  Leu  Trp  Asp  Trp  Asn  Val  Thr  Trp  Asn  Thr  Ser  Asn  Pro  Asp
               15                       20                       25

TTC  ACC  AAG  TGC  TTT  CAG  AAC  ACG  GTC  CTC  GTG  TGG  GTG  CCT  TGT  TTT              327
Phe  Thr  Lys  Cys  Phe  Gln  Asn  Thr  Val  Leu  Val  Trp  Val  Pro  Cys  Phe
          30                       35                       40

TAC  CTC  TGG  GCC  TGT  TTC  CCC  TTC  TAC  TTC  CTC  TAT  CTC  TCC  CGA  CAT              375
Tyr  Leu  Trp  Ala  Cys  Phe  Pro  Phe  Tyr  Phe  Leu  Tyr  Leu  Ser  Arg  His
45                       50                       55                       60

GAC  CGA  GGC  TAC  ATT  CAG  ATG  ACA  CCT  CTC  AAC  AAA  ACC  AAA  ACT  GCC              423
Asp  Arg  Gly  Tyr  Ile  Gln  Met  Thr  Pro  Leu  Asn  Lys  Thr  Lys  Thr  Ala
                    65                       70                       75

TTG  GGA  TTT  TTG  CTG  TGG  ATC  GTC  TGC  TGG  GCA  GAC  CTC  TTC  TAC  TCT              471
Leu  Gly  Phe  Leu  Leu  Trp  Ile  Val  Cys  Trp  Ala  Asp  Leu  Phe  Tyr  Ser
               80                       85                       90

TTC  TGG  GAA  AGA  AGT  CGG  GGC  ATA  TTC  CTG  GCC  CCA  GTG  TTT  CTG  GTC              519
Phe  Trp  Glu  Arg  Ser  Arg  Gly  Ile  Phe  Leu  Ala  Pro  Val  Phe  Leu  Val
          95                      100                      105

AGC  CCA  ACT  CTC  TTG  GGC  ATC  ACC  ACG  CTG  CTT  GCT  ACC  TTT  TTA  ATT              567
Ser  Pro  Thr  Leu  Leu  Gly  Ile  Thr  Thr  Leu  Leu  Ala  Thr  Phe  Leu  Ile
     110                      115                      120

CAG  CTG  GAG  AGG  AGG  AAG  GGA  GTT  CAG  TCT  TCA  GGG  ATC  ATG  CTC  ACT              615
Gln  Leu  Glu  Arg  Arg  Lys  Gly  Val  Gln  Ser  Ser  Gly  Ile  Met  Leu  Thr
125                      130                      135                      140

TTC  TGG  CTG  GTA  GCC  CTA  GTG  TGT  GCC  CTA  GCC  ATC  CTG  AGA  TCC  AAA              663
Phe  Trp  Leu  Val  Ala  Leu  Val  Cys  Ala  Leu  Ala  Ile  Leu  Arg  Ser  Lys
                    145                      150                      155

ATT  ATG  ACA  GCC  TTA  AAA  GAG  GAT  GCC  CAG  GTG  GAC  CTG  TTT  CGT  GAC              711
Ile  Met  Thr  Ala  Leu  Lys  Glu  Asp  Ala  Gln  Val  Asp  Leu  Phe  Arg  Asp
               160                      165                      170

ATC  ACT  TTC  TAC  GTC  TAC  TTT  TCC  CTC  TTA  CTC  ATT  CAG  CTC  GTC  TTG              759
Ile  Thr  Phe  Tyr  Val  Tyr  Phe  Ser  Leu  Leu  Leu  Ile  Gln  Leu  Val  Leu
          175                      180                      185

TCC  TGT  TTC  TCA  GAT  CGC  TCA  CCC  CTG  TTC  TCG  GAA  ACC  ATC  CAC  GAC              807
Ser  Cys  Phe  Ser  Asp  Arg  Ser  Pro  Leu  Phe  Ser  Glu  Thr  Ile  His  Asp
     190                      195                      200

CCT  AAT  CCC  TGC  CCA  GAG  TCC  AGC  GCT  TCC  TTC  CTG  TCG  AGG  ATC  ACC              855
Pro  Asn  Pro  Cys  Pro  Glu  Ser  Ser  Ala  Ser  Phe  Leu  Ser  Arg  Ile  Thr
205                      210                      215                      220

TTC  TGG  TGG  ATC  ACA  GGG  TTG  ATT  GTC  CGG  GGC  TAC  CGC  CAG  CCC  CTG              903
Phe  Trp  Trp  Ile  Thr  Gly  Leu  Ile  Val  Arg  Gly  Tyr  Arg  Gln  Pro  Leu
                    225                      230                      235

GAG  GGC  AGT  GAC  CTC  TGG  TCC  TTA  AAC  AAG  GAG  GAC  ACG  TCG  GAA  CAA              951
Glu  Gly  Ser  Asp  Leu  Trp  Ser  Leu  Asn  Lys  Glu  Asp  Thr  Ser  Glu  Gln
               240                      245                      250
```

| | | | | | | | | | | | | | | | | |
|---|---|---|---|---|---|---|---|---|---|---|---|---|---|---|---|---|
| GTC | GTG | CCT | GTT | TTG | GTA | AAG | AAC | TGG | AAG | AAG | GAA | TGC | GCC | AAG | ACT | 999 |
| Val | Val | Pro 255 | Val | Leu | Val | Lys | Asn 260 | Trp | Lys | Lys | Glu | Cys 265 | Ala | Lys | Thr | |
| AGG | AAG | CAG | CCG | GTG | AAG | GTT | GTG | TAC | TCC | TCC | AAG | GAT | CCT | GCC | CAG | 1047 |
| Arg | Lys 270 | Gln | Pro | Val | Lys | Val 275 | Val | Tyr | Ser | Ser | Lys 280 | Asp | Pro | Ala | Gln | |
| CCG | AAA | GAG | AGT | TCC | AAG | GTG | GAT | GCG | AAT | GAG | GAG | GTG | GAG | GCT | TTG | 1095 |
| Pro 285 | Lys | Glu | Ser | Ser | Lys 290 | Val | Asp | Ala | Asn | Glu 295 | Glu | Val | Glu | Ala | Leu 300 | |
| ATC | GTC | AAG | TCC | CCA | CAG | AAG | GAG | TGG | AAC | CCC | TCT | CTG | TTT | AAG | GTG | 1143 |
| Ile | Val | Lys | Ser | Pro 305 | Gln | Lys | Glu | Trp | Asn 310 | Pro | Ser | Leu | Phe | Lys 315 | Val | |
| TTA | TAC | AAG | ACC | TTT | GGG | CCC | TAC | TTC | CTC | ATG | AGC | TTC | TTC | TTC | AAG | 1191 |
| Leu | Tyr | Lys | Thr 320 | Phe | Gly | Pro | Tyr | Phe 325 | Leu | Met | Ser | Phe | Phe 330 | Phe | Lys | |
| GCC | ATC | CAC | GAC | CTG | ATG | ATG | TTT | TCC | GGG | CCG | CAG | ATC | TTA | AAG | TTG | 1239 |
| Ala | Ile | His 335 | Asp | Leu | Met | Met | Phe 340 | Ser | Gly | Pro | Gln | Ile 345 | Leu | Lys | Leu | |
| CTC | ATC | AAG | TTC | GTG | AAT | GAC | ACG | AAG | GCC | CCA | GAC | TGG | CAG | GGC | TAC | 1287 |
| Leu | Ile | Lys 350 | Phe | Val | Asn | Asp | Thr 355 | Lys | Ala | Pro | Asp | Trp 360 | Gln | Gly | Tyr | |
| TTC | TAC | ACC | GTG | CTG | CTG | TTT | GTC | ACT | GCC | TGC | CTG | CAG | ACC | CTC | GTG | 1335 |
| Phe 365 | Tyr | Thr | Val | Leu | Leu 370 | Phe | Val | Thr | Ala | Cys 375 | Leu | Gln | Thr | Leu | Val 380 | |
| CTG | CAC | CAG | TAC | TTC | CAC | ATC | TGC | TTC | GTC | AGT | GGC | ATG | AGG | ATC | AAG | 1383 |
| Leu | His | Gln | Tyr | Phe 385 | His | Ile | Cys | Phe | Val 390 | Ser | Gly | Met | Arg | Ile 395 | Lys | |
| ACC | GCT | GTC | ATT | GGG | GCT | GTC | TAT | CGG | AAG | GCC | CTG | GTG | ATC | ACC | AAT | 1431 |
| Thr | Ala | Val | Ile 400 | Gly | Ala | Val | Tyr | Arg 405 | Lys | Ala | Leu | Val | Ile 410 | Thr | Asn | |
| TCA | GCC | AGA | AAA | TCC | TCC | ACG | GTC | GGG | GAG | ATT | GTC | AAC | CTC | ATG | TCT | 1479 |
| Ser | Ala | Arg 415 | Lys | Ser | Ser | Thr | Val 420 | Gly | Glu | Ile | Val | Asn 425 | Leu | Met | Ser | |
| GTG | GAC | GCT | CAG | AGG | TTC | ATG | GAC | TTG | GCC | ACG | TAC | ATT | AAC | ATG | ATC | 1527 |
| Val | Asp | Ala 430 | Gln | Arg | Phe | Met | Asp 435 | Leu | Ala | Thr | Tyr | Ile 440 | Asn | Met | Ile | |
| TGG | TCA | GCC | CCC | CTG | CAA | GTC | ATC | CTT | GCT | CTC | TAC | CTC | CTG | TGG | CTG | 1575 |
| Trp 445 | Ser | Ala | Pro | Leu | Gln 450 | Val | Ile | Leu | Ala | Leu 455 | Tyr | Leu | Leu | Trp | Leu 460 | |
| AAT | CTG | GGC | CCT | TCC | GTC | CTG | GCT | GGA | GTG | GCG | GTG | ATG | GTC | CTC | ATG | 1623 |
| Asn | Leu | Gly | Pro | Ser 465 | Val | Leu | Ala | Gly | Val 470 | Ala | Val | Met | Val | Leu 475 | Met | |
| GTG | CCC | GTC | AAT | GCT | GTG | ATG | GCG | ATG | AAG | ACC | AAG | ACG | TAT | CAG | GTG | 1671 |
| Val | Pro | Val | Asn 480 | Ala | Val | Met | Ala | Met 485 | Lys | Thr | Lys | Thr | Tyr 490 | Gln | Val | |
| GCC | CAC | ATG | AAG | AGC | AAA | GAC | AAT | CGG | ATC | AAG | CTG | ATG | AAC | GAA | ATT | 1719 |
| Ala | His | Met 495 | Lys | Ser | Lys | Asp | Asn 500 | Arg | Ile | Lys | Leu | Met 505 | Asn | Glu | Ile | |
| CTC | AAT | GGG | ATC | AAA | GTG | CTA | AAG | CTT | TAT | GCC | TGG | GAG | CTG | GCA | TTC | 1767 |
| Leu | Asn | Gly 510 | Ile | Lys | Val | Leu | Lys 515 | Leu | Tyr | Ala | Trp | Glu 520 | Leu | Ala | Phe | |
| AAG | GAC | AAG | GTG | CTG | GCC | ATC | AGG | CAG | GAG | GAG | CTG | AAG | GTG | CTG | AAG | 1815 |
| Lys | Asp 525 | Lys | Val | Leu | Ala | Ile 530 | Arg | Gln | Glu | Glu | Leu 535 | Lys | Val | Leu | Lys 540 | |
| AAG | TCT | GCC | TAC | CTG | TCA | GCC | GTG | GGC | ACC | TTC | ACC | TGG | GTC | TGC | ACG | 1863 |
| Lys | Ser | Ala | Tyr | Leu 545 | Ser | Ala | Val | Gly | Thr 550 | Phe | Thr | Trp | Val | Cys 555 | Thr | |
| CCC | TTT | CTG | GTG | GCC | TTG | TGC | ACA | TTT | GCC | GTC | TAC | GTG | ACC | ATT | GAC | 1911 |
| Pro | Phe | Leu | Val 560 | Ala | Leu | Cys | Thr | Phe 565 | Ala | Val | Tyr | Val | Thr 570 | Ile | Asp | |

| | | | | | | | | | | | | | | | | |
|---|---|---|---|---|---|---|---|---|---|---|---|---|---|---|---|---|
| GAG | AAC | AAC | ATC | CTG | GAT | GCC | CAG | ACA | GCC | TTC | GTG | TCT | TTG | GCC | TTG | 1959 |
| Glu | Asn | Asn | Ile | Leu | Asp | Ala | Gln | Thr | Ala | Phe | Val | Ser | Leu | Ala | Leu | |
| | | 575 | | | | | 580 | | | | | 585 | | | | |
| TTC | AAC | ATC | CTC | CGG | TTT | CCC | CTG | AAC | ATT | CTC | CCC | ATG | GTC | ATC | AGC | 2007 |
| Phe | Asn | Ile | Leu | Arg | Phe | Pro | Leu | Asn | Ile | Leu | Pro | Met | Val | Ile | Ser | |
| | 590 | | | | | 595 | | | | | 600 | | | | | |
| AGC | ATC | GTG | CAG | GCG | AGT | GTC | TCC | CTC | AAA | CGC | CTG | AGG | ATC | TTT | CTC | 2055 |
| Ser | Ile | Val | Gln | Ala | Ser | Val | Ser | Leu | Lys | Arg | Leu | Arg | Ile | Phe | Leu | |
| 605 | | | | | 610 | | | | | 615 | | | | | 620 | |
| TCC | CAT | GAG | GAG | CTG | GAA | CCT | GAC | AGC | ATC | GAG | CGA | CGG | CCT | GTC | AAA | 2103 |
| Ser | His | Glu | Glu | Leu | Glu | Pro | Asp | Ser | Ile | Glu | Arg | Arg | Pro | Val | Lys | |
| | | | | 625 | | | | | 630 | | | | | 635 | | |
| GAC | GGC | GGG | GGC | ACG | AAC | AGC | ATC | ACC | GTG | AGG | AAT | GCC | ACA | TTC | ACC | 2151 |
| Asp | Gly | Gly | Gly | Thr | Asn | Ser | Ile | Thr | Val | Arg | Asn | Ala | Thr | Phe | Thr | |
| | | | 640 | | | | | 645 | | | | | 650 | | | |
| TGG | GCC | AGG | AGC | GAC | CCT | CCC | ACA | CTG | AAT | GGC | ATC | ACC | TTC | TCC | ATC | 2199 |
| Trp | Ala | Arg | Ser | Asp | Pro | Pro | Thr | Leu | Asn | Gly | Ile | Thr | Phe | Ser | Ile | |
| | | 655 | | | | | 660 | | | | | 665 | | | | |
| CCC | GAA | GGT | GCT | TTG | GTG | GCC | GTG | GTG | GGC | CAG | GTG | GGC | TGC | GGA | AAG | 2247 |
| Pro | Glu | Gly | Ala | Leu | Val | Ala | Val | Val | Gly | Gln | Val | Gly | Cys | Gly | Lys | |
| | 670 | | | | | 675 | | | | | 680 | | | | | |
| TTG | TCC | CTG | CTC | TCA | GCC | CTC | TTG | GCT | GAG | ATG | GAC | AAA | GTG | GAG | GGG | 2295 |
| Leu | Ser | Leu | Leu | Ser | Ala | Leu | Leu | Ala | Glu | Met | Asp | Lys | Val | Glu | Gly | |
| 685 | | | | | 690 | | | | | 695 | | | | | 700 | |
| CAC | GTG | GCT | ATC | AAG | GGC | TCC | GTG | GCC | TAT | GTG | CCA | CAG | CAG | GCC | TGG | 2343 |
| His | Val | Ala | Ile | Lys | Gly | Ser | Val | Ala | Tyr | Val | Pro | Gln | Gln | Ala | Trp | |
| | | | | 705 | | | | | 710 | | | | | 715 | | |
| ATT | CAG | AAT | GAT | TCT | CTC | CGA | GAA | AAC | ATC | CTT | TTT | GGA | TGT | CAG | CTG | 2391 |
| Ile | Gln | Asn | Asp | Ser | Leu | Arg | Glu | Asn | Ile | Leu | Phe | Gly | Cys | Gln | Leu | |
| | | | 720 | | | | | 725 | | | | | 730 | | | |
| GAG | GAA | CCA | TAT | TAC | AGG | TCC | GTG | ATA | CAG | GCC | TGT | GCC | CTC | CTC | CCA | 2439 |
| Glu | Glu | Pro | Tyr | Tyr | Arg | Ser | Val | Ile | Gln | Ala | Cys | Ala | Leu | Leu | Pro | |
| | | 735 | | | | | 740 | | | | | 745 | | | | |
| GAC | CTG | GAA | ATC | CTG | CCC | AGT | GGG | GAT | CGG | ACA | GAG | ATT | GGC | GAG | AAG | 2487 |
| Asp | Leu | Glu | Ile | Leu | Pro | Ser | Gly | Asp | Arg | Thr | Glu | Ile | Gly | Glu | Lys | |
| | 750 | | | | | 755 | | | | | 760 | | | | | |
| GGC | GTG | AAC | CTG | TCT | GGG | GGA | CAG | AAG | CAG | CGC | GTG | AGC | CTG | GCC | CGG | 2535 |
| Gly | Val | Asn | Leu | Ser | Gly | Gly | Gln | Lys | Gln | Arg | Val | Ser | Leu | Ala | Arg | |
| 765 | | | | | 770 | | | | | 775 | | | | | 780 | |
| GCC | GTG | TAC | TCC | AAC | GCT | GAC | ATT | TAC | CTC | TTC | GAT | GAT | CCC | CTC | TCA | 2583 |
| Ala | Val | Tyr | Ser | Asn | Ala | Asp | Ile | Tyr | Leu | Phe | Asp | Asp | Pro | Leu | Ser | |
| | | | | 785 | | | | | 790 | | | | | 795 | | |
| GCA | GTG | GAT | GCC | CAT | GTG | GGA | AAA | CAC | ATC | TTT | GAA | AAT | GTG | ATT | GGC | 2631 |
| Ala | Val | Asp | Ala | His | Val | Gly | Lys | His | Ile | Phe | Glu | Asn | Val | Ile | Gly | |
| | | | 800 | | | | | 805 | | | | | 810 | | | |
| CCC | AAG | GGG | ATG | CTG | AAG | AAC | AAG | ACG | CGG | ATC | TTG | GTC | ACG | CAC | AGC | 2679 |
| Pro | Lys | Gly | Met | Leu | Lys | Asn | Lys | Thr | Arg | Ile | Leu | Val | Thr | His | Ser | |
| | | 815 | | | | | 820 | | | | | 825 | | | | |
| ATG | AGC | TAC | TTG | CCG | CAG | GTG | GAC | GTC | ATC | ATC | GTC | ATG | AGT | GGC | GGC | 2727 |
| Met | Ser | Tyr | Leu | Pro | Gln | Val | Asp | Val | Ile | Ile | Val | Met | Ser | Gly | Gly | |
| | 830 | | | | | 835 | | | | | 840 | | | | | |
| AAG | ATC | TCT | GAG | ATG | GGC | TCC | TAC | CAG | GAG | CTG | CTG | GCT | CGA | GAC | GGC | 2775 |
| Lys | Ile | Ser | Glu | Met | Gly | Ser | Tyr | Gln | Glu | Leu | Leu | Ala | Arg | Asp | Gly | |
| 845 | | | | | 850 | | | | | 855 | | | | | 860 | |
| GCC | TTC | GCT | GAG | TTC | CTG | CGT | ACC | TAT | GCC | AGC | ACA | GAG | CAG | GAG | CAG | 2823 |
| Ala | Phe | Ala | Glu | Phe | Leu | Arg | Thr | Tyr | Ala | Ser | Thr | Glu | Gln | Glu | Gln | |
| | | | | 865 | | | | | 870 | | | | | 875 | | |
| GAT | GCA | GAG | GAG | AAC | GGG | GTC | ACG | GGC | GTC | AGC | GGT | CCA | GGG | AAG | GAA | 2871 |
| Asp | Ala | Glu | Glu | Asn | Gly | Val | Thr | Gly | Val | Ser | Gly | Pro | Gly | Lys | Glu | |
| | | | 880 | | | | | 885 | | | | | 890 | | | |

| | | | | | | | | | | | | | | | |
|---|---|---|---|---|---|---|---|---|---|---|---|---|---|---|---|
| GCA | AAG | CAA | ATG | GAG | AAT | GGC | ATG | CTG | GTG | ACG | GAC | AGT | GCA | GGG | AAG | 2919
| Ala | Lys | Gln | Met | Glu | Asn | Gly | Met | Leu | Val | Thr | Asp | Ser | Ala | Gly | Lys |
| | | 895 | | | | | 900 | | | | | 905 | | | |

| CAA | CTG | CAG | AGA | CAG | CTC | AGC | AGC | TCC | TCC | TCC | TAT | AGT | GGG | GAC | ATC | 2967
| Gln | Leu | Gln | Arg | Gln | Leu | Ser | Ser | Ser | Ser | Ser | Tyr | Ser | Gly | Asp | Ile |
| 910 | | | | | 915 | | | | | 920 | | | | | |

| AGC | AGG | CAC | CAC | AAC | AGC | ACC | GCA | GAA | CTG | CAG | AAA | GCT | GAG | GCC | AAG | 3015
| Ser | Arg | His | His | Asn | Ser | Thr | Ala | Glu | Leu | Gln | Lys | Ala | Glu | Ala | Lys |
| 925 | | | | | 930 | | | | | 935 | | | | | 940 |

| AAG | GAG | GAG | ACC | TGG | AAG | CTG | ATG | GAG | GCT | GAC | AAG | GCG | CAG | ACA | GGG | 3063
| Lys | Glu | Glu | Thr | Trp | Lys | Leu | Met | Glu | Ala | Asp | Lys | Ala | Gln | Thr | Gly |
| | | | | 945 | | | | | 950 | | | | | 955 | |

| CAG | GTC | AAG | CTT | TCC | GTG | TAC | TGG | GAC | TAC | ATG | AAG | GCC | ATC | GGA | CTC | 3111
| Gln | Val | Lys | Leu | Ser | Val | Tyr | Trp | Asp | Tyr | Met | Lys | Ala | Ile | Gly | Leu |
| | | | | 960 | | | | | 965 | | | | | 970 | |

| TTC | ATC | TCC | TTC | CTC | AGC | ATC | TTC | CTT | TTC | ATG | TGT | AAC | CAT | GTG | TCC | 3159
| Phe | Ile | Ser | Phe | Leu | Ser | Ile | Phe | Leu | Phe | Met | Cys | Asn | His | Val | Ser |
| | | 975 | | | | | 980 | | | | | 985 | | | |

| GCG | CTG | GCT | TCC | AAC | TAT | TGG | CTC | AGC | CTC | TGG | ACT | GAT | GAC | CCC | ATC | 3207
| Ala | Leu | Ala | Ser | Asn | Tyr | Trp | Leu | Ser | Leu | Trp | Thr | Asp | Asp | Pro | Ile |
| | 990 | | | | | 995 | | | | | 1000 | | | | |

| GTC | AAC | GGG | ACT | CAG | GAG | CAC | ACG | AAA | GTC | CGG | CTG | AGC | GTC | TAT | GGA | 3255
| Val | Asn | Gly | Thr | Gln | Glu | His | Thr | Lys | Val | Arg | Leu | Ser | Val | Tyr | Gly |
| 1005 | | | | | 1010 | | | | | 1015 | | | | | 1020 |

| GCC | CTG | GGC | ATT | TCA | CAA | GGG | ATC | GCC | GTG | TTT | GGC | TAC | TCC | ATG | GCC | 3303
| Ala | Leu | Gly | Ile | Ser | Gln | Gly | Ile | Ala | Val | Phe | Gly | Tyr | Ser | Met | Ala |
| | | | | 1025 | | | | | 1030 | | | | | 1035 | |

| GTG | TCC | ATC | GGG | GGG | ATC | TTG | GCT | TCC | CGC | TGT | CTG | CAC | GTG | GAC | CTG | 3351
| Val | Ser | Ile | Gly | Gly | Ile | Leu | Ala | Ser | Arg | Cys | Leu | His | Val | Asp | Leu |
| | | | 1040 | | | | | 1045 | | | | | 1050 | | |

| CTG | CAC | AGC | ATC | CTG | CGG | TCA | CCC | ATG | AGC | TTC | TTT | GAG | CGG | ACC | CCC | 3399
| Leu | His | Ser | Ile | Leu | Arg | Ser | Pro | Met | Ser | Phe | Phe | Glu | Arg | Thr | Pro |
| | | 1055 | | | | | 1060 | | | | | 1065 | | | |

| AGT | GGG | AAC | CTG | GTG | AAC | CGC | TTC | TCC | AAG | GAG | CTG | GAC | ACA | GTG | GAC | 3447
| Ser | Gly | Asn | Leu | Val | Asn | Arg | Phe | Ser | Lys | Glu | Leu | Asp | Thr | Val | Asp |
| | 1070 | | | | | 1075 | | | | | 1080 | | | | |

| TCC | ATG | ATC | CCG | GAG | GTC | ATC | AAG | ATG | TTC | ATG | GGC | TCC | CTG | TTC | AAC | 3495
| Ser | Met | Ile | Pro | Glu | Val | Ile | Lys | Met | Phe | Met | Gly | Ser | Leu | Phe | Asn |
| 1085 | | | | | 1090 | | | | | 1095 | | | | | 1100 |

| GTC | ATT | GGT | GCC | TGC | ATC | GTT | ATC | CTG | CTG | GCC | ACG | CCC | ATC | GCC | GCC | 3543
| Val | Ile | Gly | Ala | Cys | Ile | Val | Ile | Leu | Leu | Ala | Thr | Pro | Ile | Ala | Ala |
| | | | | 1105 | | | | | 1110 | | | | | 1115 | |

| ATC | ATC | ATC | CCG | CCC | CTT | GGC | CTC | ATC | TAC | TTC | TTC | GTC | CAG | AGG | TTC | 3591
| Ile | Ile | Ile | Pro | Pro | Leu | Gly | Leu | Ile | Tyr | Phe | Phe | Val | Gln | Arg | Phe |
| | | | 1120 | | | | | 1125 | | | | | 1130 | | |

| TAC | GTG | GCT | TCC | TCC | CGG | CAG | CTG | AAG | CGC | CTC | GAG | TCG | GTC | AGC | CGC | 3639
| Tyr | Val | Ala | Ser | Ser | Arg | Gln | Leu | Lys | Arg | Leu | Glu | Ser | Val | Ser | Arg |
| | | | 1135 | | | | | 1140 | | | | | 1145 | | |

| TCC | CCG | GTC | TAT | TCC | CAT | TTC | AAC | GAG | ACC | TTG | CTG | GGG | GTC | AGC | GTC | 3687
| Ser | Pro | Val | Tyr | Ser | His | Phe | Asn | Glu | Thr | Leu | Leu | Gly | Val | Ser | Val |
| | | 1150 | | | | | 1155 | | | | | 1160 | | | |

| ATT | CGA | GCC | TTC | GAG | GAG | CAG | GAG | CGC | TTC | ATC | CAC | CAG | AGT | GAC | CTG | 3735
| Ile | Arg | Ala | Phe | Glu | Glu | Gln | Glu | Arg | Phe | Ile | His | Gln | Ser | Asp | Leu |
| 1165 | | | | | 1170 | | | | | 1175 | | | | | 1180 |

| AAG | GTG | GAC | GAG | AAC | CAG | AAG | GCC | TAT | TAC | CCC | AGC | ATC | GTG | GCC | AAC | 3783
| Lys | Val | Asp | Glu | Asn | Gln | Lys | Ala | Tyr | Tyr | Pro | Ser | Ile | Val | Ala | Asn |
| | | | | 1185 | | | | | 1190 | | | | | 1195 | |

| AGG | TGG | CTG | GCC | GTG | CGG | CTG | GAG | TGT | GTG | GGC | AAC | TGC | ATC | GTT | CTG | 3831
| Arg | Trp | Leu | Ala | Val | Arg | Leu | Glu | Cys | Val | Gly | Asn | Cys | Ile | Val | Leu |
| | | | 1200 | | | | | 1205 | | | | | 1210 | | |

```
TTT GCT GCC CTG TTT GCG GTG ATC TCC AGG CAC AGC CTC AGT GCT GGC        3879
Phe Ala Ala Leu Phe Ala Val Ile Ser Arg His Ser Leu Ser Ala Gly
1215                    1220                    1225

TTG GTG GGC CTC TCA GTG TCT TAC TCA TTG CAG GTC ACC ACG TAC TTG        3927
Leu Val Gly Leu Ser Val Ser Tyr Ser Leu Gln Val Thr Thr Tyr Leu
    1230                    1235                    1240

AAC TGG CTG GTT CGG ATG TCA TCT GAA ATG GAA ACC AAC ATC GTG GCC        3975
Asn Trp Leu Val Arg Met Ser Ser Glu Met Glu Thr Asn Ile Val Ala
1245                    1250                    1255                    1260

GTG GAG AGG CTC AAG GAG TAT TCA GAG ACT GAG AAG GAG GCG CCC TGG        4023
Val Glu Arg Leu Lys Glu Tyr Ser Glu Thr Glu Lys Glu Ala Pro Trp
                1265                    1270                    1275

CAA ATC CAG GAG ACA CGT CCG CCC AGC AGC TGG CCC CAG GTG GGC CGA        4071
Gln Ile Gln Glu Thr Arg Pro Pro Ser Ser Trp Pro Gln Val Gly Arg
                    1280                    1285                    1290

GTG GAA TTC CGG AAC TAC TGC CTG CGC TAC CGA GAG GAC CTG GAC TTC        4119
Val Glu Phe Arg Asn Tyr Cys Leu Arg Tyr Arg Glu Asp Leu Asp Phe
                1295                    1300                    1305

GTT CTC AGG CAC ATC AAT GTC ACG ATC AAT GGG GGA GAA AAG GTC GGC        4167
Val Leu Arg His Ile Asn Val Thr Ile Asn Gly Gly Glu Lys Val Gly
1310                    1315                    1320

ATC GTG GGG CGG ACG GGA GCT GGG AAG TCG TCC CTG ACC CTG GGC TTA        4215
Ile Val Gly Arg Thr Gly Ala Gly Lys Ser Ser Leu Thr Leu Gly Leu
1325                    1330                    1335                    1340

TTT CGG ATC AAC GAG TCT GCC GAA GGA GAG ATC ATC ATC GAT GGC ATC        4263
Phe Arg Ile Asn Glu Ser Ala Glu Gly Glu Ile Ile Ile Asp Gly Ile
                1345                    1350                    1355

AAC ATC GCC AAG ATC GGC CTG CAC GAC CTC CGC TTC AAG ATC ACC ATC        4311
Asn Ile Ala Lys Ile Gly Leu His Asp Leu Arg Phe Lys Ile Thr Ile
                1360                    1365                    1370

ATC CCC CAG GAC CCT GTT TTG TTT TCG GGT CCC TCG CGA ATG AAC CTG        4359
Ile Pro Gln Asp Pro Val Leu Phe Ser Gly Ser Leu Arg Met Asn Leu
            1375                    1380                    1385

GAC CCA TTC AGC CAG TAC TCG GAT GAA GAA GTC TGG ACG TCC CTG GAG        4407
Asp Pro Phe Ser Gln Tyr Ser Asp Glu Glu Val Trp Thr Ser Leu Glu
        1390                    1395                    1400

CTG GCC CAC CTG AAG GAC TTC GTG TCA GCC CTT CCT GAC AAG CTA GAC        4455
Leu Ala His Leu Lys Asp Phe Val Ser Ala Leu Pro Asp Lys Leu Asp
1405                    1410                    1415                    1420

CAT GAA TGT GCA GAA GGC GGG GAG AAC CTC AGT GTC GGG CAG CGC CAG        4503
His Glu Cys Ala Glu Gly Gly Glu Asn Leu Ser Val Gly Gln Arg Gln
                1425                    1430                    1435

CTT GTG TGC CTA GCC CGG GCC CTG CTG AGG AAG ACG AAG ATC CTT GTG        4551
Leu Val Cys Leu Ala Arg Ala Leu Leu Arg Lys Thr Lys Ile Leu Val
                    1440                    1445                    1450

TTG GAT GAG GCC ACG GCA GCC GTG GAC CTG GAA ACG GAC GAC CTC ATC        4599
Leu Asp Glu Ala Thr Ala Ala Val Asp Leu Glu Thr Asp Asp Leu Ile
                1455                    1460                    1465

CAG TCC ACC ATC CGG ACA CAG TTC GAG GAC TGC ACC GTC CTC ACC ATC        4647
Gln Ser Thr Ile Arg Thr Gln Phe Glu Asp Cys Thr Val Leu Thr Ile
1470                    1475                    1480

GCC CAC CGG CTC AAC ACC ATC ATG GAC TAC ACA AGG GTG ATC GTC TTG        4695
Ala His Arg Leu Asn Thr Ile Met Asp Tyr Thr Arg Val Ile Val Leu
1485                    1490                    1495                    1500

GAC AAA GGA GAA ATC CAG GAG TAC GGC GCC CCA TCG GAC CTC CTG CAG        4743
Asp Lys Gly Glu Ile Gln Glu Tyr Gly Ala Pro Ser Asp Leu Leu Gln
                1505                    1510                    1515

CAG AGA GGT CTT TTC TAC AGC ATG GCC AAA GAC GCC GGC TTG GTG             4788
Gln Arg Gly Leu Phe Tyr Ser Met Ala Lys Asp Ala Gly Leu Val
            1520                    1525                    1530
```

```
TGAGCCCCAG AGCTGGCATA TCTGGTCAGA ACTGCAGGGC CTATATGCCA GCGCCCCAGG      4848

GAGGAGTCAG TACCCCTGGT AAACCAAGCC TCCCACACTG AAACCAAAAC ATAAAAACCA      4908

AACCCAGACA ACCAAAACAT ATTCAAAGCA GCAGCCACCG CCATCCGGTC CCCTGCCTGG      4968

AACTGGCTGT GAAGACCCAG GAGAGACAGA GATGCGAACC ACC                        5011
```

( 2 ) INFORMATION FOR SEQ ID NO:2:

( i ) SEQUENCE CHARACTERISTICS:
        ( A ) LENGTH: 1531 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Leu Arg Gly Phe Cys Ser Ala Asp Gly Ser Asp Pro Leu Trp
 1               5                  10                  15

Asp Trp Asn Val Thr Trp Asn Thr Ser Asn Pro Asp Phe Thr Lys Cys
            20                  25                  30

Phe Gln Asn Thr Val Leu Val Trp Val Pro Cys Phe Tyr Leu Trp Ala
            35                  40                  45

Cys Phe Pro Phe Tyr Phe Leu Tyr Leu Ser Arg His Asp Arg Gly Tyr
     50                  55                  60

Ile Gln Met Thr Pro Leu Asn Lys Thr Lys Thr Ala Leu Gly Phe Leu
65                  70                  75                  80

Leu Trp Ile Val Cys Trp Ala Asp Leu Phe Tyr Ser Phe Trp Glu Arg
                85                  90                  95

Ser Arg Gly Ile Phe Leu Ala Pro Val Phe Leu Val Ser Pro Thr Leu
               100                 105                 110

Leu Gly Ile Thr Thr Leu Leu Ala Thr Phe Leu Ile Gln Leu Glu Arg
               115                 120                 125

Arg Lys Gly Val Gln Ser Ser Gly Ile Met Leu Thr Phe Trp Leu Val
       130                 135                 140

Ala Leu Val Cys Ala Leu Ala Ile Leu Arg Ser Lys Ile Met Thr Ala
145                 150                 155                 160

Leu Lys Glu Asp Ala Gln Val Asp Leu Phe Arg Asp Ile Thr Phe Tyr
                165                 170                 175

Val Tyr Phe Ser Leu Leu Leu Ile Gln Leu Val Leu Ser Cys Phe Ser
               180                 185                 190

Asp Arg Ser Pro Leu Phe Ser Glu Thr Ile His Asp Pro Asn Pro Cys
       195                 200                 205

Pro Glu Ser Ser Ala Ser Phe Leu Ser Arg Ile Thr Phe Trp Trp Ile
   210                 215                 220

Thr Gly Leu Ile Val Arg Gly Tyr Arg Gln Pro Leu Glu Gly Ser Asp
225                 230                 235                 240

Leu Trp Ser Leu Asn Lys Glu Asp Thr Ser Glu Gln Val Val Pro Val
                245                 250                 255

Leu Val Lys Asn Trp Lys Lys Glu Cys Ala Lys Thr Arg Lys Gln Pro
               260                 265                 270

Val Lys Val Val Tyr Ser Ser Lys Asp Pro Ala Gln Pro Lys Glu Ser
       275                 280                 285

Ser Lys Val Asp Ala Asn Glu Glu Val Glu Ala Leu Ile Val Lys Ser
       290                 295                 300

Pro Gln Lys Glu Trp Asn Pro Ser Leu Phe Lys Val Leu Tyr Lys Thr
305                 310                 315                 320
```

| | | | | | | | | | | | | | | |
|---|---|---|---|---|---|---|---|---|---|---|---|---|---|---|
| Phe | Gly | Pro | Tyr | Phe<br>325 | Leu | Met | Ser | Phe<br>330 | Phe | Lys | Ala | Ile | His<br>335 | Asp |
| Leu | Met | Met | Phe<br>340 | Ser | Gly | Pro | Gln | Ile<br>345 | Lys | Leu | Leu | Ile<br>350 | Lys | Phe |
| Val | Asn | Asp | Thr<br>355 | Lys | Ala | Pro | Asp<br>360 | Trp | Gln | Gly | Tyr | Phe<br>365 | Tyr | Thr | Val |
| Leu | Leu | Phe<br>370 | Val | Thr | Ala | Cys<br>375 | Leu | Gln | Thr | Leu | Val<br>380 | Leu | His | Gln | Tyr |
| Phe<br>385 | His | Ile | Cys | Phe | Val<br>390 | Ser | Gly | Met | Arg | Ile<br>395 | Lys | Thr | Ala | Val | Ile<br>400 |
| Gly | Ala | Val | Tyr | Arg<br>405 | Lys | Ala | Leu | Val | Ile<br>410 | Thr | Asn | Ser | Ala | Arg<br>415 | Lys |
| Ser | Ser | Thr | Val<br>420 | Gly | Glu | Ile | Val | Asn<br>425 | Leu | Met | Ser | Val | Asp<br>430 | Ala | Gln |
| Arg | Phe | Met<br>435 | Asp | Leu | Ala | Thr | Tyr<br>440 | Ile | Asn | Met | Ile | Trp<br>445 | Ser | Ala | Pro |
| Leu | Gln<br>450 | Val | Ile | Leu | Ala | Leu<br>455 | Tyr | Leu | Leu | Trp | Leu<br>460 | Asn | Leu | Gly | Pro |
| Ser<br>465 | Val | Leu | Ala | Gly | Val<br>470 | Ala | Val | Met | Val | Leu<br>475 | Met | Val | Pro | Val | Asn<br>480 |
| Ala | Val | Met | Ala | Met<br>485 | Lys | Thr | Lys | Thr | Tyr<br>490 | Gln | Val | Ala | His | Met<br>495 | Lys |
| Ser | Lys | Asp | Asn<br>500 | Arg | Ile | Lys | Leu | Met<br>505 | Asn | Glu | Ile | Leu | Asn<br>510 | Gly | Ile |
| Lys | Val | Leu<br>515 | Lys | Leu | Tyr | Ala | Trp<br>520 | Glu | Leu | Ala | Phe | Lys<br>525 | Asp | Lys | Val |
| Leu | Ala<br>530 | Ile | Arg | Gln | Glu | Glu<br>535 | Leu | Lys | Val | Leu | Lys<br>540 | Lys | Ser | Ala | Tyr |
| Leu<br>545 | Ser | Ala | Val | Gly | Thr<br>550 | Phe | Thr | Trp | Val | Cys<br>555 | Thr | Pro | Phe | Leu | Val<br>560 |
| Ala | Leu | Cys | Thr | Phe<br>565 | Ala | Val | Tyr | Val | Thr<br>570 | Ile | Asp | Glu | Asn | Asn<br>575 | Ile |
| Leu | Asp | Ala | Gln | Thr<br>580 | Ala | Phe | Val | Ser<br>585 | Leu | Ala | Leu | Phe | Asn<br>590 | Ile | Leu |
| Arg | Phe | Pro<br>595 | Leu | Asn | Ile | Leu | Pro<br>600 | Met | Val | Ile | Ser | Ser<br>605 | Ile | Val | Gln |
| Ala | Ser | Val<br>610 | Ser | Leu | Lys | Arg<br>615 | Leu | Arg | Ile | Phe | Leu<br>620 | Ser | His | Glu | Glu |
| Leu | Glu<br>625 | Pro | Asp | Ser | Ile<br>630 | Glu | Arg | Arg | Pro | Val<br>635 | Lys | Asp | Gly | Gly | Gly<br>640 |
| Thr | Asn | Ser | Ile | Thr<br>645 | Val | Arg | Asn | Ala | Thr<br>650 | Phe | Thr | Trp | Ala | Arg<br>655 | Ser |
| Asp | Pro | Pro | Thr<br>660 | Leu | Asn | Gly | Ile | Thr<br>665 | Phe | Ser | Ile | Pro | Glu<br>670 | Gly | Ala |
| Leu | Val | Ala<br>675 | Val | Val | Gly | Gln<br>680 | Val | Gly | Cys | Gly | Lys<br>685 | Leu | Ser | Leu | Leu |
| Ser | Ala<br>690 | Leu | Leu | Ala | Glu<br>695 | Met | Asp | Lys | Val | Glu<br>700 | Gly | His | Val | Ala | Ile |
| Lys<br>705 | Gly | Ser | Val | Ala | Tyr<br>710 | Val | Pro | Gln | Gln | Ala<br>715 | Trp | Ile | Gln | Asn | Asp<br>720 |
| Ser | Leu | Arg | Glu | Asn<br>725 | Ile | Leu | Phe | Gly | Cys<br>730 | Gln | Leu | Glu | Glu | Pro<br>735 | Tyr |
| Tyr | Arg | Ser | Val | Ile | Gln | Ala | Cys | Ala | Leu | Leu | Pro | Asp | Leu | Glu | Ile |

|       |       |       |       |       | 740   |       |       |       |       | 745   |       |       |       |       | 750   |       |       |
|-------|-------|-------|-------|-------|-------|-------|-------|-------|-------|-------|-------|-------|-------|-------|-------|-------|-------|
| Leu   | Pro   | Ser   | Gly   | Asp   | Arg   | Thr   | Glu   | Ile   | Gly   | Glu   | Lys   | Gly   | Val   | Asn   | Leu   |       |       |
|       |       | 755   |       |       |       |       | 760   |       |       |       |       | 765   |       |       |       |       |       |
| Ser   | Gly   | Gly   | Gln   | Lys   | Gln   | Arg   | Val   | Ser   | Leu   | Ala   | Arg   | Ala   | Val   | Tyr   | Ser   |       |       |
|       | 770   |       |       |       |       | 775   |       |       |       |       |       | 780   |       |       |       |       |       |
| Asn   | Ala   | Asp   | Ile   | Tyr   | Leu   | Phe   | Asp   | Asp   | Pro   | Leu   | Ser   | Ala   | Val   | Asp   | Ala   |       |       |
| 785   |       |       |       |       | 790   |       |       |       |       | 795   |       |       |       |       | 800   |       |       |
| His   | Val   | Gly   | Lys   | His   | Ile   | Phe   | Glu   | Asn   | Val   | Ile   | Gly   | Pro   | Lys   | Gly   | Met   |       |       |
|       |       |       |       | 805   |       |       |       |       | 810   |       |       |       |       | 815   |       |       |       |
| Leu   | Lys   | Asn   | Lys   | Thr   | Arg   | Ile   | Leu   | Val   | Thr   | His   | Ser   | Met   | Ser   | Tyr   | Leu   |       |       |
|       |       |       | 820   |       |       |       |       | 825   |       |       |       |       | 830   |       |       |       |       |
| Pro   | Gln   | Val   | Asp   | Val   | Ile   | Ile   | Val   | Met   | Ser   | Gly   | Gly   | Lys   | Ile   | Ser   | Glu   |       |       |
|       |       | 835   |       |       |       |       | 840   |       |       |       |       | 845   |       |       |       |       |       |
| Met   | Gly   | Ser   | Tyr   | Gln   | Glu   | Leu   | Leu   | Ala   | Arg   | Asp   | Gly   | Ala   | Phe   | Ala   | Glu   |       |       |
|       | 850   |       |       |       |       | 855   |       |       |       |       | 860   |       |       |       |       |       |       |
| Phe   | Leu   | Arg   | Thr   | Tyr   | Ala   | Ser   | Thr   | Glu   | Gln   | Glu   | Gln   | Asp   | Ala   | Glu   | Glu   |       |       |
| 865   |       |       |       |       | 870   |       |       |       |       | 875   |       |       |       |       | 880   |       |       |
| Asn   | Gly   | Val   | Thr   | Gly   | Val   | Ser   | Gly   | Pro   | Gly   | Lys   | Glu   | Ala   | Lys   | Gln   | Met   |       |       |
|       |       |       |       | 885   |       |       |       |       | 890   |       |       |       |       | 895   |       |       |       |
| Glu   | Asn   | Gly   | Met   | Leu   | Val   | Thr   | Asp   | Ser   | Ala   | Gly   | Lys   | Gln   | Leu   | Gln   | Arg   |       |       |
|       |       |       | 900   |       |       |       |       | 905   |       |       |       |       | 910   |       |       |       |       |
| Gln   | Leu   | Ser   | Ser   | Ser   | Ser   | Ser   | Tyr   | Ser   | Gly   | Asp   | Ile   | Ser   | Arg   | His   | His   |       |       |
|       |       | 915   |       |       |       |       | 920   |       |       |       |       | 925   |       |       |       |       |       |
| Asn   | Ser   | Thr   | Ala   | Glu   | Leu   | Gln   | Lys   | Ala   | Glu   | Ala   | Lys   | Lys   | Glu   | Glu   | Thr   |       |       |
|       |       | 930   |       |       |       |       | 935   |       |       |       |       | 940   |       |       |       |       |       |
| Trp   | Lys   | Leu   | Met   | Glu   | Ala   | Asp   | Lys   | Ala   | Gln   | Thr   | Gly   | Gln   | Val   | Lys   | Leu   |       |       |
| 945   |       |       |       |       | 950   |       |       |       |       | 955   |       |       |       |       | 960   |       |       |
| Ser   | Val   | Tyr   | Trp   | Asp   | Tyr   | Met   | Lys   | Ala   | Ile   | Gly   | Leu   | Phe   | Ile   | Ser   | Phe   |       |       |
|       |       |       |       | 965   |       |       |       |       | 970   |       |       |       |       | 975   |       |       |       |
| Leu   | Ser   | Ile   | Phe   | Leu   | Phe   | Met   | Cys   | Asn   | His   | Val   | Ser   | Ala   | Leu   | Ala   | Ser   |       |       |
|       |       |       | 980   |       |       |       |       | 985   |       |       |       |       | 990   |       |       |       |       |
| Asn   | Tyr   | Trp   | Leu   | Ser   | Leu   | Trp   | Thr   | Asp   | Asp   | Pro   | Ile   | Val   | Asn   | Gly   | Thr   |       |       |
|       |       | 995   |       |       |       |       | 1000  |       |       |       |       | 1005  |       |       |       |       |       |
| Gln   | Glu   | His   | Thr   | Lys   | Val   | Arg   | Leu   | Ser   | Val   | Tyr   | Gly   | Ala   | Leu   | Gly   | Ile   |       |       |
|       |       |       |       | 1010  |       |       |       |       | 1015  |       |       |       |       | 1020  |       |       |       |
| Ser   | Gln   | Gly   | Ile   | Ala   | Val   | Phe   | Gly   | Tyr   | Ser   | Met   | Ala   | Val   | Ser   | Ile   | Gly   |       |       |
| 1025  |       |       |       |       | 1030  |       |       |       |       | 1035  |       |       |       |       | 1040  |       |       |
| Gly   | Ile   | Leu   | Ala   | Ser   | Arg   | Cys   | Leu   | His   | Val   | Asp   | Leu   | Leu   | His   | Ser   | Ile   |       |       |
|       |       |       |       | 1045  |       |       |       |       | 1050  |       |       |       |       | 1055  |       |       |       |
| Leu   | Arg   | Ser   | Pro   | Met   | Ser   | Phe   | Phe   | Glu   | Arg   | Thr   | Pro   | Ser   | Gly   | Asn   | Leu   |       |       |
|       |       |       | 1060  |       |       |       |       | 1065  |       |       |       |       | 1070  |       |       |       |       |
| Val   | Asn   | Arg   | Phe   | Ser   | Lys   | Glu   | Leu   | Asp   | Thr   | Val   | Asp   | Ser   | Met   | Ile   | Pro   |       |       |
|       |       |       | 1075  |       |       |       |       | 1080  |       |       |       |       | 1085  |       |       |       |       |
| Glu   | Val   | Ile   | Lys   | Met   | Phe   | Met   | Gly   | Ser   | Leu   | Phe   | Asn   | Val   | Ile   | Gly   | Ala   |       |       |
|       |       | 1090  |       |       |       |       | 1095  |       |       |       |       | 1100  |       |       |       |       |       |
| Cys   | Ile   | Val   | Ile   | Leu   | Leu   | Ala   | Thr   | Pro   | Ile   | Ala   | Ala   | Ile   | Ile   | Ile   | Pro   |       |       |
| 1105  |       |       |       |       | 1110  |       |       |       |       | 1115  |       |       |       |       | 1120  |       |       |
| Pro   | Leu   | Gly   | Leu   | Ile   | Tyr   | Phe   | Phe   | Val   | Gln   | Arg   | Phe   | Tyr   | Val   | Ala   | Ser   |       |       |
|       |       |       |       | 1125  |       |       |       |       | 1130  |       |       |       |       | 1135  |       |       |       |
| Ser   | Arg   | Gln   | Leu   | Lys   | Arg   | Leu   | Glu   | Ser   | Val   | Ser   | Arg   | Ser   | Pro   | Val   | Tyr   |       |       |
|       |       |       | 1140  |       |       |       |       | 1145  |       |       |       |       | 1150  |       |       |       |       |
| Ser   | His   | Phe   | Asn   | Glu   | Thr   | Leu   | Leu   | Gly   | Val   | Ser   | Val   | Ile   | Arg   | Ala   | Phe   |       |       |
|       |       |       | 1155  |       |       |       |       | 1160  |       |       |       |       | 1165  |       |       |       |       |

Glu Glu Gln Glu Arg Phe Ile His Gln Ser Asp Leu Lys Val Asp Glu
1170                     1175                     1180

Asn Gln Lys Ala Tyr Tyr Pro Ser Ile Val Ala Asn Arg Trp Leu Ala
1185                     1190                     1195                     1200

Val Arg Leu Glu Cys Val Gly Asn Cys Ile Val Leu Phe Ala Ala Leu
                1205                     1210                     1215

Phe Ala Val Ile Ser Arg His Ser Leu Ser Ala Gly Leu Val Gly Leu
                1220                     1225                     1230

Ser Val Ser Tyr Ser Leu Gln Val Thr Thr Tyr Leu Asn Trp Leu Val
                1235                     1240                     1245

Arg Met Ser Ser Glu Met Glu Thr Asn Ile Val Ala Val Glu Arg Leu
                1250                     1255                     1260

Lys Glu Tyr Ser Glu Thr Glu Lys Glu Ala Pro Trp Gln Ile Gln Glu
1265                     1270                     1275                     1280

Thr Arg Pro Pro Ser Ser Trp Pro Gln Val Gly Arg Val Glu Phe Arg
                1285                     1290                     1295

Asn Tyr Cys Leu Arg Tyr Arg Glu Asp Leu Asp Phe Val Leu Arg His
                1300                     1305                     1310

Ile Asn Val Thr Ile Asn Gly Gly Glu Lys Val Gly Ile Val Gly Arg
                1315                     1320                     1325

Thr Gly Ala Gly Lys Ser Ser Leu Thr Leu Gly Leu Phe Arg Ile Asn
1330                     1335                     1340

Glu Ser Ala Glu Gly Glu Ile Ile Ile Asp Gly Ile Asn Ile Ala Lys
1345                     1350                     1355                     1360

Ile Gly Leu His Asp Leu Arg Phe Lys Ile Thr Ile Ile Pro Gln Asp
                1365                     1370                     1375

Pro Val Leu Phe Ser Gly Ser Leu Arg Met Asn Leu Asp Pro Phe Ser
                1380                     1385                     1390

Gln Tyr Ser Asp Glu Glu Val Trp Thr Ser Leu Glu Leu Ala His Leu
                1395                     1400                     1405

Lys Asp Phe Val Ser Ala Leu Pro Asp Lys Leu Asp His Glu Cys Ala
                1410                     1415                     1420

Glu Gly Gly Glu Asn Leu Ser Val Gly Gln Arg Gln Leu Val Cys Leu
1425                     1430                     1435                     1440

Ala Arg Ala Leu Leu Arg Lys Thr Lys Ile Leu Val Leu Asp Glu Ala
                1445                     1450                     1455

Thr Ala Ala Val Asp Leu Glu Thr Asp Asp Leu Ile Gln Ser Thr Ile
                1460                     1465                     1470

Arg Thr Gln Phe Glu Asp Cys Thr Val Leu Thr Ile Ala His Arg Leu
                1475                     1480                     1485

Asn Thr Ile Met Asp Tyr Thr Arg Val Ile Val Leu Asp Lys Gly Glu
                1490                     1495                     1500

Ile Gln Glu Tyr Gly Ala Pro Ser Asp Leu Leu Gln Gln Arg Gly Leu
1505                     1510                     1515                     1520

Phe Tyr Ser Met Ala Lys Asp Ala Gly Leu Val
                1525                     1530

( 2 ) INFORMATION FOR SEQ ID NO:3:

( i ) SEQUENCE CHARACTERISTICS:
        ( A ) LENGTH: 5011 base pairs
        ( B ) TYPE: nucleic acid
        ( C ) STRANDEDNESS: double
        ( D ) TOPOLOGY: linear ( i i ) MOLECULE TYPE: cDNA 5,882,875

-continued ( i x ) FEATURE:
  ( A ) NAME/KEY: CDS
  ( B ) LOCATION: 196..4788

( x i ) SEQUENCE DESCRIPTION: SEQ ID NO:3:

| | | |
|---|---|---|
| CAGGCGGCGT TGCGGCCCCG GCCCCGGCTC CCTGCGCCGC CGCCGCCGCC GCCGCCGCCG | 60 |
| CCGCCGCCGC CGCCGCCAGC GCTAGCGCCA GCAGCCGGGC CCGATCACCC GCCGCCCGGT | 120 |
| GCCGCCGCCG GCCCGCGCCA GCAACCGGGC CCGATCACCC GCCGCCCGGT GCCCGCCGCC | 180 |

```
GCCCGCGCCA CCGGC ATG GCG CTC CGG GGC TTC TGC AGC GCC GAT GGC TCC        231
               Met Ala Leu Arg Gly Phe Cys Ser Ala Asp Gly Ser
                1               5                     10

GAC CCG CTC TGG GAC TGG AAT GTC ACG TGG AAT ACC AGC AAC CCC GAC         279
Asp Pro Leu Trp Asp Trp Asn Val Thr Trp Asn Thr Ser Asn Pro Asp
            15                  20                  25

TTC ACC AAG TGC TTT CAG AAC ACG GTC CTC GTG TGG GTG CCT TGT TTT        327
Phe Thr Lys Cys Phe Gln Asn Thr Val Leu Val Trp Val Pro Cys Phe
        30                  35                  40

TAC CTC TGG GCC TGT TTC CCC TTC TAC TTC CTC TAT CTC TCC CGA CAT        375
Tyr Leu Trp Ala Cys Phe Pro Phe Tyr Phe Leu Tyr Leu Ser Arg His
 45                 50                  55                  60

GAC CGA GGC TAC ATT CAG ATG ACA CCT CTC AAC AAA ACC AAA ACT GCC        423
Asp Arg Gly Tyr Ile Gln Met Thr Pro Leu Asn Lys Thr Lys Thr Ala
            65                  70                  75

TTG GGA TTT TTG CTG TGG ATC GTC TGC TGG GCA GAC CTC TTC TAC TCT        471
Leu Gly Phe Leu Leu Trp Ile Val Cys Trp Ala Asp Leu Phe Tyr Ser
        80                  85                  90

TTC TGG GAA AGA AGT CGG GGC ATA TTC CTG GCC CCA GTG TTT CTG GTC        519
Phe Trp Glu Arg Ser Arg Gly Ile Phe Leu Ala Pro Val Phe Leu Val
            95                  100                 105

AGC CCA ACT CTC TTG GGC ATC ACC ACG CTG CTT GCT ACC TTT TTA ATT        567
Ser Pro Thr Leu Leu Gly Ile Thr Thr Leu Leu Ala Thr Phe Leu Ile
110                 115                 120

CAG CTG GAG AGG AGG AAG GGA GTT CAG TCT TCA GGG ATC ATG CTC ACT        615
Gln Leu Glu Arg Arg Lys Gly Val Gln Ser Ser Gly Ile Met Leu Thr
125                 130                 135                 140

TTC TGG CTG GTA GCC CTA GTG TGT GCC CTA GCC ATC CTG AGA TCC AAA        663
Phe Trp Leu Val Ala Leu Val Cys Ala Leu Ala Ile Leu Arg Ser Lys
            145                 150                 155

ATT ATG ACA GCC TTA AAA GAG GAT GCC CAG GTG GAC CTG TTT CGT GAC        711
Ile Met Thr Ala Leu Lys Glu Asp Ala Gln Val Asp Leu Phe Arg Asp
            160                 165                 170

ATC ACT TTC TAC GTC TAC TTT TCC CTC TTA CTC ATT CAG CTC GTC TTG        759
Ile Thr Phe Tyr Val Tyr Phe Ser Leu Leu Leu Ile Gln Leu Val Leu
            175                 180                 185

TCC TGT TTC TCA GAT CGC TCA CCC CTG TTC TCG GAA ACC ATC CAC GAC        807
Ser Cys Phe Ser Asp Arg Ser Pro Leu Phe Ser Glu Thr Ile His Asp
        190                 195                 200

CCT AAT CCC TGC CCA GAG TCC AGC GCT TCC TTC CTG TCG AGG ATC ACC        855
Pro Asn Pro Cys Pro Glu Ser Ser Ala Ser Phe Leu Ser Arg Ile Thr
205                 210                 215                 220

TTC TGG TGG ATC ACA GGG TTG ATT GTC CGG GGC TAC CGC CAG CCC CTG        903
Phe Trp Trp Ile Thr Gly Leu Ile Val Arg Gly Tyr Arg Gln Pro Leu
            225                 230                 235

GAG GGC AGT GAC CTC TGG TCC TTA AAC AAG GAG GAC ACG TCG GAA CAA        951
Glu Gly Ser Asp Leu Trp Ser Leu Asn Lys Glu Asp Thr Ser Glu Gln
            240                 245                 250

GTC GTG CCT GTT TTG GTA AAG AAC TGG AAG AAG GAA TGC GCC AAG ACT        999
Val Val Pro Val Leu Val Lys Asn Trp Lys Lys Glu Cys Ala Lys Thr
        255                 260                 265
```

| | | | | | | | | | | | | | | | |
|---|---|---|---|---|---|---|---|---|---|---|---|---|---|---|---|
| AGG | AAG | CAG | CCG | GTG | AAG | GTT | GTG | TAC | TCC | TCC | AAG | GAT | CCT | GCC | CAG | 1047 |
| Arg | Lys | Gln | Pro | Val | Lys | Val | Val | Tyr | Ser | Ser | Lys | Asp | Pro | Ala | Gln | |
| | 270 | | | | 275 | | | | | 280 | | | | | | |
| CCG | AAA | GAG | AGT | TCC | AAG | GTG | GAT | GCG | AAT | GAG | GAG | GTG | GAG | GCT | TTG | 1095 |
| Pro | Lys | Glu | Ser | Ser | Lys | Val | Asp | Ala | Asn | Glu | Glu | Val | Glu | Ala | Leu | |
| 285 | | | | | 290 | | | | | 295 | | | | | 300 | |
| ATC | GTC | AAG | TCC | CCA | CAG | AAG | GAG | TGG | AAC | CCC | TCT | CTG | TTT | AAG | GTG | 1143 |
| Ile | Val | Lys | Ser | Pro | Gln | Lys | Glu | Trp | Asn | Pro | Ser | Leu | Phe | Lys | Val | |
| | | | | 305 | | | | | 310 | | | | | 315 | | |
| TTA | TAC | AAG | ACC | TTT | GGG | CCC | TAC | TTC | CTC | ATG | AGC | TTC | TTC | TTC | AAG | 1191 |
| Leu | Tyr | Lys | Thr | Phe | Gly | Pro | Tyr | Phe | Leu | Met | Ser | Phe | Phe | Phe | Lys | |
| | | | 320 | | | | | 325 | | | | | 330 | | | |
| GCC | ATC | CAC | GAC | CTG | ATG | ATG | TTT | TCC | GGG | CCG | CAG | ATC | TTA | AAG | TTG | 1239 |
| Ala | Ile | His | Asp | Leu | Met | Met | Phe | Ser | Gly | Pro | Gln | Ile | Leu | Lys | Leu | |
| | | 335 | | | | | 340 | | | | | 345 | | | | |
| CTC | ATC | AAG | TTC | GTG | AAT | GAC | ACG | AAG | GCC | CCA | GAC | TGG | CAG | GGC | TAC | 1287 |
| Leu | Ile | Lys | Phe | Val | Asn | Asp | Thr | Lys | Ala | Pro | Asp | Trp | Gln | Gly | Tyr | |
| | 350 | | | | | 355 | | | | | 360 | | | | | |
| TTC | TAC | ACC | GTG | CTG | CTG | TTT | GTC | ACT | GCC | TGC | CTG | CAG | ACC | CTC | GTG | 1335 |
| Phe | Tyr | Thr | Val | Leu | Leu | Phe | Val | Thr | Ala | Cys | Leu | Gln | Thr | Leu | Val | |
| 365 | | | | | 370 | | | | | 375 | | | | | 380 | |
| CTG | CAC | CAG | TAC | TTC | CAC | ATC | TGC | TTC | GTC | AGT | GGC | ATG | AGG | ATC | AAG | 1383 |
| Leu | His | Gln | Tyr | Phe | His | Ile | Cys | Phe | Val | Ser | Gly | Met | Arg | Ile | Lys | |
| | | | | 385 | | | | | 390 | | | | | 395 | | |
| ACC | GCT | GTC | ATT | GGG | GCT | GTC | TAT | CGG | AAG | GCC | CTG | GTG | ATC | ACC | AAT | 1431 |
| Thr | Ala | Val | Ile | Gly | Ala | Val | Tyr | Arg | Lys | Ala | Leu | Val | Ile | Thr | Asn | |
| | | | 400 | | | | | 405 | | | | | 410 | | | |
| TCA | GCC | AGA | AAA | TCC | TCC | ACG | GTC | GGG | GAG | ATT | GTC | AAC | CTC | ATG | TCT | 1479 |
| Ser | Ala | Arg | Lys | Ser | Ser | Thr | Val | Gly | Glu | Ile | Val | Asn | Leu | Met | Ser | |
| | | 415 | | | | | 420 | | | | | 425 | | | | |
| GTG | GAC | GCT | CAG | AGG | TTC | ATG | GAC | TTG | GCC | ACG | TAC | ATT | AAC | ATG | ATC | 1527 |
| Val | Asp | Ala | Gln | Arg | Phe | Met | Asp | Leu | Ala | Thr | Tyr | Ile | Asn | Met | Ile | |
| | 430 | | | | | 435 | | | | | 440 | | | | | |
| TGG | TCA | GCC | CCC | CTG | CAA | GTC | ATC | CTT | GCT | CTC | TAC | CTC | CTG | TGG | CTG | 1575 |
| Trp | Ser | Ala | Pro | Leu | Gln | Val | Ile | Leu | Ala | Leu | Tyr | Leu | Leu | Trp | Leu | |
| 445 | | | | | 450 | | | | | 455 | | | | | 460 | |
| AAT | CTG | GGC | CCT | TCC | GTC | CTG | GCT | GGA | GTG | GCG | GTG | ATG | GTC | CTC | ATG | 1623 |
| Asn | Leu | Gly | Pro | Ser | Val | Leu | Ala | Gly | Val | Ala | Val | Met | Val | Leu | Met | |
| | | | | 465 | | | | | 470 | | | | | 475 | | |
| GTG | CCC | GTC | AAT | GCT | GTG | ATG | GCG | ATG | AAG | ACC | AAG | ACG | TAT | CAG | GTG | 1671 |
| Val | Pro | Val | Asn | Ala | Val | Met | Ala | Met | Lys | Thr | Lys | Thr | Tyr | Gln | Val | |
| | | | 480 | | | | | 485 | | | | | 490 | | | |
| GCC | CAC | ATG | AAG | AGC | AAA | GAC | AAT | CGG | ATC | AAG | CTG | ATG | AAC | GAA | ATT | 1719 |
| Ala | His | Met | Lys | Ser | Lys | Asp | Asn | Arg | Ile | Lys | Leu | Met | Asn | Glu | Ile | |
| | | 495 | | | | | 500 | | | | | 505 | | | | |
| CTC | AAT | GGG | ATC | AAA | GTG | CTA | AAG | CTT | TAT | GCC | TGG | GAG | CTG | GCA | TTC | 1767 |
| Leu | Asn | Gly | Ile | Lys | Val | Leu | Lys | Leu | Tyr | Ala | Trp | Glu | Leu | Ala | Phe | |
| | 510 | | | | | 515 | | | | | 520 | | | | | |
| AAG | GAC | AAG | GTG | CTG | GCC | ATC | AGG | CAG | GAG | GAG | CTG | AAG | GTG | CTG | AAG | 1815 |
| Lys | Asp | Lys | Val | Leu | Ala | Ile | Arg | Gln | Glu | Glu | Leu | Lys | Val | Leu | Lys | |
| 525 | | | | | 530 | | | | | 535 | | | | | 540 | |
| AAG | TCT | GCC | TAC | CTG | TCA | GCC | GTG | GGC | ACC | TTC | ACC | TGG | GTC | TGC | ACG | 1863 |
| Lys | Ser | Ala | Tyr | Leu | Ser | Ala | Val | Gly | Thr | Phe | Thr | Trp | Val | Cys | Thr | |
| | | | | 545 | | | | | 550 | | | | | 555 | | |
| CCC | TTT | CTG | GTG | GCC | TTG | TGC | ACA | TTT | GCC | GTC | TAC | GTG | ACC | ATT | GAC | 1911 |
| Pro | Phe | Leu | Val | Ala | Leu | Cys | Thr | Phe | Ala | Val | Tyr | Val | Thr | Ile | Asp | |
| | | | | 560 | | | | | 565 | | | | | 570 | | |
| GAG | AAC | AAC | ATC | CTG | GAT | GCC | CAG | ACA | GCC | TTC | GTG | TCT | TTG | GCC | TTG | 1959 |
| Glu | Asn | Asn | Ile | Leu | Asp | Ala | Gln | Thr | Ala | Phe | Val | Ser | Leu | Ala | Leu | |
| | | 575 | | | | | 580 | | | | | 585 | | | | |

| | | | | | | | | | | | | | | | | |
|---|---|---|---|---|---|---|---|---|---|---|---|---|---|---|---|---|
| TTC | AAC | ATC | CTC | CGG | TTT | CCC | CTG | AAC | ATT | CTC | CCC | ATG | GTC | ATC | AGC | 2007 |
| Phe | Asn | Ile | Leu | Arg | Phe | Pro | Leu | Asn | Ile | Leu | Pro | Met | Val | Ile | Ser | |
| | 590 | | | | 595 | | | | | 600 | | | | | | |
| AGC | ATC | GTG | CAG | GCG | AGT | GTC | TCC | CTC | AAA | CGC | CTG | AGG | ATC | TTT | CTC | 2055 |
| Ser | Ile | Val | Gln | Ala | Ser | Val | Ser | Leu | Lys | Arg | Leu | Arg | Ile | Phe | Leu | |
| 605 | | | | | 610 | | | | | 615 | | | | | 620 | |
| TCC | CAT | GAG | GAG | CTG | GAA | CCT | GAC | AGC | ATC | GAG | CGA | CGG | CCT | GTC | AAA | 2103 |
| Ser | His | Glu | Glu | Leu | Glu | Pro | Asp | Ser | Ile | Glu | Arg | Arg | Pro | Val | Lys | |
| | | | | 625 | | | | | 630 | | | | | 635 | | |
| GAC | GGC | GGG | GGC | ACG | AAC | AGC | ATC | ACC | GTG | AGG | AAT | GCC | ACA | TTC | ACC | 2151 |
| Asp | Gly | Gly | Gly | Thr | Asn | Ser | Ile | Thr | Val | Arg | Asn | Ala | Thr | Phe | Thr | |
| | | | 640 | | | | | 645 | | | | | 650 | | | |
| TGG | GCC | AGG | AGC | GAC | CCT | CCC | ACA | CTG | AAT | GGC | ATC | ACC | TTC | TCC | ATC | 2199 |
| Trp | Ala | Arg | Ser | Asp | Pro | Pro | Thr | Leu | Asn | Gly | Ile | Thr | Phe | Ser | Ile | |
| | | 655 | | | | | 660 | | | | | 665 | | | | |
| CCC | GAA | GGT | GCT | TTG | GTG | GCC | GTG | GTG | GGC | CAG | GTG | GGC | TGC | GGA | AAG | 2247 |
| Pro | Glu | Gly | Ala | Leu | Val | Ala | Val | Val | Gly | Gln | Val | Gly | Cys | Gly | Lys | |
| | 670 | | | | | 675 | | | | | 680 | | | | | |
| TCG | TCC | CTG | CTC | TCA | GCC | CTC | TTG | GCT | GAG | ATG | GAC | AAA | GTG | GAG | GGG | 2295 |
| Ser | Ser | Leu | Leu | Ser | Ala | Leu | Leu | Ala | Glu | Met | Asp | Lys | Val | Glu | Gly | |
| 685 | | | | | 690 | | | | | 695 | | | | | 700 | |
| CAC | GTG | GCT | ATC | AAG | GGC | TCC | GTG | GCC | TAT | GTG | CCA | CAG | CAG | GCC | TGG | 2343 |
| His | Val | Ala | Ile | Lys | Gly | Ser | Val | Ala | Tyr | Val | Pro | Gln | Gln | Ala | Trp | |
| | | | | 705 | | | | | 710 | | | | | 715 | | |
| ATT | CAG | AAT | GAT | TCT | CTC | CGA | GAA | AAC | ATC | CTT | TTT | GGA | TGT | CAG | CTG | 2391 |
| Ile | Gln | Asn | Asp | Ser | Leu | Arg | Glu | Asn | Ile | Leu | Phe | Gly | Cys | Gln | Leu | |
| | | | 720 | | | | | 725 | | | | | 730 | | | |
| GAG | GAA | CCA | TAT | TAC | AGG | TCC | GTG | ATA | CAG | GCC | TGT | GCC | CTC | CTC | CCA | 2439 |
| Glu | Glu | Pro | Tyr | Tyr | Arg | Ser | Val | Ile | Gln | Ala | Cys | Ala | Leu | Leu | Pro | |
| | | 735 | | | | | 740 | | | | | 745 | | | | |
| GAC | CTG | GAA | ATC | CTG | CCC | AGT | GGG | GAT | CGG | ACA | GAG | ATT | GGC | GAG | AAG | 2487 |
| Asp | Leu | Glu | Ile | Leu | Pro | Ser | Gly | Asp | Arg | Thr | Glu | Ile | Gly | Glu | Lys | |
| | 750 | | | | | 755 | | | | | 760 | | | | | |
| GGC | GTG | AAC | CTG | TCT | GGG | GGA | CAG | AAG | CAG | CGC | GTG | AGC | CTG | GCC | CGG | 2535 |
| Gly | Val | Asn | Leu | Ser | Gly | Gly | Gln | Lys | Gln | Arg | Val | Ser | Leu | Ala | Arg | |
| 765 | | | | | 770 | | | | | 775 | | | | | 780 | |
| GCC | GTG | TAC | TCC | AAC | GCT | GAC | ATT | TAC | CTC | TTC | GAT | GAT | CCC | CTC | TCA | 2583 |
| Ala | Val | Tyr | Ser | Asn | Ala | Asp | Ile | Tyr | Leu | Phe | Asp | Asp | Pro | Leu | Ser | |
| | | | | 785 | | | | | 790 | | | | | 795 | | |
| GCA | GTG | GAT | GCC | CAT | GTG | GGA | AAA | CAC | ATC | TTT | GAA | AAT | GTG | ATT | GGC | 2631 |
| Ala | Val | Asp | Ala | His | Val | Gly | Lys | His | Ile | Phe | Glu | Asn | Val | Ile | Gly | |
| | | | 800 | | | | | 805 | | | | | 810 | | | |
| CCC | AAG | GGG | ATG | CTG | AAG | AAC | AAG | ACG | CGG | ATC | TTG | GTC | ACG | CAC | AGC | 2679 |
| Pro | Lys | Gly | Met | Leu | Lys | Asn | Lys | Thr | Arg | Ile | Leu | Val | Thr | His | Ser | |
| | | 815 | | | | | 820 | | | | | 825 | | | | |
| ATG | AGC | TAC | TTG | CCG | CAG | GTG | GAC | GTC | ATC | ATC | GTC | ATG | AGT | GGC | GGC | 2727 |
| Met | Ser | Tyr | Leu | Pro | Gln | Val | Asp | Val | Ile | Ile | Val | Met | Ser | Gly | Gly | |
| | 830 | | | | | 835 | | | | | 840 | | | | | |
| AAG | ATC | TCT | GAG | ATG | GGC | TCC | TAC | CAG | GAG | CTG | CTG | GCT | CGA | GAC | GGC | 2775 |
| Lys | Ile | Ser | Glu | Met | Gly | Ser | Tyr | Gln | Glu | Leu | Leu | Ala | Arg | Asp | Gly | |
| 845 | | | | | 850 | | | | | 855 | | | | | 860 | |
| GCC | TTC | GCT | GAG | TTC | CTG | CGT | ACC | TAT | GCC | AGC | ACA | GAG | CAG | GAG | CAG | 2823 |
| Ala | Phe | Ala | Glu | Phe | Leu | Arg | Thr | Tyr | Ala | Ser | Thr | Glu | Gln | Glu | Gln | |
| | | | | 865 | | | | | 870 | | | | | 875 | | |
| GAT | GCA | GAG | GAG | AAC | GGG | GTC | ACG | GGC | GTC | AGC | GGT | CCA | GGG | AAG | GAA | 2871 |
| Asp | Ala | Glu | Glu | Asn | Gly | Val | Thr | Gly | Val | Ser | Gly | Pro | Gly | Lys | Glu | |
| | | | 880 | | | | | 885 | | | | | 890 | | | |
| GCA | AAG | CAA | ATG | GAG | AAT | GGC | ATG | CTG | GTG | ACG | GAC | AGT | GCA | GGG | AAG | 2919 |
| Ala | Lys | Gln | Met | Glu | Asn | Gly | Met | Leu | Val | Thr | Asp | Ser | Ala | Gly | Lys | |
| | | 895 | | | | | 900 | | | | | 905 | | | | |

| | | | | | | | | | | | | | | | | |
|---|---|---|---|---|---|---|---|---|---|---|---|---|---|---|---|---|
| CAA | CTG | CAG | AGA | CAG | CTC | AGC | AGC | TCC | TCC | TCC | TAT | AGT | GGG | GAC | ATC | 2967 |
| Gln | Leu | Gln | Arg | Gln | Leu | Ser | Ser | Ser | Ser | Ser | Tyr | Ser | Gly | Asp | Ile | |
| | 910 | | | | 915 | | | | | 920 | | | | | | |
| AGC | AGG | CAC | CAC | AAC | AGC | ACC | GCA | GAA | CTG | CAG | AAA | GCT | GAG | GCC | AAG | 3015 |
| Ser | Arg | His | His | Asn | Ser | Thr | Ala | Glu | Leu | Gln | Lys | Ala | Glu | Ala | Lys | |
| 925 | | | | | 930 | | | | | 935 | | | | | 940 | |
| AAG | GAG | GAG | ACC | TGG | AAG | CTG | ATG | GAG | GCT | GAC | AAG | GCG | CAG | ACA | GGG | 3063 |
| Lys | Glu | Glu | Thr | Trp | Lys | Leu | Met | Glu | Ala | Asp | Lys | Ala | Gln | Thr | Gly | |
| | | | | 945 | | | | | 950 | | | | | 955 | | |
| CAG | GTC | AAG | CTT | TCC | GTG | TAC | TGG | GAC | TAC | ATG | AAG | GCC | ATC | GGA | CTC | 3111 |
| Gln | Val | Lys | Leu | Ser | Val | Tyr | Trp | Asp | Tyr | Met | Lys | Ala | Ile | Gly | Leu | |
| | | | 960 | | | | | 965 | | | | | 970 | | | |
| TTC | ATC | TCC | TTC | CTC | AGC | ATC | TTC | CTT | TTC | ATG | TGT | AAC | CAT | GTG | TCC | 3159 |
| Phe | Ile | Ser | Phe | Leu | Ser | Ile | Phe | Leu | Phe | Met | Cys | Asn | His | Val | Ser | |
| | | 975 | | | | | 980 | | | | | 985 | | | | |
| GCG | CTG | GCT | TCC | AAC | TAT | TGG | CTC | AGC | CTC | TGG | ACT | GAT | GAC | CCC | ATC | 3207 |
| Ala | Leu | Ala | Ser | Asn | Tyr | Trp | Leu | Ser | Leu | Trp | Thr | Asp | Asp | Pro | Ile | |
| | 990 | | | | | 995 | | | | | 1000 | | | | | |
| GTC | AAC | GGG | ACT | CAG | GAG | CAC | ACG | AAA | GTC | CGG | CTG | AGC | GTC | TAT | GGA | 3255 |
| Val | Asn | Gly | Thr | Gln | Glu | His | Thr | Lys | Val | Arg | Leu | Ser | Val | Tyr | Gly | |
| 1005 | | | | | 1010 | | | | | 1015 | | | | | 1020 | |
| GCC | CTG | GGC | ATT | TCA | CAA | GGG | ATC | GCC | GTG | TTT | GGC | TAC | TCC | ATG | GCC | 3303 |
| Ala | Leu | Gly | Ile | Ser | Gln | Gly | Ile | Ala | Val | Phe | Gly | Tyr | Ser | Met | Ala | |
| | | | | 1025 | | | | | 1030 | | | | | 1035 | | |
| GTG | TCC | ATC | GGG | GGG | ATC | TTG | GCT | TCC | CGC | TGT | CTG | CAC | GTG | GAC | CTG | 3351 |
| Val | Ser | Ile | Gly | Gly | Ile | Leu | Ala | Ser | Arg | Cys | Leu | His | Val | Asp | Leu | |
| | | | 1040 | | | | | 1045 | | | | | 1050 | | | |
| CTG | CAC | AGC | ATC | CTG | CGG | TCA | CCC | ATG | AGC | TTC | TTT | GAG | CGG | ACC | CCC | 3399 |
| Leu | His | Ser | Ile | Leu | Arg | Ser | Pro | Met | Ser | Phe | Phe | Glu | Arg | Thr | Pro | |
| | | 1055 | | | | | 1060 | | | | | 1065 | | | | |
| AGT | GGG | AAC | CTG | GTG | AAC | CGC | TTC | TCC | AAG | GAG | CTG | GAC | ACA | GTG | GAC | 3447 |
| Ser | Gly | Asn | Leu | Val | Asn | Arg | Phe | Ser | Lys | Glu | Leu | Asp | Thr | Val | Asp | |
| 1070 | | | | | 1075 | | | | | 1080 | | | | | | |
| TCC | ATG | ATC | CCG | GAG | GTC | ATC | AAG | ATG | TTC | ATG | GGC | TCC | CTG | TTC | AAC | 3495 |
| Ser | Met | Ile | Pro | Glu | Val | Ile | Lys | Met | Phe | Met | Gly | Ser | Leu | Phe | Asn | |
| 1085 | | | | | 1090 | | | | | 1095 | | | | | 1100 | |
| GTC | ATT | GGT | GCC | TGC | ATC | GTT | ATC | CTG | CTG | GCC | ACG | CCC | ATC | GCC | GCC | 3543 |
| Val | Ile | Gly | Ala | Cys | Ile | Val | Ile | Leu | Leu | Ala | Thr | Pro | Ile | Ala | Ala | |
| | | | | 1105 | | | | | 1110 | | | | | 1115 | | |
| ATC | ATC | ATC | CCG | CCC | CTT | GGC | CTC | ATC | TAC | TTC | TTC | GTC | CAG | AGG | TTC | 3591 |
| Ile | Ile | Ile | Pro | Pro | Leu | Gly | Leu | Ile | Tyr | Phe | Phe | Val | Gln | Arg | Phe | |
| | | | 1120 | | | | | 1125 | | | | | 1130 | | | |
| TAC | GTG | GCT | TCC | TCC | CGG | CAG | CTG | AAG | CGC | CTC | GAG | TCG | GTC | AGC | CGC | 3639 |
| Tyr | Val | Ala | Ser | Ser | Arg | Gln | Leu | Lys | Arg | Leu | Glu | Ser | Val | Ser | Arg | |
| | | | 1135 | | | | | 1140 | | | | | 1145 | | | |
| TCC | CCG | GTC | TAT | TCC | CAT | TTC | AAC | GAG | ACC | TTG | CTG | GGG | GTC | AGC | GTC | 3687 |
| Ser | Pro | Val | Tyr | Ser | His | Phe | Asn | Glu | Thr | Leu | Leu | Gly | Val | Ser | Val | |
| | 1150 | | | | | 1155 | | | | | 1160 | | | | | |
| ATT | CGA | GCC | TTC | GAG | GAG | CAG | GAG | CGC | TTC | ATC | CAC | CAG | AGT | GAC | CTG | 3735 |
| Ile | Arg | Ala | Phe | Glu | Glu | Gln | Glu | Arg | Phe | Ile | His | Gln | Ser | Asp | Leu | |
| 1165 | | | | | 1170 | | | | | 1175 | | | | | 1180 | |
| AAG | GTG | GAC | GAG | AAC | CAG | AAG | GCC | TAT | TAC | CCC | AGC | ATC | GTG | GCC | AAC | 3783 |
| Lys | Val | Asp | Glu | Asn | Gln | Lys | Ala | Tyr | Tyr | Pro | Ser | Ile | Val | Ala | Asn | |
| | | | | 1185 | | | | | 1190 | | | | | 1195 | | |
| AGG | TGG | CTG | GCC | GTG | CGG | CTG | GAG | TGT | GTG | GGC | AAC | TGC | ATC | GTT | CTG | 3831 |
| Arg | Trp | Leu | Ala | Val | Arg | Leu | Glu | Cys | Val | Gly | Asn | Cys | Ile | Val | Leu | |
| | | | | 1200 | | | | | 1205 | | | | | 1210 | | |
| TTT | GCT | GCC | CTG | TTT | GCG | GTG | ATC | TCC | AGG | CAC | AGC | CTC | AGT | GCT | GGC | 3879 |
| Phe | Ala | Ala | Leu | Phe | Ala | Val | Ile | Ser | Arg | His | Ser | Leu | Ser | Ala | Gly | |
| | | | 1215 | | | | | 1220 | | | | | 1225 | | | |

```
TTG GTG GGC CTC TCA GTG TCT TAC TCA TTG CAG GTC ACC ACG TAC TTG         3927
Leu Val Gly Leu Ser Val Ser Tyr Ser Leu Gln Val Thr Thr Tyr Leu
            1230            1235            1240

AAC TGG CTG GTT CGG ATG TCA TCT GAA ATG GAA ACC AAC ATC GTG GCC         3975
Asn Trp Leu Val Arg Met Ser Ser Glu Met Glu Thr Asn Ile Val Ala
1245            1250            1255                        1260

GTG GAG AGG CTC AAG GAG TAT TCA GAG ACT GAG AAG GAG GCG CCC TGG         4023
Val Glu Arg Leu Lys Glu Tyr Ser Glu Thr Glu Lys Glu Ala Pro Trp
                    1265            1270                    1275

CAA ATC CAG GAG ACA GCT CCG CCC AGC AGC TGG CCC CAG GTG GGC CGA         4071
Gln Ile Gln Glu Thr Ala Pro Pro Ser Ser Trp Pro Gln Val Gly Arg
                1280            1285                1290

GTG GAA TTC CGG AAC TAC TGC CTG CGC TAC CGA GAG GAC CTG GAC TTC         4119
Val Glu Phe Arg Asn Tyr Cys Leu Arg Tyr Arg Glu Asp Leu Asp Phe
            1295            1300            1305

GTT CTC AGG CAC ATC AAT GTC ACG ATC AAT GGG GGA GAA AAG GTC GGC         4167
Val Leu Arg His Ile Asn Val Thr Ile Asn Gly Gly Glu Lys Val Gly
1310            1315            1320

ATC GTG GGG CGG ACG GGA GCT GGG AAG TCG TCC CTG ACC CTG GGC TTA         4215
Ile Val Gly Arg Thr Gly Ala Gly Lys Ser Ser Leu Thr Leu Gly Leu
1325            1330            1335            1340

TTT CGG ATC AAC GAG TCT GCC GAA GGA GAG ATC ATC ATC GAT GGC ATC         4263
Phe Arg Ile Asn Glu Ser Ala Glu Gly Glu Ile Ile Ile Asp Gly Ile
                1345            1350            1355

AAC ATC GCC AAG ATC GGC CTG CAC GAC CTC CGC TTC AAG ATC ACC ATC         4311
Asn Ile Ala Lys Ile Gly Leu His Asp Leu Arg Phe Lys Ile Thr Ile
                1360            1365            1370

ATC CCC CAG GAC CCT GTT TTG TTT TCG GGT TCC CTC CGA ATG AAC CTG         4359
Ile Pro Gln Asp Pro Val Leu Phe Ser Gly Ser Leu Arg Met Asn Leu
            1375            1380            1385

GAC CCA TTC AGC CAG TAC TCG GAT GAA GAA GTC TGG ACG TCC CTG GAG         4407
Asp Pro Phe Ser Gln Tyr Ser Asp Glu Glu Val Trp Thr Ser Leu Glu
            1390            1395            1400

CTG GCC CAC CTG AAG GAC TTC GTG TCA GCC CTT CCT GAC AAG CTA GAC         4455
Leu Ala His Leu Lys Asp Phe Val Ser Ala Leu Pro Asp Lys Leu Asp
1405            1410            1415            1420

CAT GAA TGT GCA GAA GGC GGG GAG AAC CTC AGT GTC GGG CAG CGC CAG         4503
His Glu Cys Ala Glu Gly Gly Glu Asn Leu Ser Val Gly Gln Arg Gln
                1425            1430            1435

CTT GTG TGC CTA GCC CGG GCC CTG CTG AGG AAG ACG AAG ATC CTT GTG         4551
Leu Val Cys Leu Ala Arg Ala Leu Leu Arg Lys Thr Lys Ile Leu Val
            1440            1445            1450

TTG GAT GAG GCC ACG GCA GCC GTG GAC CTG GAA ACG GAC GAC CTC ATC         4599
Leu Asp Glu Ala Thr Ala Ala Val Asp Leu Glu Thr Asp Asp Leu Ile
            1455            1460            1465

CAG TCC ACC ATC CGG ACA CAG TTC GAG GAC TGC ACC GTC CTC ACC ATC         4647
Gln Ser Thr Ile Arg Thr Gln Phe Glu Asp Cys Thr Val Leu Thr Ile
            1470            1475            1480

GCC CAC CGG CTC AAC ACC ATC ATG GAC TAC ACA AGG GTG ATC GTC TTG         4695
Ala His Arg Leu Asn Thr Ile Met Asp Tyr Thr Arg Val Ile Val Leu
1485            1490            1495            1500

GAC AAA GGA GAA ATC CAG GAG TAC GGC GCC CCA TCG GAC CTC CTG CAG         4743
Asp Lys Gly Glu Ile Gln Glu Tyr Gly Ala Pro Ser Asp Leu Leu Gln
                1505            1510            1515

CAG AGA GGT CTT TTC TAC AGC ATG GCC AAA GAC GCC GGC TTG GTG               4788
Gln Arg Gly Leu Phe Tyr Ser Met Ala Lys Asp Ala Gly Leu Val
            1520            1525            1530

TGAGCCCCAG AGCTGGCATA TCTGGTCAGA ACTGCAGGGC CTATATGCCA GCGCCCCAGG      4848

GAGGAGTCAG TACCCCTGGT AAACCAAGCC TCCCACACTG AAACCAAAAC ATAAAAACCA      4908
```

```
AACCCAGACA  ACCAAAACAT  ATTCAAAGCA  GCAGCCACCG  CCATCCGGTC  CCCTGCCTGG    4968

AACTGGCTGT  GAAGACCCAG  GAGAGACAGA  GATGCGAACC  ACC                      5011
```

(2) INFORMATION FOR SEQ ID NO:4:

(i) SEQUENCE CHARACTERISTICS:
        (A) LENGTH: 1531 amino acids
        (B) TYPE: amino acid
        (D) TOPOLOGY: linear (ii) MOLECULE TYPE: protein (xi) SEQUENCE DESCRIPTION: SEQ ID NO:4:

```
Met  Ala  Leu  Arg  Gly  Phe  Cys  Ser  Ala  Asp  Gly  Ser  Asp  Pro  Leu  Trp
 1              5                        10                       15

Asp  Trp  Asn  Val  Thr  Trp  Asn  Thr  Ser  Asn  Pro  Asp  Phe  Thr  Lys  Cys
               20                       25                  30

Phe  Gln  Asn  Thr  Val  Leu  Val  Trp  Val  Pro  Cys  Phe  Tyr  Leu  Trp  Ala
          35                       40                  45

Cys  Phe  Pro  Phe  Tyr  Phe  Leu  Tyr  Leu  Ser  Arg  His  Asp  Arg  Gly  Tyr
     50                       55                  60

Ile  Gln  Met  Thr  Pro  Leu  Asn  Lys  Thr  Lys  Thr  Ala  Leu  Gly  Phe  Leu
 65                      70                  75                           80

Leu  Trp  Ile  Val  Cys  Trp  Ala  Asp  Leu  Phe  Tyr  Ser  Phe  Trp  Glu  Arg
               85                       90                       95

Ser  Arg  Gly  Ile  Phe  Leu  Ala  Pro  Val  Phe  Leu  Val  Ser  Pro  Thr  Leu
               100                      105                      110

Leu  Gly  Ile  Thr  Thr  Leu  Leu  Ala  Thr  Phe  Leu  Ile  Gln  Leu  Glu  Arg
          115                      120                      125

Arg  Lys  Gly  Val  Gln  Ser  Ser  Gly  Ile  Met  Leu  Thr  Phe  Trp  Leu  Val
     130                      135                      140

Ala  Leu  Val  Cys  Ala  Leu  Ala  Ile  Leu  Arg  Ser  Lys  Ile  Met  Thr  Ala
145                      150                      155                      160

Leu  Lys  Glu  Asp  Ala  Gln  Val  Asp  Leu  Phe  Arg  Asp  Ile  Thr  Phe  Tyr
               165                      170                      175

Val  Tyr  Phe  Ser  Leu  Leu  Leu  Ile  Gln  Leu  Val  Leu  Ser  Cys  Phe  Ser
               180                      185                      190

Asp  Arg  Ser  Pro  Leu  Phe  Ser  Glu  Thr  Ile  His  Asp  Pro  Asn  Pro  Cys
          195                      200                      205

Pro  Glu  Ser  Ser  Ala  Ser  Phe  Leu  Ser  Arg  Ile  Thr  Phe  Trp  Trp  Ile
     210                      215                      220

Thr  Gly  Leu  Ile  Val  Arg  Gly  Tyr  Arg  Gln  Pro  Leu  Glu  Gly  Ser  Asp
225                      230                      235                      240

Leu  Trp  Ser  Leu  Asn  Lys  Glu  Asp  Thr  Ser  Glu  Gln  Val  Val  Pro  Val
               245                      250                      255

Leu  Val  Lys  Asn  Trp  Lys  Lys  Glu  Cys  Ala  Lys  Thr  Arg  Lys  Gln  Pro
               260                      265                      270

Val  Lys  Val  Val  Tyr  Ser  Ser  Lys  Asp  Pro  Ala  Gln  Pro  Lys  Glu  Ser
          275                      280                      285

Ser  Lys  Val  Asp  Ala  Asn  Glu  Glu  Val  Glu  Ala  Leu  Ile  Val  Lys  Ser
     290                      295                      300

Pro  Gln  Lys  Glu  Trp  Asn  Pro  Ser  Leu  Phe  Lys  Val  Leu  Tyr  Lys  Thr
305                      310                      315                      320

Phe  Gly  Pro  Tyr  Phe  Leu  Met  Ser  Phe  Phe  Phe  Lys  Ala  Ile  His  Asp
               325                      330                      335

Leu  Met  Met  Phe  Ser  Gly  Pro  Gln  Ile  Leu  Lys  Leu  Leu  Ile  Lys  Phe
```

-continued

```
                        340                           345                          350
Val  Asn  Asp  Thr  Lys  Ala  Pro  Asp  Trp  Gln  Gly  Tyr  Phe  Tyr  Thr  Val
               355                      360                     365

Leu  Leu  Phe  Val  Thr  Ala  Cys  Leu  Gln  Thr  Leu  Val  Leu  His  Gln  Tyr
     370                     375                     380

Phe  His  Ile  Cys  Phe  Val  Ser  Gly  Met  Arg  Ile  Lys  Thr  Ala  Val  Ile
385                     390                     395                          400

Gly  Ala  Val  Tyr  Arg  Lys  Ala  Leu  Val  Ile  Thr  Asn  Ser  Ala  Arg  Lys
               405                     410                          415

Ser  Ser  Thr  Val  Gly  Glu  Ile  Val  Asn  Leu  Met  Ser  Val  Asp  Ala  Gln
               420                     425                     430

Arg  Phe  Met  Asp  Leu  Ala  Thr  Tyr  Ile  Asn  Met  Ile  Trp  Ser  Ala  Pro
          435                     440                     445

Leu  Gln  Val  Ile  Leu  Ala  Leu  Tyr  Leu  Leu  Trp  Leu  Asn  Leu  Gly  Pro
     450                     455                     460

Ser  Val  Leu  Ala  Gly  Val  Ala  Val  Met  Val  Leu  Met  Val  Pro  Val  Asn
465                     470                     475                     480

Ala  Val  Met  Ala  Met  Lys  Thr  Lys  Thr  Tyr  Gln  Val  Ala  His  Met  Lys
                    485                     490                     495

Ser  Lys  Asp  Asn  Arg  Ile  Lys  Leu  Met  Asn  Glu  Ile  Leu  Asn  Gly  Ile
               500                     505                     510

Lys  Val  Leu  Lys  Leu  Tyr  Ala  Trp  Glu  Leu  Ala  Phe  Lys  Asp  Lys  Val
          515                     520                     525

Leu  Ala  Ile  Arg  Gln  Glu  Glu  Leu  Lys  Val  Leu  Lys  Lys  Ser  Ala  Tyr
     530                     535                     540

Leu  Ser  Ala  Val  Gly  Thr  Phe  Thr  Trp  Val  Cys  Thr  Pro  Phe  Leu  Val
545                     550                     555                     560

Ala  Leu  Cys  Thr  Phe  Ala  Val  Tyr  Val  Thr  Ile  Asp  Glu  Asn  Asn  Ile
               565                     570                     575

Leu  Asp  Ala  Gln  Thr  Ala  Phe  Val  Ser  Leu  Ala  Leu  Phe  Asn  Ile  Leu
               580                     585                     590

Arg  Phe  Pro  Leu  Asn  Ile  Leu  Pro  Met  Val  Ile  Ser  Ser  Ile  Val  Gln
          595                     600                     605

Ala  Ser  Val  Ser  Leu  Lys  Arg  Leu  Arg  Ile  Phe  Leu  Ser  His  Glu  Glu
     610                     615                     620

Leu  Glu  Pro  Asp  Ser  Ile  Glu  Arg  Arg  Pro  Val  Lys  Asp  Gly  Gly  Gly
625                     630                     635                     640

Thr  Asn  Ser  Ile  Thr  Val  Arg  Asn  Ala  Thr  Phe  Thr  Trp  Ala  Arg  Ser
               645                     650                     655

Asp  Pro  Pro  Thr  Leu  Asn  Gly  Ile  Thr  Phe  Ser  Ile  Pro  Glu  Gly  Ala
               660                     665                     670

Leu  Val  Ala  Val  Val  Gly  Gln  Val  Gly  Cys  Gly  Lys  Ser  Ser  Leu  Leu
          675                     680                     685

Ser  Ala  Leu  Leu  Ala  Glu  Met  Asp  Lys  Val  Glu  Gly  His  Val  Ala  Ile
     690                     695                     700

Lys  Gly  Ser  Val  Ala  Tyr  Val  Pro  Gln  Gln  Ala  Trp  Ile  Gln  Asn  Asp
705                     710                     715                     720

Ser  Leu  Arg  Glu  Asn  Ile  Leu  Phe  Gly  Cys  Gln  Leu  Glu  Glu  Pro  Tyr
               725                     730                     735

Tyr  Arg  Ser  Val  Ile  Gln  Ala  Cys  Ala  Leu  Leu  Pro  Asp  Leu  Glu  Ile
               740                     745                     750

Leu  Pro  Ser  Gly  Asp  Arg  Thr  Glu  Ile  Gly  Glu  Lys  Gly  Val  Asn  Leu
          755                     760                     765
```

```
Ser Gly Gly Gln Lys Gln Arg Val Ser Leu Ala Arg Ala Val Tyr Ser
    770                 775                 780
Asn Ala Asp Ile Tyr Leu Phe Asp Asp Pro Leu Ser Ala Val Asp Ala
785                 790                 795                 800
His Val Gly Lys His Ile Phe Glu Asn Val Ile Gly Pro Lys Gly Met
                805                 810                 815
Leu Lys Asn Lys Thr Arg Ile Leu Val Thr His Ser Met Ser Tyr Leu
                820                 825                 830
Pro Gln Val Asp Val Ile Ile Val Met Ser Gly Gly Lys Ile Ser Glu
                835                 840                 845
Met Gly Ser Tyr Gln Glu Leu Leu Ala Arg Asp Gly Ala Phe Ala Glu
    850                 855                 860
Phe Leu Arg Thr Tyr Ala Ser Thr Glu Gln Glu Gln Asp Ala Glu Glu
865                 870                 875                 880
Asn Gly Val Thr Gly Val Ser Gly Pro Gly Lys Glu Ala Lys Gln Met
                885                 890                 895
Glu Asn Gly Met Leu Val Thr Asp Ser Ala Gly Lys Gln Leu Gln Arg
                900                 905                 910
Gln Leu Ser Ser Ser Ser Ser Tyr Ser Gly Asp Ile Ser Arg His His
                915                 920                 925
Asn Ser Thr Ala Glu Leu Gln Lys Ala Glu Ala Lys Lys Glu Glu Thr
930                 935                 940
Trp Lys Leu Met Glu Ala Asp Lys Ala Gln Thr Gly Gln Val Lys Leu
945                 950                 955                 960
Ser Val Tyr Trp Asp Tyr Met Lys Ala Ile Gly Leu Phe Ile Ser Phe
                965                 970                 975
Leu Ser Ile Phe Leu Phe Met Cys Asn His Val Ser Ala Leu Ala Ser
                980                 985                 990
Asn Tyr Trp Leu Ser Leu Trp Thr Asp Asp Pro Ile Val Asn Gly Thr
                995                 1000                1005
Gln Glu His Thr Lys Val Arg Leu Ser Val Tyr Gly Ala Leu Gly Ile
                1010                1015                1020
Ser Gln Gly Ile Ala Val Phe Gly Tyr Ser Met Ala Val Ser Ile Gly
1025                1030                1035                1040
Gly Ile Leu Ala Ser Arg Cys Leu His Val Asp Leu Leu His Ser Ile
                1045                1050                1055
Leu Arg Ser Pro Met Ser Phe Phe Glu Arg Thr Pro Ser Gly Asn Leu
                1060                1065                1070
Val Asn Arg Phe Ser Lys Glu Leu Asp Thr Val Asp Ser Met Ile Pro
                1075                1080                1085
Glu Val Ile Lys Met Phe Met Gly Ser Leu Phe Asn Val Ile Gly Ala
                1090                1095                1100
Cys Ile Val Ile Leu Leu Ala Thr Pro Ile Ala Ala Ile Ile Ile Pro
1105                1110                1115                1120
Pro Leu Gly Leu Ile Tyr Phe Phe Val Gln Arg Phe Tyr Val Ala Ser
                1125                1130                1135
Ser Arg Gln Leu Lys Arg Leu Glu Ser Val Ser Arg Ser Pro Val Tyr
                1140                1145                1150
Ser His Phe Asn Glu Thr Leu Leu Gly Val Ser Val Ile Arg Ala Phe
                1155                1160                1165
Glu Glu Gln Glu Arg Phe Ile His Gln Ser Asp Leu Lys Val Asp Glu
                1170                1175                1180
Asn Gln Lys Ala Tyr Tyr Pro Ser Ile Val Ala Asn Arg Trp Leu Ala
1185                1190                1195                1200
```

Val Arg Leu Glu Cys Val Gly Asn Cys Ile Val Leu Phe Ala Ala Leu
              1205                1210                1215

Phe Ala Val Ile Ser Arg His Ser Leu Ser Ala Gly Leu Val Gly Leu
              1220                1225                1230

Ser Val Ser Tyr Ser Leu Gln Val Thr Thr Tyr Leu Asn Trp Leu Val
              1235                1240                1245

Arg Met Ser Ser Glu Met Glu Thr Asn Ile Val Ala Val Glu Arg Leu
          1250                1255                1260

Lys Glu Tyr Ser Glu Thr Glu Lys Glu Ala Pro Trp Gln Ile Gln Glu
1265                1270                1275                1280

Thr Ala Pro Pro Ser Ser Trp Pro Gln Val Gly Arg Val Glu Phe Arg
              1285                1290                1295

Asn Tyr Cys Leu Arg Tyr Arg Glu Asp Leu Asp Phe Val Leu Arg His
              1300                1305                1310

Ile Asn Val Thr Ile Asn Gly Gly Glu Lys Val Gly Ile Val Gly Arg
              1315                1320                1325

Thr Gly Ala Gly Lys Ser Ser Leu Thr Leu Gly Leu Phe Arg Ile Asn
          1330                1335                1340

Glu Ser Ala Glu Gly Glu Ile Ile Ile Asp Gly Ile Asn Ile Ala Lys
1345                1350                1355                1360

Ile Gly Leu His Asp Leu Arg Phe Lys Ile Thr Ile Ile Pro Gln Asp
              1365                1370                1375

Pro Val Leu Phe Ser Gly Ser Leu Arg Met Asn Leu Asp Pro Phe Ser
              1380                1385                1390

Gln Tyr Ser Asp Glu Glu Val Trp Thr Ser Leu Glu Leu Ala His Leu
              1395                1400                1405

Lys Asp Phe Val Ser Ala Leu Pro Asp Lys Leu Asp His Glu Cys Ala
          1410                1415                1420

Glu Gly Gly Glu Asn Leu Ser Val Gly Gln Arg Gln Leu Val Cys Leu
1425                1430                1435                1440

Ala Arg Ala Leu Leu Arg Lys Thr Lys Ile Leu Val Leu Asp Glu Ala
              1445                1450                1455

Thr Ala Ala Val Asp Leu Glu Thr Asp Asp Leu Ile Gln Ser Thr Ile
              1460                1465                1470

Arg Thr Gln Phe Glu Asp Cys Thr Val Leu Thr Ile Ala His Arg Leu
          1475                1480                1485

Asn Thr Ile Met Asp Tyr Thr Arg Val Ile Val Leu Asp Lys Gly Glu
          1490                1495                1500

Ile Gln Glu Tyr Gly Ala Pro Ser Asp Leu Leu Gln Gln Arg Gly Leu
1505                1510                1515                1520

Phe Tyr Ser Met Ala Lys Asp Ala Gly Leu Val
              1525                1530

( 2 ) INFORMATION FOR SEQ ID NO:5:

( i ) SEQUENCE CHARACTERISTICS:
        ( A ) LENGTH: 5889 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 6 4589

( x i ) SEQUENCE DESCRIPTION: SEQ ID NO:5:

|       |       |       |       |       |       |       |       |       |       |       |       |       |       |       |       |     |
|-------|-------|-------|-------|-------|-------|-------|-------|-------|-------|-------|-------|-------|-------|-------|-------|-----|
| CCCGC | ATG   | GCG   | CTG   | CGC   | AGC   | TTC   | TGC   | AGC   | GCT   | GAT   | GGC   | TCC   | GAT   | CCA   |       | 47  |
|       | Met 1 | Ala   | Leu   | Arg   | Ser 5 | Phe   | Cys   | Ser   | Ala   | Asp 10| Gly   | Ser   | Asp   | Pro   |       |     |
| CTC   | TGG   | GAC   | TGG   | AAT   | GTC   | ACA   | TGG   | CAC   | ACC   | AGC   | AAC   | CCC   | GAC   | TTT   | ACC   | 95  |
| Leu 15| Trp   | Asp   | Trp   | Asn   | Val 20| Thr   | Trp   | His   | Thr   | Ser 25| Asn   | Pro   | Asp   | Phe   | Thr 30|     |
| AAG   | TGC   | TTT   | CAG   | AAC   | ACG   | GTC   | CTC   | ACA   | TGG   | GTG   | CCT   | TGT   | TTC   | TAC   | CTC   | 143 |
| Lys   | Cys   | Phe   | Gln   | Asn 35| Thr   | Val   | Leu   | Thr   | Trp 40| Val   | Pro   | Cys   | Phe   | Tyr 45| Leu   |     |
| TGG   | TCC   | TGT   | TTC   | CCC   | CTC   | TAC   | TTC   | TTC   | TAT   | CTC   | TCT   | CGC   | CAT   | GAC   | CGG   | 191 |
| Trp   | Ser   | Cys   | Phe 50| Pro   | Leu   | Tyr   | Phe   | Phe 55| Tyr   | Leu   | Ser   | Arg   | His 60| Asp   | Arg   |     |
| GGC   | TAC   | ATC   | CAG   | ATG   | ACA   | CAC   | CTC   | AAC   | AAA   | ACC   | AAA   | ACT   | GCC   | TTA   | GGA   | 239 |
| Gly   | Tyr   | Ile 65| Gln   | Met   | Thr   | His   | Leu 70| Asn   | Lys   | Thr   | Lys   | Thr 75| Ala   | Leu   | Gly   |     |
| TTC   | TTT   | CTG   | TGG   | ATC   | ATC   | TGC   | TGG   | GCA   | GAC   | CTC   | TTC   | TAC   | TCT   | TTC   | TGG   | 287 |
| Phe   | Phe 80| Leu   | Trp   | Ile   | Ile   | Cys 85| Trp   | Ala   | Asp   | Leu   | Phe 90| Tyr   | Ser   | Phe   | Trp   |     |
| GAA   | AGA   | AGT   | CAG   | GGA   | GTG   | CTC   | CGA   | GCC   | CCG   | GTG   | TTA   | CTG   | GTC   | AGC   | CCA   | 335 |
| Glu 95| Arg   | Ser   | Gln   | Gly 100| Val   | Leu   | Arg   | Ala   | Pro 105| Val   | Leu   | Leu   | Val   | Ser 110| Pro  |     |
| ACA   | CTG   | CTG   | GGC   | ATC   | ACC   | ATG   | CTG   | CTC   | GCC   | ACC   | TTT   | TTG   | ATA   | CAG   | CTT   | 383 |
| Thr   | Leu   | Leu   | Gly   | Ile 115| Thr  | Met   | Leu   | Leu 120| Ala  | Thr   | Phe   | Leu   | Ile 125| Gln  | Leu   |     |
| GAA   | CGG   | AGG   | AAG   | GGA   | GTC   | CAA   | TCC   | TCG   | GGA   | ATT   | ATG   | CTT   | ACT   | TTC   | TGG   | 431 |
| Glu   | Arg   | Arg   | Lys 130| Gly  | Val   | Gln   | Ser   | Ser 135| Gly  | Ile   | Met   | Leu   | Thr 140| Phe  | Trp   |     |
| CTC   | GTA   | GCC   | CTA   | CTC   | TGT   | GCC   | CTT   | GCC   | ATC   | TTG   | AGA   | TCT   | AAG   | ATC   | ATC   | 479 |
| Leu   | Val   | Ala 145| Leu  | Leu   | Cys   | Ala   | Leu 150| Ala  | Ile   | Leu   | Arg   | Ser 155| Lys  | Ile   | Ile   |     |
| TCT   | GCC   | TTA   | AAA   | AAG   | GAT   | GCT   | CAT   | GTG   | GAC   | GTG   | TTT   | CGA   | GAT   | TCC   | ACG   | 527 |
| Ser   | Ala 160| Leu  | Lys   | Lys   | Asp   | Ala 165| His  | Val   | Asp   | Val   | Phe 170| Arg  | Asp   | Ser   | Thr   |     |
| TTC   | TAT   | CTG   | TAC   | TTC   | ACC   | CTT   | GTG   | CTT   | GTT   | CAG   | CTC   | GTG   | CTG   | TCC   | TGC   | 575 |
| Phe 175| Tyr  | Leu   | Tyr   | Phe   | Thr 180| Leu  | Val   | Leu   | Val   | Gln 185| Leu  | Val   | Leu   | Ser   | Cys 190|    |
| TTC   | TCA   | GAC   | TGC   | TCA   | CCC   | CTG   | TTC   | TCT   | GAA   | ACT   | GTC   | CAT   | GAC   | CGG   | AAT   | 623 |
| Phe   | Ser   | Asp   | Cys   | Ser 195| Pro  | Leu   | Phe   | Ser   | Glu 200| Thr  | Val   | His   | Asp   | Arg 205| Asn  |     |
| CCA   | TGC   | CCA   | GAA   | TCC   | AGT   | GCC   | TCT   | TTC   | CTT   | TCC   | AGG   | ATT   | ACT   | TTC   | TGG   | 671 |
| Pro   | Cys   | Pro   | Glu 210| Ser  | Ser   | Ala   | Ser   | Phe 215| Leu  | Ser   | Arg   | Ile   | Thr 220| Phe  | Trp   |     |
| TGG   | ATT   | ACA   | GGG   | ATG   | ATG   | GTG   | CAC   | GGC   | TAC   | CGC   | CAG   | CCC   | CTG   | GAG   | AGC   | 719 |
| Trp   | Ile   | Thr 225| Gly  | Met   | Met   | Val   | His 230| Gly  | Tyr   | Arg   | Gln   | Pro 235| Leu  | Glu   | Ser   |     |
| AGT   | GAC   | CTC   | TGG   | TCA   | TTG   | AAT   | AAG   | GAG   | GAC   | ACA   | TCA   | GAA   | GAA   | GTG   | GTA   | 767 |
| Ser   | Asp   | Leu 240| Trp  | Ser   | Leu   | Asn   | Lys 245| Glu  | Asp   | Thr   | Ser   | Glu 250| Glu  | Val   | Val   |     |
| CCT   | GTG   | CTG   | GTG   | AAT   | AAC   | TGG   | AAG   | AAG   | GAA   | TGT   | GAT   | AAG   | TCA   | AGG   | AAG   | 815 |
| Pro 255| Val  | Leu   | Val   | Asn   | Asn 260| Trp  | Lys   | Lys   | Glu   | Cys 265| Asp  | Lys   | Ser   | Arg   | Lys 270|    |
| CAG   | CCT   | GTA   | CGG   | ATT   | GTG   | TAT   | GCC   | CCT   | CCC   | AAA   | GAT   | CCC   | AGC   | AAG   | CCT   | 863 |
| Gln   | Pro   | Val   | Arg   | Ile 275| Val  | Tyr   | Ala   | Pro   | Pro 280| Lys  | Asp   | Pro   | Ser   | Lys 285| Pro  |     |
| AAG   | GGA   | AGT   | TCC   | CAG   | TTG   | GAT   | GTG   | AAT   | GAG   | GAG   | GTG   | GAG   | GCA   | CTG   | ATT   | 911 |
| Lys   | Gly   | Ser   | Ser   | Gln 290| Leu  | Asp   | Val   | Asn   | Glu 295| Glu  | Val   | Glu   | Ala   | Leu 300| Ile  |     |
| GTC   | AAG   | TCA   | CCC   | CAC   | AAG   | GAT   | CGG   | GAG   | CCC   | TCT   | CTG   | TTC   | AAG   | GTG   | TTA   | 959 |
| Val   | Lys   | Ser 305| Pro  | His   | Lys   | Asp   | Arg 310| Glu  | Pro   | Ser   | Leu   | Phe 315| Lys  | Val   | Leu   |     |

| | | | | | | | | | | | | | | | | |
|---|---|---|---|---|---|---|---|---|---|---|---|---|---|---|---|---|
| TAC | AAG | ACT | TTT | GGT | CCC | TAC | TTC | CTC | ATG | AGC | TTC | CTG | TAC | AAG | GCC | 1007 |
| Tyr | Lys | Thr | Phe | Gly | Pro | Tyr | Phe | Leu | Met | Ser | Phe | Leu | Tyr | Lys | Ala | |
| | 320 | | | | 325 | | | | | 330 | | | | | | |
| CTT | CAT | GAC | CTG | ATG | ATG | TTT | GCC | GGC | CCC | AAG | ATC | TTG | GAA | TTG | ATT | 1055 |
| Leu | His | Asp | Leu | Met | Met | Phe | Ala | Gly | Pro | Lys | Ile | Leu | Glu | Leu | Ile | |
| 335 | | | | | 340 | | | | | 345 | | | | | 350 | |
| ATC | AAC | TTC | GTG | AAT | GAC | AGG | GAG | GCT | CCC | GAC | TGG | CAG | GGC | TAC | TTT | 1103 |
| Ile | Asn | Phe | Val | Asn | Asp | Arg | Glu | Ala | Pro | Asp | Trp | Gln | Gly | Tyr | Phe | |
| | | | | 355 | | | | | 360 | | | | | 365 | | |
| TAC | ACA | GCA | CTG | CTG | TTT | GTC | AGC | GCC | TGT | CTG | CAG | ACA | CTG | GCA | CTC | 1151 |
| Tyr | Thr | Ala | Leu | Leu | Phe | Val | Ser | Ala | Cys | Leu | Gln | Thr | Leu | Ala | Leu | |
| | | | 370 | | | | 375 | | | | | 380 | | | | |
| CAC | CAG | TAC | TTT | CAT | ATC | TGC | TTC | GTC | AGT | GGC | ATG | CGC | ATC | AAG | ACT | 1199 |
| His | Gln | Tyr | Phe | His | Ile | Cys | Phe | Val | Ser | Gly | Met | Arg | Ile | Lys | Thr | |
| | | 385 | | | | 390 | | | | | 395 | | | | | |
| GCT | GTG | GTG | GGC | GCT | GTC | TAT | CGT | AAG | GCT | CTT | TTG | ATC | ACC | AAT | GCA | 1247 |
| Ala | Val | Val | Gly | Ala | Val | Tyr | Arg | Lys | Ala | Leu | Leu | Ile | Thr | Asn | Ala | |
| | | 400 | | | | 405 | | | | | 410 | | | | | |
| GCT | AGA | AAA | TCT | TCC | ACG | GTC | GGA | GAG | ATT | GTC | AAC | CTC | ATG | TCC | GTG | 1295 |
| Ala | Arg | Lys | Ser | Ser | Thr | Val | Gly | Glu | Ile | Val | Asn | Leu | Met | Ser | Val | |
| 415 | | | | | 420 | | | | | 425 | | | | | 430 | |
| GAT | GCT | CAG | CGC | TTC | ATG | GAC | TTG | GCC | ACG | TAC | ATT | AAC | ATG | ATC | TGG | 1343 |
| Asp | Ala | Gln | Arg | Phe | Met | Asp | Leu | Ala | Thr | Tyr | Ile | Asn | Met | Ile | Trp | |
| | | | | 435 | | | | | 440 | | | | | 445 | | |
| TCA | GCC | CCT | CTG | CAA | GTC | ATC | CTA | GCC | CTC | TAC | TTC | CTG | TGG | CTG | AGC | 1391 |
| Ser | Ala | Pro | Leu | Gln | Val | Ile | Leu | Ala | Leu | Tyr | Phe | Leu | Trp | Leu | Ser | |
| | | | 450 | | | | 455 | | | | | 460 | | | | |
| CTG | GGC | CCT | TCT | GTG | CTG | GCT | GGA | GTG | GCT | GTG | ATG | ATT | CTC | ATG | GTA | 1439 |
| Leu | Gly | Pro | Ser | Val | Leu | Ala | Gly | Val | Ala | Val | Met | Ile | Leu | Met | Val | |
| | | 465 | | | | | 470 | | | | | 475 | | | | |
| CCC | TTA | AAT | GCT | GTG | ATG | GCC | ATG | AAG | ACC | AAG | ACC | TAC | CAG | GTG | GCA | 1487 |
| Pro | Leu | Asn | Ala | Val | Met | Ala | Met | Lys | Thr | Lys | Thr | Tyr | Gln | Val | Ala | |
| | 480 | | | | | 485 | | | | | 490 | | | | | |
| CAC | ATG | AAG | AGC | AAA | GAC | AAC | CGA | ATC | AAG | CTG | ATG | AAC | GAG | ATC | CTC | 1535 |
| His | Met | Lys | Ser | Lys | Asp | Asn | Arg | Ile | Lys | Leu | Met | Asn | Glu | Ile | Leu | |
| 495 | | | | | 500 | | | | | 505 | | | | | 510 | |
| AAT | GGG | ATC | AAA | GTC | CTC | AAG | CTG | TAC | GCC | TGG | GAG | CTG | GCC | TTC | CAG | 1583 |
| Asn | Gly | Ile | Lys | Val | Leu | Lys | Leu | Tyr | Ala | Trp | Glu | Leu | Ala | Phe | Gln | |
| | | | | 515 | | | | | 520 | | | | | 525 | | |
| GAC | AAA | GTC | ATG | AGC | ATC | AGG | CAG | GAG | GAG | CTC | AAG | GTG | CTG | AAG | AAA | 1631 |
| Asp | Lys | Val | Met | Ser | Ile | Arg | Gln | Glu | Glu | Leu | Lys | Val | Leu | Lys | Lys | |
| | | | 530 | | | | 535 | | | | | 540 | | | | |
| TCT | GCC | TAC | CTG | GCA | GCT | GTA | GGC | ACA | TTC | ACG | TGG | GTG | TGC | ACA | CCT | 1679 |
| Ser | Ala | Tyr | Leu | Ala | Ala | Val | Gly | Thr | Phe | Thr | Trp | Val | Cys | Thr | Pro | |
| | | 545 | | | | | 550 | | | | | 555 | | | | |
| TTC | CTG | GTG | GCC | CTG | TCA | ACC | TTT | GCT | GTC | TTT | GTG | ACT | GTG | GAT | GAG | 1727 |
| Phe | Leu | Val | Ala | Leu | Ser | Thr | Phe | Ala | Val | Phe | Val | Thr | Val | Asp | Glu | |
| | | 560 | | | | | 565 | | | | | 570 | | | | |
| AGA | AAT | ATC | CTA | GAT | GCA | AAG | AAA | GCC | TTT | GTG | TCC | CTA | GCC | CTG | TTC | 1775 |
| Arg | Asn | Ile | Leu | Asp | Ala | Lys | Lys | Ala | Phe | Val | Ser | Leu | Ala | Leu | Phe | |
| 575 | | | | | 580 | | | | | 585 | | | | | 590 | |
| AAT | ATC | TTG | CGC | TTC | CCA | CTC | AAC | ATC | CTG | CCC | ATG | GTT | ATC | AGC | AGC | 1823 |
| Asn | Ile | Leu | Arg | Phe | Pro | Leu | Asn | Ile | Leu | Pro | Met | Val | Ile | Ser | Ser | |
| | | | | 595 | | | | | 600 | | | | | 605 | | |
| ATT | GTG | CAG | GCC | AGC | GTG | TCC | CTC | AAG | CGT | CTC | AGG | ATT | TTT | CTG | TCT | 1871 |
| Ile | Val | Gln | Ala | Ser | Val | Ser | Leu | Lys | Arg | Leu | Arg | Ile | Phe | Leu | Ser | |
| | | | 610 | | | | 615 | | | | | 620 | | | | |
| CAT | GAG | GAG | CTG | GAG | CCA | GAC | AGC | ATT | GAG | CGG | AGG | TCG | ATC | AAG | AGT | 1919 |
| His | Glu | Glu | Leu | Glu | Pro | Asp | Ser | Ile | Glu | Arg | Arg | Ser | Ile | Lys | Ser | |
| | | 625 | | | | | 630 | | | | | 635 | | | | |

| | | | | | | | | | | | | | | | | |
|---|---|---|---|---|---|---|---|---|---|---|---|---|---|---|---|---|
| GGA | GAA | GGG | AAT | AGC | ATC | ACT | GTG | AAG | AAT | GCA | ACC | TTC | ACT | TGG | GCC | 1967 |
| Gly | Glu | Gly | Asn | Ser | Ile | Thr | Val | Lys | Asn | Ala | Thr | Phe | Thr | Trp | Ala | |
| 640 | | | | | 645 | | | | | 650 | | | | | | |
| AGG | GGT | GAA | CCT | CCC | ACA | CTG | AAT | GGC | ATC | ACC | TTC | TCC | ATT | CCT | GAA | 2015 |
| Arg | Gly | Glu | Pro | Pro | Thr | Leu | Asn | Gly | Ile | Thr | Phe | Ser | Ile | Pro | Glu | |
| 655 | | | | | 660 | | | | | 665 | | | | | 670 | |
| GGA | GCC | CTT | GTG | GCC | GTG | GTG | GGC | CAG | GTA | GGC | TGC | GGG | AAG | TCA | TCT | 2063 |
| Gly | Ala | Leu | Val | Ala | Val | Val | Gly | Gln | Val | Gly | Cys | Gly | Lys | Ser | Ser | |
| | | | | 675 | | | | | 680 | | | | | 685 | | |
| CTG | CTG | TCA | GCC | CTG | CTG | GCT | GAG | ATG | GAC | AAG | GTG | GAG | GGA | CAT | GTG | 2111 |
| Leu | Leu | Ser | Ala | Leu | Leu | Ala | Glu | Met | Asp | Lys | Val | Glu | Gly | His | Val | |
| | | | 690 | | | | | 695 | | | | | 700 | | | |
| ACT | CTC | AAG | GGC | TCC | GTG | GCC | TAC | GTG | CCC | CAG | CAG | GCC | TGG | ATT | CAG | 2159 |
| Thr | Leu | Lys | Gly | Ser | Val | Ala | Tyr | Val | Pro | Gln | Gln | Ala | Trp | Ile | Gln | |
| | | 705 | | | | | 710 | | | | | 715 | | | | |
| AAT | GAC | TCT | CTC | CGA | GAG | AAC | ATA | CTG | TTT | GGG | CAC | CCC | CTG | CAG | GAA | 2207 |
| Asn | Asp | Ser | Leu | Arg | Glu | Asn | Ile | Leu | Phe | Gly | His | Pro | Leu | Gln | Glu | |
| 720 | | | | | 725 | | | | | 730 | | | | | | |
| AAT | TAC | TAC | AAG | GCA | GTT | ATG | GAA | GCC | TGT | GCC | CTT | CTT | CCA | GAT | TTG | 2255 |
| Asn | Tyr | Tyr | Lys | Ala | Val | Met | Glu | Ala | Cys | Ala | Leu | Leu | Pro | Asp | Leu | |
| 735 | | | | | 740 | | | | | 745 | | | | | 750 | |
| GAA | ATC | CTG | CCC | AGT | GGG | GAC | CGC | ACA | GAG | ATC | GGT | GAG | AAG | GGT | GTG | 2303 |
| Glu | Ile | Leu | Pro | Ser | Gly | Asp | Arg | Thr | Glu | Ile | Gly | Glu | Lys | Gly | Val | |
| | | | | 755 | | | | | 760 | | | | | 765 | | |
| AAC | CTG | TCA | GGG | GGC | CAG | AAG | CAG | CGT | GTG | AGC | CTG | GCC | CGG | GCT | GTG | 2351 |
| Asn | Leu | Ser | Gly | Gly | Gln | Lys | Gln | Arg | Val | Ser | Leu | Ala | Arg | Ala | Val | |
| | | | 770 | | | | | 775 | | | | | 780 | | | |
| TAC | TCT | AAC | TCT | GAC | ATC | TAC | CTC | TTT | GAT | GAC | CCC | CTC | TCG | GCT | GTG | 2399 |
| Tyr | Ser | Asn | Ser | Asp | Ile | Tyr | Leu | Phe | Asp | Asp | Pro | Leu | Ser | Ala | Val | |
| | | 785 | | | | | 790 | | | | | 795 | | | | |
| GAT | GCA | CAT | GTT | GGG | AAG | CAC | ATC | TTT | GAG | AAG | GTG | GTT | GGT | CCC | ATG | 2447 |
| Asp | Ala | His | Val | Gly | Lys | His | Ile | Phe | Glu | Lys | Val | Val | Gly | Pro | Met | |
| 800 | | | | | 805 | | | | | 810 | | | | | | |
| GGC | CTA | CTG | AAG | AAC | AAG | ACA | CGG | ATC | CTG | GTC | ACC | CAT | GGT | ATC | AGC | 2495 |
| Gly | Leu | Leu | Lys | Asn | Lys | Thr | Arg | Ile | Leu | Val | Thr | His | Gly | Ile | Ser | |
| 815 | | | | | 820 | | | | | 825 | | | | | 830 | |
| TAC | CTG | CCC | CAA | GTG | GAT | GTC | ATC | ATT | GTC | ATG | AGT | GGC | GGC | AAG | ATC | 2543 |
| Tyr | Leu | Pro | Gln | Val | Asp | Val | Ile | Ile | Val | Met | Ser | Gly | Gly | Lys | Ile | |
| | | | | 835 | | | | | 840 | | | | | 845 | | |
| TCA | GAG | ATG | GGT | TCT | TAT | CAG | GAG | CTG | CTA | GAC | CGG | GAT | GGG | GCC | TTC | 2591 |
| Ser | Glu | Met | Gly | Ser | Tyr | Gln | Glu | Leu | Leu | Asp | Arg | Asp | Gly | Ala | Phe | |
| | | | 850 | | | | | 855 | | | | | 860 | | | |
| GCT | GAG | TTC | CTG | CGC | ACC | TAT | GCC | AAC | GCT | GAG | CAG | GAC | CTG | GCC | TCG | 2639 |
| Ala | Glu | Phe | Leu | Arg | Thr | Tyr | Ala | Asn | Ala | Glu | Gln | Asp | Leu | Ala | Ser | |
| | | 865 | | | | | 870 | | | | | 875 | | | | |
| GAG | GAT | GAC | AGT | GTC | AGT | GGT | TCA | GGG | AAG | GAG | TCA | AAG | CCG | GTG | GAA | 2687 |
| Glu | Asp | Asp | Ser | Val | Ser | Gly | Ser | Gly | Lys | Glu | Ser | Lys | Pro | Val | Glu | |
| | | 880 | | | | | 885 | | | | | 890 | | | | |
| AAT | GGG | ATG | CTG | GTG | ACA | GAC | ACC | GTA | GGA | AAG | CAC | CTG | CAG | AGG | CAT | 2735 |
| Asn | Gly | Met | Leu | Val | Thr | Asp | Thr | Val | Gly | Lys | His | Leu | Gln | Arg | His | |
| 895 | | | | | 900 | | | | | 905 | | | | | 910 | |
| CTC | AGC | AAC | TCG | TCT | TCC | CAC | AGT | GGG | GAT | ACC | AGC | CAG | CAA | CAC | AGC | 2783 |
| Leu | Ser | Asn | Ser | Ser | Ser | His | Ser | Gly | Asp | Thr | Ser | Gln | Gln | His | Ser | |
| | | | | 915 | | | | | 920 | | | | | 925 | | |
| AGC | ATA | GCC | GAA | CTG | CAG | AAG | GCT | GGA | GCT | AAG | GAG | GAG | ACG | TGG | AAG | 2831 |
| Ser | Ile | Ala | Glu | Leu | Gln | Lys | Ala | Gly | Ala | Lys | Glu | Glu | Thr | Trp | Lys | |
| | | | | 930 | | | | | 935 | | | | | 940 | | |
| CTA | ATG | GAA | GCA | GAC | AAG | GCC | CAG | ACA | GGG | CAG | GTG | CAG | CTG | TCA | GTG | 2879 |
| Leu | Met | Glu | Ala | Asp | Lys | Ala | Gln | Thr | Gly | Gln | Val | Gln | Leu | Ser | Val | |
| | | 945 | | | | | 950 | | | | | 955 | | | | |

```
TAC TGG AAC TAC ATG AAG GCC ATT GGC CTC TTC ATC ACC TTC TTG AGT    2927
Tyr Trp Asn Tyr Met Lys Ala Ile Gly Leu Phe Ile Thr Phe Leu Ser
960                 965                 970

ATC TTC CTT TTC CTG TGC AAC CAT GTA TCT GCA CTG GCC TCT AAC TAT    2975
Ile Phe Leu Phe Leu Cys Asn His Val Ser Ala Leu Ala Ser Asn Tyr
975                 980                 985                 990

TGG CTG AGC CTC TGG ACA GAT GAC CCC CCT GTT GTC AAT GGG ACT CAG    3023
Trp Leu Ser Leu Trp Thr Asp Asp Pro Pro Val Val Asn Gly Thr Gln
                995                 1000                1005

GCG AAC AGG AAT TTT CGG CTG AGT GTC TAT GGG GCC TTG GGC ATC TTG    3071
Ala Asn Arg Asn Phe Arg Leu Ser Val Tyr Gly Ala Leu Gly Ile Leu
        1010                1015                1020

CAA GGT GCA GCA ATA TTT GGC TAC TCC ATG GCT GTG TCC ATC GGG GGC    3119
Gln Gly Ala Ala Ile Phe Gly Tyr Ser Met Ala Val Ser Ile Gly Gly
    1025                1030                1035

ATC TTT GCC TCC CGT CGC TTG CAC CTG GAC CTG CTA TAC AAT GTT CTT    3167
Ile Phe Ala Ser Arg Arg Leu His Leu Asp Leu Leu Tyr Asn Val Leu
1040                1045                1050

CGA TCA CCC ATG AGT TTC TTC GAG CGT ACA CCC AGT GGG AAC CTA GTG    3215
Arg Ser Pro Met Ser Phe Phe Glu Arg Thr Pro Ser Gly Asn Leu Val
1055                1060                1065                1070

AAC CGA TTC TCC AAG GAG CTG GAC ACA GTG GAC TCC ATG ATC CCG CAG    3263
Asn Arg Phe Ser Lys Glu Leu Asp Thr Val Asp Ser Met Ile Pro Gln
                1075                1080                1085

GTC ATC AAG ATG TTC ATG GGT TCA CTC TTC AGT GTC ATT GGA GCT GTC    3311
Val Ile Lys Met Phe Met Gly Ser Leu Phe Ser Val Ile Gly Ala Val
        1090                1095                1100

ATC ATC ATC CTA CTG GCC ACG CCC ATT GCC GCA GTC ATC ATC CCA CCC    3359
Ile Ile Ile Leu Leu Ala Thr Pro Ile Ala Ala Val Ile Ile Pro Pro
    1105                1110                1115

TTG GGT CTG GTT TAC TTC TTT GTG CAG AGG TTC TAT GTG GCT TCC TCA    3407
Leu Gly Leu Val Tyr Phe Phe Val Gln Arg Phe Tyr Val Ala Ser Ser
1120                1125                1130

AGA CAA CTG AAG CGC CTG GAG TCT GTC AGC CGT TCC CCT GTG TAC TCA    3455
Arg Gln Leu Lys Arg Leu Glu Ser Val Ser Arg Ser Pro Val Tyr Ser
1135                1140                1145                1150

CAC TTC AAT GAG ACC TTG CTG GGA GTC AGT GTC ATC CGT GCT TTT GAG    3503
His Phe Asn Glu Thr Leu Leu Gly Val Ser Val Ile Arg Ala Phe Glu
                1155                1160                1165

GAG CAG GAG CGC TTC ATT CAC CAG AGT GAC CTG AAA GTA GAT GAG AAC    3551
Glu Gln Glu Arg Phe Ile His Gln Ser Asp Leu Lys Val Asp Glu Asn
        1170                1175                1180

CAG AAG GCC TAC TAC CCC AGC ATT GTG GCC AAC AGA TGG CTT GCT GTG    3599
Gln Lys Ala Tyr Tyr Pro Ser Ile Val Ala Asn Arg Trp Leu Ala Val
    1185                1190                1195

CGC CTT GAG TGT GTG GGC AAC TGC ATT GTG CTG TTT GCT GCC CTC TTT    3647
Arg Leu Glu Cys Val Gly Asn Cys Ile Val Leu Phe Ala Ala Leu Phe
1200                1205                1210

GCA GTC ATC TCC CGG CAC AGC CTC AGT GCT GGC TTG GTG GGC CTC TCT    3695
Ala Val Ile Ser Arg His Ser Leu Ser Ala Gly Leu Val Gly Leu Ser
1215                1220                1225                1230

GTG TCT TAC TCA CTG CAG ATA ACT GCA TAC TTG AAC TGG CTG GTT CGA    3743
Val Ser Tyr Ser Leu Gln Ile Thr Ala Tyr Leu Asn Trp Leu Val Arg
                1235                1240                1245

ATG TCC TCG GAG ATG GAG ACC AAC ATT GTG GCA GTG GAG AGA CTG AAG    3791
Met Ser Ser Glu Met Glu Thr Asn Ile Val Ala Val Glu Arg Leu Lys
        1250                1255                1260

GAG TAT TCT GAA ACA GAG AAG GAG GCT CCT TGG CAA ATC CAG GAA ACA    3839
Glu Tyr Ser Glu Thr Glu Lys Glu Ala Pro Trp Gln Ile Gln Glu Thr
    1265                1270                1275
```

| | | | | | | | | | | | | | | | | |
|---|---|---|---|---|---|---|---|---|---|---|---|---|---|---|---|---|
| GCT | CCA | CCC | AGC | ACC | TGG | CCC | CAT | TCA | GGC | CGT | GTA | GAG | TTC | CGG | GAT | 3887 |
| Ala | Pro | Pro | Ser | Thr | Trp | Pro | His | Ser | Gly | Arg | Val | Glu | Phe | Arg | Asp | |
| 1280 | | | | | 1285 | | | | | 1290 | | | | | | |
| TAC | TGC | CTG | AGG | TAT | CGA | GAA | GAC | TTG | GAC | TTG | GTT | CTC | AAG | CAC | ATA | 3935 |
| Tyr | Cys | Leu | Arg | Tyr | Arg | Glu | Asp | Leu | Asp | Leu | Val | Leu | Lys | His | Ile | |
| 1295 | | | | | 1300 | | | | | 1305 | | | | | 1310 | |
| AAT | GTC | ACC | ATT | GAG | GGT | GGA | GAA | AAG | GTG | GGT | ATT | GTA | GGT | CGT | ACG | 3983 |
| Asn | Val | Thr | Ile | Glu | Gly | Gly | Glu | Lys | Val | Gly | Ile | Val | Gly | Arg | Thr | |
| | | | | 1315 | | | | | 1320 | | | | | 1325 | | |
| GGA | GCT | GGG | AAA | TCA | TCT | CTC | ACC | CTG | GGT | TTG | TTC | CGG | ATC | AAT | GAG | 4031 |
| Gly | Ala | Gly | Lys | Ser | Ser | Leu | Thr | Leu | Gly | Leu | Phe | Arg | Ile | Asn | Glu | |
| | | | 1330 | | | | | 1335 | | | | | 1340 | | | |
| TCT | GCA | GAA | GGG | GAG | ATC | ATC | ATT | GAT | GGG | GTC | AAC | ATC | GCC | AAG | ATC | 4079 |
| Ser | Ala | Glu | Gly | Glu | Ile | Ile | Ile | Asp | Gly | Val | Asn | Ile | Ala | Lys | Ile | |
| | | | | 1345 | | | | | 1350 | | | | | 1355 | | |
| GGC | CTG | CAC | AAC | CTG | CGC | TTC | AAG | ATC | ACC | ATC | ATT | CCA | CAG | GAT | CCT | 4127 |
| Gly | Leu | His | Asn | Leu | Arg | Phe | Lys | Ile | Thr | Ile | Ile | Pro | Gln | Asp | Pro | |
| 1360 | | | | | 1365 | | | | | 1370 | | | | | | |
| GTT | TTG | TTC | TCG | GGT | TCC | CTC | CGC | ATG | AAC | TTG | GAC | CCT | TTC | AGT | CAG | 4175 |
| Val | Leu | Phe | Ser | Gly | Ser | Leu | Arg | Met | Asn | Leu | Asp | Pro | Phe | Ser | Gln | |
| 1375 | | | | | 1380 | | | | | 1385 | | | | | 1390 | |
| TAT | TCT | GAT | GAA | GAA | GTC | TGG | ATG | GCC | CTG | GAG | CTT | GCT | CAC | CTA | AAG | 4223 |
| Tyr | Ser | Asp | Glu | Glu | Val | Trp | Met | Ala | Leu | Glu | Leu | Ala | His | Leu | Lys | |
| | | | | 1395 | | | | | 1400 | | | | | 1405 | | |
| GGC | TTT | GTG | TCA | GCC | TTG | CCT | GAC | AAG | CTG | AAC | CAT | GAG | TGT | GCA | GAA | 4271 |
| Gly | Phe | Val | Ser | Ala | Leu | Pro | Asp | Lys | Leu | Asn | His | Glu | Cys | Ala | Glu | |
| | | | 1410 | | | | | 1415 | | | | | 1420 | | | |
| GGT | GGA | GAG | AAC | CTG | AGT | GTG | GGG | CAG | CGA | CAG | CTT | GTG | TGC | CTG | GCC | 4319 |
| Gly | Gly | Glu | Asn | Leu | Ser | Val | Gly | Gln | Arg | Gln | Leu | Val | Cys | Leu | Ala | |
| | | | | 1425 | | | | | 1430 | | | | | 1435 | | |
| CGG | GCT | CTG | CTG | AGG | AAG | ACA | AAG | ATT | CTA | GTG | TTG | GAC | GAG | GCT | ACC | 4367 |
| Arg | Ala | Leu | Leu | Arg | Lys | Thr | Lys | Ile | Leu | Val | Leu | Asp | Glu | Ala | Thr | |
| 1440 | | | | | 1445 | | | | | 1450 | | | | | | |
| GCA | GCT | GTG | GAC | CTA | GAG | ACA | GAT | AAC | CTT | ATC | CAG | TCC | ACC | ATC | CGG | 4415 |
| Ala | Ala | Val | Asp | Leu | Glu | Thr | Asp | Asn | Leu | Ile | Gln | Ser | Thr | Ile | Arg | |
| 1455 | | | | | 1460 | | | | | 1465 | | | | | 1470 | |
| ACG | CAG | TTT | GAA | GAC | TGT | ACT | GTG | CTC | ACG | ATT | GCT | CAT | CGG | CTT | AAC | 4463 |
| Thr | Gln | Phe | Glu | Asp | Cys | Thr | Val | Leu | Thr | Ile | Ala | His | Arg | Leu | Asn | |
| | | | | 1475 | | | | | 1480 | | | | | 1485 | | |
| ACC | ATA | ATG | GAC | TAC | ACA | CGG | GTT | ATT | GTC | CTG | GAC | AAA | GGA | GAA | GTT | 4511 |
| Thr | Ile | Met | Asp | Tyr | Thr | Arg | Val | Ile | Val | Leu | Asp | Lys | Gly | Glu | Val | |
| | | | 1490 | | | | | 1495 | | | | | 1500 | | | |
| CGG | GAG | TGT | GGT | GCA | CCC | TCT | GAG | CTC | CTG | CAG | CAA | AGA | GGC | ATC | TTC | 4559 |
| Arg | Glu | Cys | Gly | Ala | Pro | Ser | Glu | Leu | Leu | Gln | Gln | Arg | Gly | Ile | Phe | |
| | | | | 1505 | | | | | 1510 | | | | | 1515 | | |

| | | | | | | | | |
|---|---|---|---|---|---|---|---|---|
| TAC | AGC | ATG | GCC | AAG | GAT | GCT | GGC | TTG | GTG | TGAGCTGGTC TCTGGCTTAT | 4609 |
| Tyr | Ser | Met | Ala | Lys | Asp | Ala | Gly | Leu | Val | | |
| | | | 1520 | | | | | 1525 | | | |

| | | | | |
|---|---|---|---|---|
| CCAATGAGGA | CTGCAGGGCC | AGGATCCCAG | TGTCCAGGCA | TGAGCCAGCA ACCCTGGAAA | 4669 |
| CCTACGCTTC | CCAGACAAAA | CCCAAAAATT | AAAAACAAAA | CCAAACTAAA AGGAAGCAAA | 4729 |
| ATACTTAGGT | GTCTGTCACC | ATTTGGCTTC | ATCCTGGATC | TGACCTTGAA GAAGCTGGAA | 4789 |
| GACAGATGCA | CCCCACTTCA | GATACACGTC | TGGCCTCTGG | CACCCTGAAA GTTCACCCAT | 4849 |
| GCTCCTGCCG | TATCCCACGG | CAAGTCCATG | GGCAGCTAAA | CATACTAGTG ACCAAACACA | 4909 |
| AGCCACACTG | CCTCATGTCT | CTTCAGCCAC | GTCTACGGAT | GCCAAGCCTT GTAGCCTCTC | 4969 |
| CTGGCTTTGC | CAGCTCTCTG | TCACCTATAG | TCGTGTTGGT | TACAGAAGAG TGCATCTTGC | 5029 |
| CTTCAGGTCT | TGCAGTTGAA | ACATGGGAAC | CAAAATGAAC | AAAAAGGAGA GAAAGAAAAC | 5089 |

```
CCCTAAAACG  TTCCTGTCCC  TGTTATGTCA  GTGATGTCCC  CTTCCTGCCA  TCTGGTCTTC  5149

ATGCACGCTG  ACACTGTCCC  TTCTTCAGCA  CAGCTTTCAC  AGGACCTGCT  TAAGACACGG  5209

CCTTGTGAAG  GGACCTAGGC  AGACAGGCTT  GGAACCAGGC  CAGGCAACAC  TCCCTTCACA  5269

AGGACTTATA  CCTTGCCCCT  GCTTTCTGTT  TCTTCCTGTT  CAAAGCTGGG  GAGGGCTCAC  5329

TCCTCACATA  AGGTCTATGA  ATAGTTATAA  GCAGCAAAAG  TCAAGAGCAG  AAGGGATGGT  5389

GCCTGCGGGC  AAGAATCTGG  TATCAAAGAC  AGCCAGAGTT  TCTTATAGGG  CCAGAAGAGA  5449

ACCATTCACA  AATATCAGTG  ATTTCTCCCC  ACTACTTTTG  AGCATCGTTT  CGTGGAGAAG  5509

GATAGTCCCA  AGAATTTGAT  GTCTGGGAGA  AGGTACTAGA  TTCAGGGAGC  AGCCATGCCC  5569

AGCTCTGCAC  TTGATCCTCA  GTCTGAATAC  TTCAAAGTGG  TCCTCTAGGT  TGTGTGAGTT  5629

ACAGACCAAA  GAGAGACCCC  CATGGTTAGC  AAGAACTTGA  TGCCAGCCAC  AGTTCATACT  5689

TGCTTTGAAT  TTTGGCTCTA  ATGTCAGTCC  CAGAGAAGCA  TCCTTTTCT  TTAGGTGGCA  5749

ATATATGTAT  TTATTTTTTG  TAAGTTAATA  CCATTCTTTC  ACTTAAAGG  GCCCAGATTT  5809

CTCCTGAGAG  TCTTTTTGTA  ATGACACTGG  AAACATGACT  ATTTGAAAAT  AATTTGCAGT  5869

AAAGAAAAAT  ATTTCATCCG                                                  5889
```

(2) INFORMATION FOR SEQ ID NO:6:

(i) SEQUENCE CHARACTERISTICS:
        (A) LENGTH: 1528 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ala Leu Arg Ser Phe Cys Ser Ala Asp Gly Ser Asp Pro
 1               5                  10
Leu Trp Asp Trp Asn Val Thr Trp His Thr Ser Asn Pro Asp Phe Thr
15                  20                  25                  30
Lys Cys Phe Gln Asn Thr Val Leu Thr Trp Val Pro Cys Phe Tyr Leu
                35                  40                  45
Trp Ser Cys Phe Pro Leu Tyr Phe Phe Tyr Leu Ser Arg His Asp Arg
            50                  55                  60
Gly Tyr Ile Gln Met Thr His Leu Asn Lys Thr Lys Thr Ala Leu Gly
        65                  70                  75
Phe Phe Leu Trp Ile Ile Cys Trp Ala Asp Leu Phe Tyr Ser Phe Trp
    80                  85                  90
Glu Arg Ser Gln Gly Val Leu Arg Ala Pro Val Leu Leu Val Ser Pro
95                  100                 105                 110
Thr Leu Leu Gly Ile Thr Met Leu Leu Ala Thr Phe Leu Ile Gln Leu
                115                 120                 125
Glu Arg Arg Lys Gly Val Gln Ser Ser Gly Ile Met Leu Thr Phe Trp
            130                 135                 140
Leu Val Ala Leu Leu Cys Ala Leu Ala Ile Leu Arg Ser Lys Ile Ile
        145                 150                 155
Ser Ala Leu Lys Lys Asp Ala His Val Asp Val Phe Arg Asp Ser Thr
    160                 165                 170
Phe Tyr Leu Tyr Phe Thr Leu Val Leu Val Gln Leu Val Leu Ser Cys
175                 180                 185                 190
Phe Ser Asp Cys Ser Pro Leu Phe Ser Glu Thr Val His Asp Arg Asn
                195                 200                 205
```

-continued

| Pro | Cys | Pro | Glu | Ser | Ser | Ala | Ser | Phe | Leu | Ser | Arg | Ile | Thr | Phe | Trp |
|  |  |  | 210 |  |  |  | 215 |  |  |  |  |  | 220 |  |  |

| Trp | Ile | Thr | Gly | Met | Met | Val | His | Gly | Tyr | Arg | Gln | Pro | Leu | Glu | Ser |
|  |  | 225 |  |  |  |  | 230 |  |  |  |  | 235 |  |  |  |

| Ser | Asp | Leu | Trp | Ser | Leu | Asn | Lys | Glu | Asp | Thr | Ser | Glu | Glu | Val | Val |
|  | 240 |  |  |  |  | 245 |  |  |  |  | 250 |  |  |  |  |

| Pro | Val | Leu | Val | Asn | Asn | Trp | Lys | Lys | Glu | Cys | Asp | Lys | Ser | Arg | Lys |
| 255 |  |  |  |  | 260 |  |  |  |  | 265 |  |  |  |  | 270 |

| Gln | Pro | Val | Arg | Ile | Val | Tyr | Ala | Pro | Pro | Lys | Asp | Pro | Ser | Lys | Pro |
|  |  |  |  | 275 |  |  |  |  | 280 |  |  |  |  | 285 |  |

| Lys | Gly | Ser | Ser | Gln | Leu | Asp | Val | Asn | Glu | Glu | Val | Glu | Ala | Leu | Ile |
|  |  |  | 290 |  |  |  |  | 295 |  |  |  |  | 300 |  |  |

| Val | Lys | Ser | Pro | His | Lys | Asp | Arg | Glu | Pro | Ser | Leu | Phe | Lys | Val | Leu |
|  |  | 305 |  |  |  |  | 310 |  |  |  |  | 315 |  |  |  |

| Tyr | Lys | Thr | Phe | Gly | Pro | Tyr | Phe | Leu | Met | Ser | Phe | Leu | Tyr | Lys | Ala |
|  | 320 |  |  |  |  | 325 |  |  |  |  | 330 |  |  |  |  |

| Leu | His | Asp | Leu | Met | Met | Phe | Ala | Gly | Pro | Lys | Ile | Leu | Glu | Leu | Ile |
| 335 |  |  |  |  | 340 |  |  |  |  | 345 |  |  |  |  | 350 |

| Ile | Asn | Phe | Val | Asn | Asp | Arg | Glu | Ala | Pro | Asp | Trp | Gln | Gly | Tyr | Phe |
|  |  |  |  | 355 |  |  |  |  | 360 |  |  |  |  | 365 |  |

| Tyr | Thr | Ala | Leu | Leu | Phe | Val | Ser | Ala | Cys | Leu | Gln | Thr | Leu | Ala | Leu |
|  |  |  | 370 |  |  |  |  | 375 |  |  |  |  | 380 |  |  |

| His | Gln | Tyr | Phe | His | Ile | Cys | Phe | Val | Ser | Gly | Met | Arg | Ile | Lys | Thr |
|  |  | 385 |  |  |  |  | 390 |  |  |  |  | 395 |  |  |  |

| Ala | Val | Val | Gly | Ala | Val | Tyr | Arg | Lys | Ala | Leu | Leu | Ile | Thr | Asn | Ala |
|  | 400 |  |  |  |  | 405 |  |  |  |  | 410 |  |  |  |  |

| Ala | Arg | Lys | Ser | Ser | Thr | Val | Gly | Glu | Ile | Val | Asn | Leu | Met | Ser | Val |
| 415 |  |  |  |  | 420 |  |  |  |  | 425 |  |  |  |  | 430 |

| Asp | Ala | Gln | Arg | Phe | Met | Asp | Leu | Ala | Thr | Tyr | Ile | Asn | Met | Ile | Trp |
|  |  |  |  | 435 |  |  |  |  | 440 |  |  |  |  | 445 |  |

| Ser | Ala | Pro | Leu | Gln | Val | Ile | Leu | Ala | Leu | Tyr | Phe | Leu | Trp | Leu | Ser |
|  |  |  | 450 |  |  |  |  | 455 |  |  |  |  | 460 |  |  |

| Leu | Gly | Pro | Ser | Val | Leu | Ala | Gly | Val | Ala | Val | Met | Ile | Leu | Met | Val |
|  |  | 465 |  |  |  |  | 470 |  |  |  |  | 475 |  |  |  |

| Pro | Leu | Asn | Ala | Val | Met | Ala | Met | Lys | Thr | Lys | Thr | Tyr | Gln | Val | Ala |
|  | 480 |  |  |  |  | 485 |  |  |  |  | 490 |  |  |  |  |

| His | Met | Lys | Ser | Lys | Asp | Asn | Arg | Ile | Lys | Leu | Met | Asn | Glu | Ile | Leu |
| 495 |  |  |  |  | 500 |  |  |  |  | 505 |  |  |  |  | 510 |

| Asn | Gly | Ile | Lys | Val | Leu | Lys | Leu | Tyr | Ala | Trp | Glu | Leu | Ala | Phe | Gln |
|  |  |  |  | 515 |  |  |  |  | 520 |  |  |  |  | 525 |  |

| Asp | Lys | Val | Met | Ser | Ile | Arg | Gln | Glu | Glu | Leu | Lys | Val | Leu | Lys | Lys |
|  |  |  | 530 |  |  |  |  | 535 |  |  |  |  | 540 |  |  |

| Ser | Ala | Tyr | Leu | Ala | Ala | Val | Gly | Thr | Phe | Thr | Trp | Val | Cys | Thr | Pro |
|  |  | 545 |  |  |  |  | 550 |  |  |  |  | 555 |  |  |  |

| Phe | Leu | Val | Ala | Leu | Ser | Thr | Phe | Ala | Val | Phe | Val | Thr | Val | Asp | Glu |
|  | 560 |  |  |  |  | 565 |  |  |  |  | 570 |  |  |  |  |

| Arg | Asn | Ile | Leu | Asp | Ala | Lys | Lys | Ala | Phe | Val | Ser | Leu | Ala | Leu | Phe |
| 575 |  |  |  |  | 580 |  |  |  |  | 585 |  |  |  |  | 590 |

| Asn | Ile | Leu | Arg | Phe | Pro | Leu | Asn | Ile | Leu | Pro | Met | Val | Ile | Ser | Ser |
|  |  |  |  | 595 |  |  |  |  | 600 |  |  |  |  | 605 |  |

| Ile | Val | Gln | Ala | Ser | Val | Ser | Leu | Lys | Arg | Leu | Arg | Ile | Phe | Leu | Ser |
|  |  |  | 610 |  |  |  |  | 615 |  |  |  |  | 620 |  |  |

| His | Glu | Glu | Leu | Glu | Pro | Asp | Ser | Ile | Glu | Arg | Arg | Ser | Ile | Lys | Ser |
|  |  | 625 |  |  |  |  | 630 |  |  |  |  | 635 |  |  |  |

```
Gly Glu Gly Asn Ser Ile Thr Val Lys Asn Ala Thr Phe Thr Trp Ala
640                 645                 650

Arg Gly Glu Pro Pro Thr Leu Asn Gly Ile Thr Phe Ser Ile Pro Glu
655                 660                 665                 670

Gly Ala Leu Val Ala Val Val Gly Gln Val Gly Cys Gly Lys Ser Ser
                675             680                 685

Leu Leu Ser Ala Leu Leu Ala Glu Met Asp Lys Val Glu Gly His Val
            690                 695                 700

Thr Leu Lys Gly Ser Val Ala Tyr Val Pro Gln Gln Ala Trp Ile Gln
        705                 710                 715

Asn Asp Ser Leu Arg Glu Asn Ile Leu Phe Gly His Pro Leu Gln Glu
720                 725                 730

Asn Tyr Tyr Lys Ala Val Met Glu Ala Cys Ala Leu Leu Pro Asp Leu
735                 740                 745                 750

Glu Ile Leu Pro Ser Gly Asp Arg Thr Glu Ile Gly Glu Lys Gly Val
                755                 760                 765

Asn Leu Ser Gly Gly Gln Lys Gln Arg Val Ser Leu Ala Arg Ala Val
            770                 775                 780

Tyr Ser Asn Ser Asp Ile Tyr Leu Phe Asp Asp Pro Leu Ser Ala Val
        785                 790                 795

Asp Ala His Val Gly Lys His Ile Phe Glu Lys Val Gly Pro Met
800                 805                 810

Gly Leu Leu Lys Asn Lys Thr Arg Ile Leu Val Thr His Gly Ile Ser
815                 820                 825                 830

Tyr Leu Pro Gln Val Asp Val Ile Ile Val Met Ser Gly Gly Lys Ile
                835                 840                 845

Ser Glu Met Gly Ser Tyr Gln Glu Leu Leu Asp Arg Asp Gly Ala Phe
            850                 855                 860

Ala Glu Phe Leu Arg Thr Tyr Ala Asn Ala Glu Gln Asp Leu Ala Ser
        865                 870                 875

Glu Asp Asp Ser Val Ser Gly Ser Gly Lys Glu Ser Lys Pro Val Glu
880                 885                 890

Asn Gly Met Leu Val Thr Asp Thr Val Gly Lys His Leu Gln Arg His
895                 900                 905                 910

Leu Ser Asn Ser Ser His Ser Gly Asp Thr Ser Gln Gln His Ser
            915                 920                 925

Ser Ile Ala Glu Leu Gln Lys Ala Gly Ala Lys Glu Glu Thr Trp Lys
        930                 935                 940

Leu Met Glu Ala Asp Lys Ala Gln Thr Gly Gln Val Gln Leu Ser Val
        945                 950                 955

Tyr Trp Asn Tyr Met Lys Ala Ile Gly Leu Phe Ile Thr Phe Leu Ser
960                 965                 970

Ile Phe Leu Phe Leu Cys Asn His Val Ser Ala Leu Ala Ser Asn Tyr
975                 980                 985                 990

Trp Leu Ser Leu Trp Thr Asp Asp Pro Pro Val Val Asn Gly Thr Gln
                995                 1000                1005

Ala Asn Arg Asn Phe Arg Leu Ser Val Tyr Gly Ala Leu Gly Ile Leu
            1010                1015                1020

Gln Gly Ala Ala Ile Phe Gly Tyr Ser Met Ala Val Ser Ile Gly Gly
        1025                1030                1035

Ile Phe Ala Ser Arg Arg Leu His Leu Asp Leu Leu Tyr Asn Val Leu
    1040                1045                1050

Arg Ser Pro Met Ser Phe Phe Glu Arg Thr Pro Ser Gly Asn Leu Val
```

```
                 1055                  1060                  1065                  1070
Asn  Arg  Phe  Ser  Lys  Glu  Leu  Asp  Thr  Val  Asp  Ser  Met  Ile  Pro  Gln
                 1075                  1080                       1085

Val  Ile  Lys  Met  Phe  Met  Gly  Ser  Leu  Phe  Ser  Val  Ile  Gly  Ala  Val
                 1090                  1095                       1100

Ile  Ile  Ile  Leu  Leu  Ala  Thr  Pro  Ile  Ala  Ala  Val  Ile  Ile  Pro  Pro
                 1105                  1110                       1115

Leu  Gly  Leu  Val  Tyr  Phe  Phe  Val  Gln  Arg  Phe  Tyr  Val  Ala  Ser  Ser
            1120                  1125                       1130

Arg  Gln  Leu  Lys  Arg  Leu  Glu  Ser  Val  Ser  Arg  Ser  Pro  Val  Tyr  Ser
1135                  1140                  1145                       1150

His  Phe  Asn  Glu  Thr  Leu  Leu  Gly  Val  Ser  Val  Ile  Arg  Ala  Phe  Glu
                 1155                  1160                       1165

Glu  Gln  Glu  Arg  Phe  Ile  His  Gln  Ser  Asp  Leu  Lys  Val  Asp  Glu  Asn
            1170                  1175                       1180

Gln  Lys  Ala  Tyr  Tyr  Pro  Ser  Ile  Val  Ala  Asn  Arg  Trp  Leu  Ala  Val
            1185                  1190                       1195

Arg  Leu  Glu  Cys  Val  Gly  Asn  Cys  Ile  Val  Leu  Phe  Ala  Ala  Leu  Phe
       1200                  1205                       1210

Ala  Val  Ile  Ser  Arg  His  Ser  Leu  Ser  Ala  Gly  Leu  Val  Gly  Leu  Ser
1215                  1220                  1225                       1230

Val  Ser  Tyr  Ser  Leu  Gln  Ile  Thr  Ala  Tyr  Leu  Asn  Trp  Leu  Val  Arg
                 1235                  1240                       1245

Met  Ser  Ser  Glu  Met  Glu  Thr  Asn  Ile  Val  Ala  Val  Glu  Arg  Leu  Lys
            1250                  1255                       1260

Glu  Tyr  Ser  Glu  Thr  Glu  Lys  Glu  Ala  Pro  Trp  Gln  Ile  Gln  Glu  Thr
            1265                  1270                       1275

Ala  Pro  Pro  Ser  Thr  Trp  Pro  His  Ser  Gly  Arg  Val  Glu  Phe  Arg  Asp
       1280                  1285                       1290

Tyr  Cys  Leu  Arg  Tyr  Arg  Glu  Asp  Leu  Asp  Leu  Val  Leu  Lys  His  Ile
1295                  1300                  1305                       1310

Asn  Val  Thr  Ile  Glu  Gly  Gly  Glu  Lys  Val  Gly  Ile  Val  Gly  Arg  Thr
                 1315                  1320                       1325

Gly  Ala  Gly  Lys  Ser  Ser  Leu  Thr  Leu  Gly  Leu  Phe  Arg  Ile  Asn  Glu
            1330                  1335                       1340

Ser  Ala  Glu  Gly  Glu  Ile  Ile  Ile  Asp  Gly  Val  Asn  Ile  Ala  Lys  Ile
            1345                  1350                       1355

Gly  Leu  His  Asn  Leu  Arg  Phe  Lys  Ile  Thr  Ile  Ile  Pro  Gln  Asp  Pro
       1360                  1365                       1370

Val  Leu  Phe  Ser  Gly  Ser  Leu  Arg  Met  Asn  Leu  Asp  Pro  Phe  Ser  Gln
1375                  1380                  1385                       1390

Tyr  Ser  Asp  Glu  Glu  Val  Trp  Met  Ala  Leu  Glu  Leu  Ala  His  Leu  Lys
                 1395                  1400                       1405

Gly  Phe  Val  Ser  Ala  Leu  Pro  Asp  Lys  Leu  Asn  His  Glu  Cys  Ala  Glu
            1410                  1415                       1420

Gly  Gly  Glu  Asn  Leu  Ser  Val  Gly  Gln  Arg  Gln  Leu  Val  Cys  Leu  Ala
            1425                  1430                       1435

Arg  Ala  Leu  Leu  Arg  Lys  Thr  Lys  Ile  Leu  Val  Leu  Asp  Glu  Ala  Thr
       1440                  1445                       1450

Ala  Ala  Val  Asp  Leu  Glu  Thr  Asp  Asn  Leu  Ile  Gln  Ser  Thr  Ile  Arg
1455                  1460                  1465                       1470

Thr  Gln  Phe  Glu  Asp  Cys  Thr  Val  Leu  Thr  Ile  Ala  His  Arg  Leu  Asn
            1475                  1480                       1485
```

-continued

```
Thr  Ile  Met  Asp  Tyr  Thr  Arg  Val  Ile  Val  Leu  Asp  Lys  Gly  Glu  Val
               1490                    1495                     1500

Arg  Glu  Cys  Gly  Ala  Pro  Ser  Glu  Leu  Leu  Gln  Gln  Arg  Gly  Ile  Phe
          1505                     1510                    1515

Tyr  Ser  Met  Ala  Lys  Asp  Ala  Gly  Leu  Val
     1520                1525
```